(12) United States Patent
Ishidai et al.

(10) Patent No.: US 9,112,168 B2
(45) Date of Patent: Aug. 18, 2015

(54) ORGANIC ELECTROLUMINESCENCE ELEMENT, ILLUMINATION DEVICE AND DISPLAY DEVICE

(75) Inventors: Hiroshi Ishidai, Hachioji (JP); Takeshi Hakii, Sagamihara (JP)

(73) Assignee: KONICA MINOLTA, INC., Tokyo (JP)

( * ) Notice: Subject to any disclaimer, the term of this patent is extended or adjusted under 35 U.S.C. 154(b) by 1 day.

(21) Appl. No.: 14/241,325

(22) PCT Filed: Aug. 10, 2012

(86) PCT No.: PCT/JP2012/070499
§ 371 (c)(1),
(2), (4) Date: Feb. 26, 2014

(87) PCT Pub. No.: WO2013/035490
PCT Pub. Date: Mar. 14, 2013

(65) Prior Publication Data
US 2014/0209886 A1     Jul. 31, 2014

(30) Foreign Application Priority Data

Sep. 7, 2011  (JP) ................................. 2011-194639

(51) Int. Cl.
*H01L 35/24*       (2006.01)
*H01L 51/50*       (2006.01)
*C07D 401/14*    (2006.01)
(Continued)

(52) U.S. Cl.
CPC .......... *H01L 51/5012* (2013.01); *C07D 401/14* (2013.01); *C07D 405/04* (2013.01); *C07D 405/10* (2013.01); *C07D 405/14* (2013.01); *C07D 409/14* (2013.01); *C07D 413/14* (2013.01); *C07D 417/14* (2013.01); *C07D 493/06* (2013.01); *C07D 519/00* (2013.01); *C07F 5/02* (2013.01); *C07F 5/069* (2013.01); *C07F 7/08* (2013.01); *C07F 15/0026* (2013.01); *C07F 15/0033* (2013.01); *C07F 15/0086* (2013.01); *C07F 15/0093* (2013.01); *H01L 51/006* (2013.01); *H01L 51/0072* (2013.01); *H01L 51/0081* (2013.01); *H01L 51/0085* (2013.01); *H01L 51/5275* (2013.01); *C07C 2103/18* (2013.01); *F21V 3/0418* (2013.01); *F21V 31/00* (2013.01); *F21Y 2101/02* (2013.01); *F21Y 2105/008* (2013.01);
(Continued)

(58) Field of Classification Search
CPC .................................................... H01L 51/5012
USPC ........................................... 257/40, E51.001
See application file for complete search history.

(56) References Cited

FOREIGN PATENT DOCUMENTS

| JP | 2001-102175 A | 4/2001 |
|----|---------------|--------|
| JP | 2006-244712 A | 9/2006 |

(Continued)

*Primary Examiner* — Anthony Ho
(74) *Attorney, Agent, or Firm* — Lucas & Mercanti, LLP

(57) ABSTRACT

Provided are an organic electroluminescence element, an illumination device, and a display device having lower driving voltage and excellent luminous efficiency. An organic electroluminescence element has a supporting substrate; and a cathode, a light emitting layer and an adjacent layer provided on the supporting substrate, wherein the adjacent layer is arranged adjacent to the outer side of the cathode (i.e., the side opposite to the light emitting layer), wherein the cathode is a transparent layer containing a metal and having a film thickness of 2 nm or more but less than 10 nm; and wherein the adjacent layer has a refractive index of between 1.6 and 1.95, a film thickness of between 15 nm and 180 nm, and contains no light scattering particle.

16 Claims, 2 Drawing Sheets

(51) Int. Cl.
*C07D 405/14* (2006.01)
*C07D 413/14* (2006.01)
*C07D 405/04* (2006.01)
*C07D 405/10* (2006.01)
*C07D 409/14* (2006.01)
*C07D 417/14* (2006.01)
*C07D 493/06* (2006.01)
*C07D 519/00* (2006.01)
*H01L 51/00* (2006.01)
*H01L 51/52* (2006.01)
*C07F 15/00* (2006.01)
*C07F 5/02* (2006.01)
*C07F 5/06* (2006.01)
*C07F 7/08* (2006.01)
*F21V 31/00* (2006.01)
*F21V 3/04* (2006.01)
*F21Y 101/02* (2006.01)
*F21Y 105/00* (2006.01)

(52) U.S. Cl.
CPC ........ *H01L 51/0087* (2013.01); *H01L 51/5234* (2013.01); *H01L 2251/5361* (2013.01)

(56) References Cited

FOREIGN PATENT DOCUMENTS

| | | |
|---|---|---|
| JP | 2010-015862 A | 1/2010 |
| JP | 2010-040211 A | 2/2010 |
| JP | 2010-098223 A | 4/2010 |
| JP | 2010-102983 A | 5/2010 |
| WO | WO 2010/089683 A1 | 8/2010 |

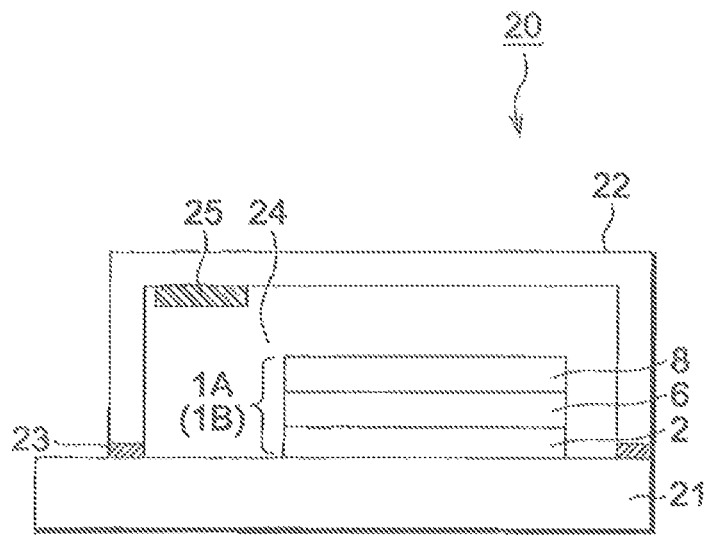

ORGANIC ELECTROLUMINESCENCE ELEMENT, ILLUMINATION DEVICE AND DISPLAY DEVICE

CROSS REFERENCE TO RELATED APPLICATION

This Application is a 371 of PCT/JP2012/070499 filed on Aug. 10, 2012 which, in turn, claimed the priority of Japanese Patent Application No. JP2011-194639 filed on Sep. 7, 2011 both applications are incorporated herein by reference.

TECHNICAL FIELD

The present invention relates to an organic electroluminescence element applicable to various display devices, lighting fixtures and the like, as well as an illumination device and an illumination device using the organic electroluminescence element.

BACKGROUND ART

Recently, planar light-emitting bodies used as backlights for various types of displays, display boards (such as signboards and emergency lights), light sources for lighting fixtures and the like have received attention for its excellent features such as high brightness, high luminous efficiency, small thickness and light weight. Among the planar light-emitting bodies, an organic electroluminescence element (also referred to as organic EL element hereinafter), which uses an organic material to emit light by electric energy from a positive electrode and a negative electrode, has particularly received attention because it can emit light at a low voltage of several volts to several tens volts, is a thin-film type completely-solid stare element, can save space, and the like.

In order to increase the efficiency of the organic EL element, it is necessary to increase light extraction efficiency; however, in the organic EL element, since the distance between a light emitting layer and a metal electrode is small at a level of about several tens nm, waveguide loss of surface plasmon mode light is large, said therefore the light extraction efficiency does not increase. A known method to reduce the waveguide loss of the surface plasmon mode light is to configure the element as a top emission type organic EL element in which the anode is a reflecting electrode.

A metal thin-film is used as the cathode of the top emission type organic EL element, whereon the metal thin-film is thinned to a degree at which electrical conductivity is not damaged. However, if the metal thin-film has a thickness that ensures sufficient electrical conductivity, transmission of the cathode will decrease, and therefore extraction efficiency of the light emitted from inside will be reduced; further, light entering the cathode at a given angle will be more strongly reflected by an interface between the cathode and the organic layer, and therefore variation in brightness of the light-emitting element with the viewing angle will become larger.

Patent document 1 discusses a method to improve the light extraction efficiency by using optical interference; however, the improvement of light extraction efficiency achieved by using optical interference provides no freedom degree in film thickness of light emitting layer, nor freedom degree in the distance between a reflecting electrode and a semi-transmissive electrode, and therefore it is difficult to ensure compatibility between the light extraction efficiency and other performances such as voltage, lifetime and the like.

Further, Patent document 2 discusses a method to improve the light extraction efficiency by providing a light scattering layer on the outer side of a transmissive electrode; however, the problem with such a method is that it is not possible to avoid optical loss caused by back scatter of the light scattering layer, and that, in the case of a dual emission type organic EL lighting, transmission of the element will decrease due to provision of the light scattering layer.

PRIOR ART DOCUMENTS

Patent Documents

[Patent document 1] Japanese Unexamined Patent Application Publication No. 2006-241712

[Patent document 2] Japanese Unexamined Patent Application Publication No. 2010-15362

DISCLOSURE OF THE INVENTION

Problems to be Solved by the Invention

The present inversion re made re view of the aforesaid problems; and at object of the present invention is to provide an organic electroluminescence element, an illumination device and a display device having lower driving voltage and excellent luminous efficiency.

Means for Solving the Problems

The aforesaid object of the present invention can be achieved by the following configurations.

1. Configuration 1 is an organic electroluminescence element including: a supporting substrate; and a cathode, a light emitting layer and an adjacent layer provided on the supporting substrate, wherein the adjacent layer is arranged adjacent to the outer side of the cathode (i.e., the side opposite to the light, emitting layer), wherein the cathode is a transparent layer containing a metal and having a film thickness of 2 nm or core but less than 10 nm; and wherein the adjacent layer has a refractive index of between 1.6 and 1.95, a film thickness of between 15 nm and 180 nm, and contains no light scattering particle.

2. Configuration 2 is an organic electroluminescence element according to configuration 1, wherein the adjacent layer contains a metal complex compound having a quinoline derivative as its ligand.

3. Configuration 3 is an organic electroluminescence element according to configurations 1 or 2, wherein the adjacent layer contains a compound, represented by the following general formula (1):

(Ar1)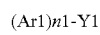n1-Y1                       General Formula (1)

where n1 represents an integer of 1 or core; Y1 represents either a substituent if n1 is one, or a bond or an n1-valent linking group if n1 is 2 or more; Ar1 represents a group represented by the following general, formula (A); and, if n1 is 2 or more, a plurality of Ar1 may be either identical to or different from each other; wherein the compound represented by General Formula (1) has at least two condensed aromatic heterocycles in the molecule, each formed by condensing three or more rings,

[Chemical Formula 1]

GENERAL FORMULA (A)

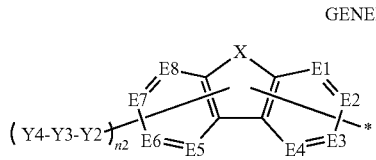

where X represents —N(R)—, —O—, —S— or —Si(R)(R')—, and E1 to E8 each represent —C(R1)= or —N=, wherein R, R' and R1 each represent a hydrogen atom, a substituent or a linking site with Y1; * represents a linking site with Y1; Y2 represents a bond or a divalent linking group; Y3 and Y4 each represent a group derived from a 5-membered or 6-membered aromatic ring, wherein at least one of Y3 and Y4 represents a group derived from an aromatic heterocyclic containing a nitrogen atom as a ring constituent atom; and no represents an integer of 1 to 4.

4. Configuration 4 is an organic electroluminescence element according to configuration 3, wherein the compound represented by the general formula (1) is a compound represented by the following general formula (2):

[Chemical Formula 2]

GENERAL FORMULA (2)

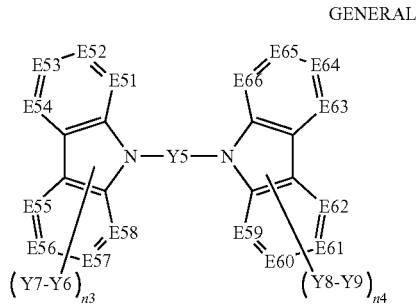

where Y5 represents a divalent linking group which is an arylene group, a heteroarylene group or a combination of the arylene group and the heteroarylene group; E51 to E66 each represent —C(R3)= or —N=, wherein R3 represents a hydrogen atom or a substituent; Y6 to Y9 each represent a group derived from an aromatic hydrocarbon ring or a group derived from an aromatic heterocycle, wherein at least one of Y6 and Y7 and at least one of Y8 and Y9 each represent a group derived from an aromatic heterocycle containing an N atom; and n3 and n4 each represent an integer of 0 to 4, wherein the sum of n3 and n4 is 2 or more.

5. Configuration 5 is an organic electroluminescence element according to configuration 4, wherein the compound represented by the general formula (2) is a compound represented by the following general formula (3):

[Chemical Formula 3]

GENERAL FORMULA (3)

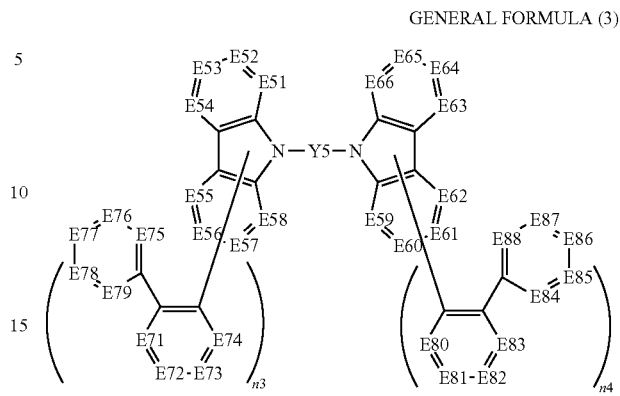

where Y5 represents a divalent linking group which is an arylene group, a heteroarylene group or a combination or the a arylene group and the heteroarylene group; E51 to E66 and E71 to E88 each represent —(R3)= or —N=, wherein R3 represents a hydrogen atom or a substituent, and wherein at least one of E71 to E79 and at least one of E80 so E88 each represent —N=; and n3 and n4 each represent an integer of 0 to 4, wherein the sum of n3 and n4 is 2 or more.

6. Configuration 6 is an organic electroluminescence element according any one of configurations 1 to 5, wherein the main component of the cathode is silver.

7. Configuration 7 is an organic electroluminescence element according any one of configurations 1 to 6, further including: an electron transporting layer arranged between the cathode and the light emitting layer, wherein the electron transporting layer contains an alkali metal or an alkali metal compound.

8. Configuration 8 is an organic electroluminescence element according to configuration 7, wherein the alkali metal or the alkali metal compound is kalium or a kalium compound.

9. Configuration 9 is an organic electroluminescence element according configuration 7 or 8, wherein the electron transporting layer contains a compound represented by one of general formulas (1) to (3).

10. Configuration 10 is an organic electroluminescence element according to any one of configurations 1 to 9, wherein the light emitting layer contains a compound represented by the following general formula (4):

[Chemical Formula 4]

GENERAL FORMULA (4)

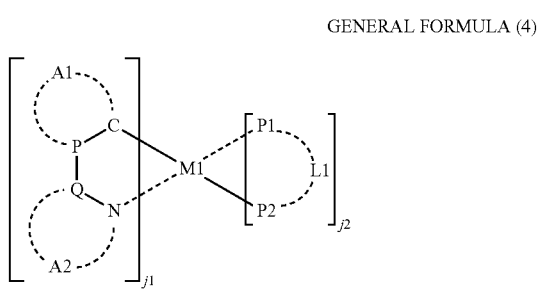

where P and Q each represent a carbon atom or a nitrogen atom; A1 represents an atom group which forms an aromatic hydrocarbon ring or an aromatic heterocycle with P—C; A2 represents an atom group which forms an aromatic heterocycle with Q-N; P1-L1-P2 represents a bidentate ligand, wherein P1 and P2 each independently represent a carbon atom, a nitrogen atom or an oxygen atom, and L1 represents an atom group which forms the bidentate ligand with P1 and P2; j1 represents an integer or 1 to 3, and j2 represents an integer of 0 to 2, wherein the sum of j1 and is j2 is 2 or 3; and M1 represents a transition metal element of groups 8 to 10 in the periodic table of elements.

11. Configuration 11 is an organic electroluminescence element according to configuration 10, wherein the compound represented by the general formula (4) is a compound represented by the following general formula (5):

[Chemical Formula 5]

GENERAL FORMULA (5)

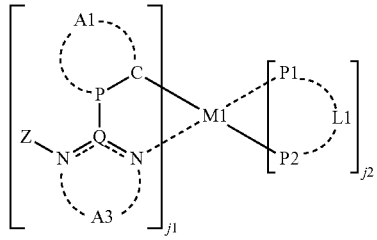

where Z represents a hydrocarbon ring group or a heterocyclic, group; P and Q each represent a carbon atom or a nitrogen atom; A1 represents an atom group which forms an aromatic hydrocarbon ring or an aromatic heterocycle with P—C; A3 represents —C(R01)=C(R02)-, —N=C(R02)-, —C(R01)=N— or =N—N—, wherein R01 and R02 each represent a hydrogen atom or a substituent; P1-L1-P2 represents a bidentate ligand, wherein P1 and P2 each independently represent a carbon atom, a nitrogen atom or an oxygen atom, and L1 represents an atom group which forms the bidentate ligand with P1 and P2; j1 represents an integer of 1 to 3, and j2 represents an integer of 0 to 2, wherein the sum of j1 and j2 is 2 or 3; and M1 represents a transition metal element of groups 8 to 10 in the periodic table of elements.

12. Configuration 12 is an organic electroluminescence element according to configuration 10 or 11, wherein M1 represents iridium.

13. Configuration 13 is an organic electroluminescence element according to any one of configurations 1 to 12, further including: an auxiliary electrode arranged between the cathode and the adjacent layer.

14. Configuration 14 is an organic electroluminescence element according to any one of configurations 1 to 13, wherein the organic electroluminescence element is a dual emission type organic electroluminescence element.

15. Configuration 15 is an illumination device including an organic electroluminescence element described in any one or configurations 1 to 14.

16. Configuration 16 is a display device including an organic electroluminescence element described in any one of configurations 1 to 14.

Advantages of the Invention

According to the present invention, it is possible to provide an organic electroluminescence element, an illumination device and a display device having lower driving voltage and excellent luminous efficiency.

BRIEF DESCRIPTION OF DRAWINGS

FIG. 3 is a cross-sectional view showing an aspect or an illumination device according to the present invention.

MODES FOR CARRYING OUT THE INVENTION

An embodiment for carrying out the present invention will be described below; it should be noted that the embodiment described below represents a representative example of embodiments of the present invention, and the present invention is not limited thereto without departing from the spirit and scope of the present invention.

Organic EL Element

First, preferred concrete examples of the layer structure of an organic electroluminescence element (i.e., organic EL element) according to the present invention will be described below.

Figure 1:
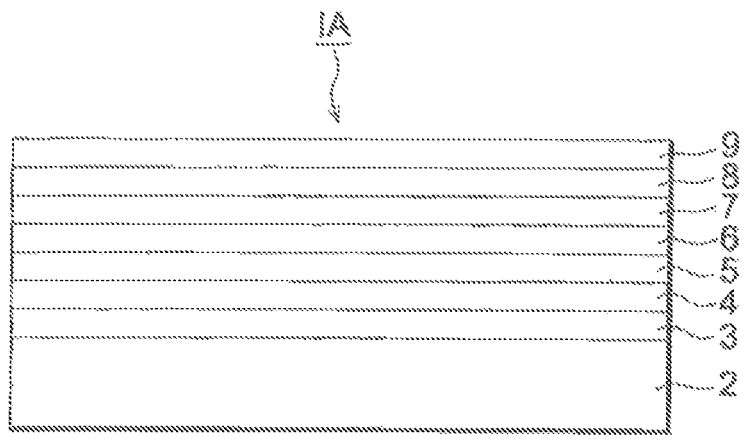
FIG. 1 is a cross-sectional view showing an example of the configuration of an organic electroluminescence element according to the present invention.

As shown in FIG. 1, a preferred concrete example of the layer structure of an organic EL element 1A according to the present invention is shown as below:

(i) Supporting substrate 2/anode 3/hole injecting layer 4/hole transporting layer 5/light emitting layer 6/electron transporting layer 7/cathode 8/adjacent layer Incidentally, other concrete examples of the layer structure of the organic EL element according to the present invention are shown as below:

(ii) Supporting substrate/anode/hole injecting layer/hole transporting layer/light emitting layer/electron transporting layer/electron injecting layer/cathode/adjacent layer (iii) Supporting substrate/anode/hole injecting layer/hole transporting layer/light emitting layer/hole blocking layer/electron transporting layer/cathode/adjacent layer (iv) Supporting substrate/anode/hole injecting layer/hole transporting layer/first light emitting layer/second light emitting layer/electron transporting layer/electron injecting layer/cathode/adjacent layer (v) Supporting substrate/anode/hole rejecting layer/hole transporting layer/first light emitting layer/second light emitting layer/third light emitting layer/electron transporting layer/electron injecting layer/cathode/adjacent layer (vi) Supporting substrate/anode/hole injecting layer/hole transporting layer/first light emitting layer/second light emitting layer/hole blocking layer/electron transporting layer/electron injecting layer/cathode/adjacent layer (vii) Supporting substrate/auxiliary electrode layer/anode/hole injecting layer/hole transporting layer/first light emitting layer/electrification generating layer/second light emitting layer/hole blocking layer/electron transporting layer/electron injecting layer/cathode/adjacent layer Details of each layer will be described later.

The organic EL element according to the present invention has a transparent cathode and a light emitting layer. Incidentally, in the present invention, the term "transparent" of the transparent cathode means that the light transmission of the cathode for light with a wavelength of 550 nm is 50% or higher. Such light transmission can be achieved by forming the cathode and the electron transporting layer with below-mentioned material in below-mentioned film thickness.

The transparent cathode is not particularly limited as long as it is a thin-film containing a metal having electrical conductivity; examples of the metal contained in the thin-film include aluminum, silver, gold, platinum, copper, tin, indium, magnesium, zinc, germanium, bismuth, strontium or the like; further, the metal contained in the thin-film may also be a mixture (alloy) of two or more the above metals, or a mixture (alloy) of two or more metals including the above metal(s).

Further, the transparent cathode may also be a thin-film formed of one aforesaid metal or alloy and one organic compound by co-deposition, or the like.

The anode may either be transparent or non-transparent depending on desired application. It is preferred that the light emitting layer contains at least two kinds of light emitting materials, each having different emission color; and the light emitting layer may also be a light emitting layer unit formed by one or a plurality of light emitting layers 6. Further, the hole transporting layer may include a hole injecting layer and an electron blocking layer (not shown). The details will be described later.

Incidentally, the organic EL element according to the present invention may be either a top emission type organic EL element or a dual emission type organic EL element, and may be used as a planar light-emitting body, for example.

For the sake of convenience, in the following paragraphs, the configuration of the organic EL element according to the present invention will be described in the order from the cathode, which is the upper layer.

Cathode

As mentioned above, the cathode (also referred to as cathode electrode or the like) is not particularly limited as long as it is a thin-film containing a metal having electrical conductivity; examples of the metal contained in the thin-film include aluminum, silver, gold, platinum, copper, tin, indium, magnesium, zinc, germanium, bismuth, strontium, barium or the like; further, the metal contained in the thin-film may also be a mixture (alloy) of two or more the above metals, or a mixture (alloy) of two or more metals including the above metal(s); and further, the cathode may also be a thin-film formed of one aforesaid metal or alloy and one organic compound by co-deposition or the like, and having a function as an electrode.

It is preferred the cathode is formed by a deposition method if the cathode is formed of one material, or by a co-deposition method if the cathode is formed of two or more materials.

Further, it is preferred that the film thickness of the cathode is within a range of equal to or larger than 2 nm but smaller than 10 nm. If the film thickness is smaller than 10 nm, the absorption of the metal-containing layer will be less, and the transmission of the element will be improved, which will be preferable. Further, if the film thickness is larger than 2 nm, the electrical conductivity of the layer will be good, and the driving voltage will not be increased, which will be preferable.

Preferred examples of the metal contained in the cathode are the aforesaid metals; however, it is more preferred that the metal contained in the cathode is aluminum, silver, gold, indium, magnesium, zinc or the like; further, for purpose of adjusting work function to improve electron injection performance, it is also preferred the cathode is a thin-film formed of two or more these metals, or a thin-film formed of two or more metals including the these metal(s), or a thin-film formed of two or more materials including these metal(s) and an organic compound.

It is particularly preferred that the metal contained in the cathode is silver, gold, indium, zinc, magnesium or the like.

Adjacent Layer

The adjacent layer adjacent to the cathode on the side opposite to the light emitting layer is not particularly limited as long as its refractive index is in a range between 1.6 and 1.95 and its film thickness is in a range between 15 nm and 180 nm, preferably in a range between 50 nm and 150 nm, and more preferably in a range between 50 nm and 120 nm. It is preferred that the adjacent layer satisfies the refractive index in a region between 350 nm and 800 nm. It is preferred that the adjacent layer contains a metal complex compound or a compound represented by General Formula (1). The adjacent layer is characterized to contain light scattering particles.

Similar to the below-mentioned light emitting layer, the adjacent layer may be formed by forming a film of one of the below compounds with a refractive index between 1.6 and 1.95 by employing a known method such as a vacuum deposition method, a spin coating method, a casting method, an LB method, an ink-jet method or the like.

Examples of the compound contained in the adjacent layer include a pyridine derivative, a BINAP, a bipyridine derivative, a phenanthroline derivative, an amino acid derivative, an imino acid derivative, a terpyridine derivative, EDTA, a crown ether derivative, and a quinoline derivative. Preferred examples of the compound contained in the adjacent layer include a metal complex compound which has a pyridine derivative, a phenanthroline derivative, or a quinoline derivative as its ligand; and particularly preferred examples of the compound contained in the adjacent layer include a metal complex compound which has a quinoline derivative as its ligand.

Examples of the central metal of the metal complex compound having a quinoline derivative as its ligand include aluminum, lithium, silver, copper, cobalt, beryllium, zinc, nickel, ruthenium, and phosphorous. Preferred examples of snob central metal include aluminum, lithium, copper, cobalt, ruthenium and the like; and particularly preferred examples of such central metal include aluminum and lithium.

Examples of the metal complex compound having a quinoline derivative as its ligand include lithium quinolate, tris(8-quinolinol)aluminum (Alq 3), tris(5,7-dichloro-8-quinolinol) aluminum, tris 5,7-dibromo-8-quinolinol)aluminum, tris(2-methyl-8-quinolinol)aluminum, tris(5-methyl-8-quinolinol) aluminum and the like.

Compound Represented by General Formula (1)

The compound represented by General Formula (1) will be described below.

Examples of the substituent represented by Y1 in General Formula (1) include: an alkyl group (for example, a methyl group, an ethyl group, a propyl group, an isopropyl group, a tert-butyl, group, a pentyl group, a hexyl group, an octyl group, a dodecyl group, a tridecyl group, a tetradecyl group, a pentadecyl group and the like); a cycloalkyl group (for example, a cyclopentyl group, a cyclohexyl group and the like); an alkenyl group (for example, a vinyl group, an allyl group and the like); an alkynyl group (for example, an ethynyl group, a propargyl group and the like); an aromatic hydrocarbon group (also referred to as an aromatic carbon ring group, an aryl group or the like, and examples of the aromatic hydrocarbon group include a phenyl group, a p-chlorophenyl group, a mesityl group, a tolyl group, a xylyl group, a naphthyl group, an anthryl group, an azulenyl group, an acenaphthenyl group, a fluorenyl group, a phenanthryl group, an indenyl group, a pyrenyl group, a biphenyryl group and the like); an aromatic heterocyclic group (for example, a furyl group, a thienyl group, a pyridyl group, a pyridazinyl group, a pyrimidinyl group, a pyrazinyl group, a triazinyl group, an imidazolyl group, a pyrazolyl group, a thiazolyl group, a quinazolinyl group, a carbazolyl group, a carbolinyl group, a diazacarbazolyl group (which is formed by substituting any one of carbon atoms constituting a carboline ring of the aforesaid carbolinyl group with a nitrogen atom), a phtharazinyl group and the like); a heterocyclic group (for example, a pyrrolidyl group, an imidazolidyl group, a morpholyl group, an oxazolidyl group and the like); an alkoxy group (for example, a methoxy group, an ethoxy group, a propyloxy group, a pentyloxy group, an hexyloxy group, an octyloxy group, a dodecyloxy group and the like); a cycloalkoxy group (for example, a cyclopentyloxy group, a cycloahexyloxy group and the like); an aryloxy group (for example, a phenoxy group, a naphthyloxy group and the like); an alkylthio group (for example, a methylthio group, an ethylthio group, a propylthio group, a pentylthio group, a hexylthio group, an octylthio group, a dodecylthio group and the like); a cycloalkylthio group (for example, a cyclopentylthio group, a cyclohexylthio group and the like); an arylthio group (for example, a phenylthio group, a naphthylthio group and the like); an alkoxycarbonyl group (for example, a methyloxycarbonyl group, an ethyloxycarbonyl group, a butyloxycarbonyl group, an octyloxycarbonyl group, a dodecyloxycarbonyl group and the like); an aryloxycarbonyl group (for example, a phenyloxycarbonyl group, a naphthyloxycarbonyl group and the like); a sulfamoyl group (for example, an aminosulfonyl group, a methylaminosulfonyl group, a dimethylaminosulfonyl group, a butylaminosulfonyl group, a hexylaminosulfonyl group, a cyclohexylaminosulfonyl group, an octylaminosulfonyl group, a dodecylaminosulfonyl group, a phenylaminosulfonyl group, a naphthylaminosulfonyl group, a 2-pyridylaminosulfonyl group and the like); an acyl group (for example, an acetyl group, an ethylcarbonyl group, a propylcarbonyl group, a pentylcarbonyl group, a cyclohexylcarbony group, an octylcarbonyl group, a 2-ethylhexylcarbonyl group, a dodecylcarbonyl group, a phenylcarbonyl group, a naphthylcarbonyl group, a pyridylcarbonyl group and the like); an acyloxy group (for example, an acetyloxy group, an ethylcarbonyloxy group, a butylcarbonyloxy group, an octylcarbonyloxy group, a dodecylcarbonyloxy group, a phenylcarbonyloxy group and the like); an amido group (for example, a methylcarbonylamino group, an ethylcarbonylamino group, a dimethylcarbonylamino group, a propylcarbonylamino group, a pentylcarbonylamino group, a cyclohexylcarbonylamino group, a 2-ethylhexylcarbonylamino group, an octylcarbonylamino group, a dodecylcarbonylamino group, a phenylcarbonylamino group, a naphthylcarbonylamino group and the like); a carbamoyl group (for example, an aminocarbonyl group, a methylaminocarbonyl group, a dimethylaminocarbonyl group, a propylaminocarbonyl group, a pentylaminocarbonyl group, a cyclohexylaminocarbonyl group, an octylaminocarbonyl group, a 2-ethylhexylaminocarbonyl group, a dodecylaminocarbonyl group, a phenylaminocarbonyl group, a naphthylaminocarbonyl group, a 2-pyridylaminocarbonyl group and the like); an ureido group (for example, a methylureido group, an ethylureido group, a pentylureido group, a cyclohexylureido group, an octylureido group, a dodecylureido group, a phenylureido group, a naphthylureido group, a 2-pyridylaminoureido group and the like); a sulfinyl group (for example, a methylsulfinyl group, an ethylsulfinyl group, a butylsulfinyl group, a cyclohexylsulfinyl group, a 2-ethylhexylsulfinyl group, a dodecylsulfinyl group, a phenylsulfinyl group, a naphthylsulfinyl group, a 2-pyridylsulfinyl group and the like); an alkylsulfonyl group (for example, a methylsulfonyl group, an ethylsulfonyl group, a butylsulfonyl group, a cyclohexylsulfonyl group, a 2-ethylhexylsulfonyl group, a dodecylsulfonyl group and the like); an arylsulfonyl group or a heteroarylsulfonyl group (for example, a phenylsulfonyl group, a naphthylsulfonyl group, a 2-pyridylsulfonyl group and the like); an amino group (for example, an amino group, an ethylamino group, a dimethylamino group, a butylamino group, a cyclopentylamino group, a 2-ethylhexylamino, a dodecylamino group, an anilino group, a naphthylamino group, a 2-pyridylamino group, a piperidyl group (also referred to as a piperidinyl group), a 2,2,6,6-tetramethyl piperidinyl group and the like); a halogen atom (for example, a fluorine atom, a chlorine atom, a bromine atom and the like); a fluorohydrocarbon group (for example, a fluoromethyl group, a trifluoromethyl group, a pentafluoroethyl group, a pentafluorophenyl group and the like); a cyano group; a nitro group; a hydroxyl group; a mercapto group; a silyl group (for example, a trimethylsilyl group, a triisopropylsilyl group, a triphenylsilyl group, a phenyldiethylsilyl group and the like); a phosphate group (for example, dihexylphosphoryl group and the like); a phosphite group (for example, diphenylphosphinyl group and the like); a phosphono group, and the like.

These substituents may further be substituted by the aforesaid substituent. Further, a plurality of these substituents may be bonded to each other to form a ring.

Concrete examples of the n1-valent linking group represented by Y1 in General Formula (1) include a divalent linking group, a trivalent linking group, a tetravalent linking group and the like.

Example of the divalent linking group represented by Y1 in General Formula (1) include: an alkylene group (for example, an ethylene group, a trimethylene group, a tetramethylene group, a propylene group, an ethylethylene group, a pentamethylene group, a hexamethylene group, a 2,2,4-trimethylhexamethylene group, a heptamethylene group, an octamethylene group, nonamethylene group, a decamethylene group, an undecamethylene group, a dodecamethylene group, a cyclohexylene group (for example, a 1,6-cyclohexanediyl group and the like), a cyclopenthylene group (for example, a 1,5-cyclopentanediyl group and the like) and the like); an alkenylene group (for example, a vinylene group, a propenylene group, a butenylene group, a pentenylene group, a 1-methylvinylene group, a 1-methylpropenylene group, a 2-methylpropenylene group, a 1-methylpentenylene group, a 3-methylpentenylene group, a 1-ethyvinylene group, a 3-ethylbutenylene group and the like); an alkynylene group (for example, an ethynylene group, a 1-propynylene group, a 1-butynylene group, a 1-pentynylene group, a 1-hexynylene group, a 2-butynylene group, a 2-pentynylene group, a 1-methylethynylene group, a 3-methyl-1-propynylene group, a 3-methyl-1-butynylene group and the like); an arylene group (for example, an o-phenylene group a p-phenylene group, a naphthalenediyl group, an anthracenediyl group, a naphthacenediyl group, a pyrenediyl group, a naphthylnaphthalenediyl group, a biphenyldiyl group (for example, a [1,1'-biphenyl]-4,4'-diyl group, a 3,3'-biphenyldiyl group and, 3,6-biphenyldiyl group and the like), a terphenyldiyl group, a quaterphenyldiyl group, a quinquephenyldiyl group, a sexiphenyldiyl group, a septiphenyldiyl group, an octiphenyldiyl group, a nobiphenyldiyl group, a deciphenyldiyl group and the like); a heteroarylene group (for example, a divalent group derived from a group consisting of a carbazole group, a carboline ring, a diazacarbazole ring (also referred to as a monoazacarboline group, indicating a ring formed by substituting one of carbon atoms constituting a carboline ring with a nitrogen atom), a triazole ring, a pyrrole ring, a pyridine ring, a pyrazine ring, a quinoxaline ring, a thiophene ring, an oxadiazole ring, a dibenzofuran ring, a dibenzothiophene ring, an indole ring and the like), a chalcogen atom such as oxygen, sulfur or the like, a group derived from a condensed aromatic heterocycle formed by condensing three or more, and the like (herein, it is preferred that the condensed aromatic heterocycle formed by condensing three or more rings is a condensed aromatic heterocycle which contains a hetero atom selected from N, O and S as an element constituting a condensed ring; concrete examples of such condensed aromatic heterocycle include an acridine ring, a benzoquinoline ring, a carbazole ring, a phenazine ring, a phenanthridine ring, a phenanthroline ring, a carboline ring, a cycladine ring, a quindoline ring, a the benidine ring, a quinindoline ring, a triphenodithiazine ring, a triphenodioxazine, a phenanthrazine ring, an anthrazine ring, a perimizine ring, a diazacarbazole ring (indicating a ring formed by substituting one of carbon atoms constituting a carboline ring with a nitrogen atom), a phenanthroline ring, a dibenzofuran ring, a dibenzothiophene ring, a naphthofuran ring, a naphthothiophene ring, a benzodifuran ring, a benzodithiophene ring, a naphthodifuran ring, a naphthodithiophene ring, an anthrafuran ring, an anthradifuran ring, an anthrathiophene ring, an anthradithiophene ring, a thianthrene ring, a phenoxathiin ring, a thiophanthrene ring (naphthothiophene ring) and the like).

Examples of the trivalent linking group represented by Y1 in General Formula (1) include an ethanetriyl group, a propanetriyl group, a butanetriyl group, a pentanetriyl group, a hexanetriyl group, a heptanetriyl group, an octanetriyl group, a nonanetriyl group, a decanetriyl group, an undecanetriyl group, a dodecanetriyl group, a cyclohexanetriyl group, a cyclopentanetriyl group, a benzenetriyl group, a naphthalenetriyl group, a pyridinetriyl group, a carbazoletriyl group and the like.

The tetravalent linking group represented by Y1 in General Formula (1) is a group which has an additional linking group to any of the aforesaid trivalent linking groups. Examples of the tetravalent linking group include a propandiylidene group, a 1,3-propandiyl-2-ylidene group, a butanediylidene group, a pentanediylidene group, a hezanediylidene group, a heptanediylidene group, an octanediylidene group, a nonanediylidene group, a decanediylidene group, an undecanediylidene group, a dodecanediylidene group, a cyclohezanediylidene group, a cyclopentanediylidene group, a benzenetetrayl group, a naphthalenetetrayl group, a pyridinetetrayl group, a carbazoletetrayl group and the like.

The aforesaid divalent, trivalent and tetravalent linking groups may each have a substituent represented by Y1 in General Formula (1).

In the compound represented by General Formula (1), it is preferred, that Y1 represent a group derived from a condensed aromatic heterocycle formed by condensing three or more rings, and it is preferred that the condensed aromatic heterocycle formed by condensing three or more rings is a dibenzofuran ring or a dibenzothiophene ring. Further, it is preferred that n1 is 2 or more.

Further, the compound represented by General Formula (1) has, in a molecule, at least two condensed aromatic heterocycles each formed by condensing three or more rings.

When Y1 represents an n1-valent linking group, Y1 is preferably non-conjugated in order to keep the triplet excitation energy of the compound represented by General Formula (1) high, and is preferably constituted of aromatic rings (an aromatic hydrocarbon ring+an aromatic heterocycle) in order to improve Tg (also referred to as "glass transition point" or "glass transition temperature").

Here, the "non-conjugated" indicates that a linking group cannot be expressed with alternation of single and double bonds, or that a conjugation of aromatic rings which constitute a linking group is sterically broken.

(Group Represented by General Formula (A))

In General Formula (1), Ar1 is a group represented by the following General Formula (A).

[Chemical Formula 6]

GENERAL FORMULA (A)

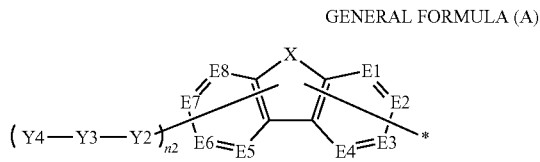

In General Formula (A), X represents —N(R)—, —O—, —S— or —Si(R)(R')—, and E1 to E8 each represent —C(R1)= or —N=, wherein R, R' and R1 each represent a hydrogen atom, a substituent or a linking site with Y1; * represents a linking site with Y1; Y2 represents simply a bond or a divalent linking group; Y3 and Y4 each represent a group derived from a 5-membered or 6-membered aromatic ring, wherein at least one of Y3 and Y4 represents a group derived from an aromatic heterocycle containing a nitrogen atom as a ring constituent atom; and n2 represents an integer of 1 to 4.

Here, the substituents represented by R, R' or R1 in —N(R)— or —Si(R)(R')— represented by X and in —C(R1)= represented by each of E1 to E8 in General Formula (A) are each synonymous with the substituent represented by Y1 in General Formula (1).

The divalent linking group represented by Y2 in General Formula (A) is synonymous with the divalent linking group represented by Y1 in General Formula (1).

Examples of the 5-membered or 6-membered aromatic ring used to form a group derived from a 5-membered or 6-membered aromatic ring represented by each or Y3 and Y4 in General Formula (A) include a benzene ring, an oxazole ring, a thiophene ring, a furan ring, a pyrrole ring, a pyridine ring, a pyridazine ring, a pyrimidine ring, a pyrazine ring, a diazine ring, a trizine ring, an imidazole ring, an isozazole ring, a pyrazole ring, a triazole ring and the like.

At least one of the groups derived from 5-membered or 6-membered aromatic rings respectively represented by Y3 and Y4 is a group derived from an aromatic heterocycle containing a nitrogen atom as a ring constituent atom. Examples of the aromatic heterocycle containing a nitrogen atom as a ring constituent atom include an oxaxole ring, a pyrrole ring, a pyridine ring, a pyridazine ring, a pyrimidine ring, a pyrazine ring, the diazine ring, a triazine ring, an imidazole ring, an isoxazole ring, a pyrazole ring, a triazole ring and the like.

(Preferred Group Represented by Y3)

In General Formula (A), the group represented by Y3 is preferably a group derived from the aforesaid 6-membered aromatic ring, and further preferably a group derived from a benzene ring, (Preferred Group Represented by Y4)

In General Formula (A), the group represented by Y4 is preferably a group derived from the aforesaid 6-membered aromatic ring, and further preferably a group derived from the aromatic heterocycle containing a nitrogen atom as a ring constituent atom, and particularly preferably a group derived from a pyridine ring.

Preferred Group Represented by General Formula (A))

The group represented by General Formula (A) is preferably a group represented by one of the following General Formulae (A-1), (A-2), (A-3) and (A-4).

[Chemical Formula 7]

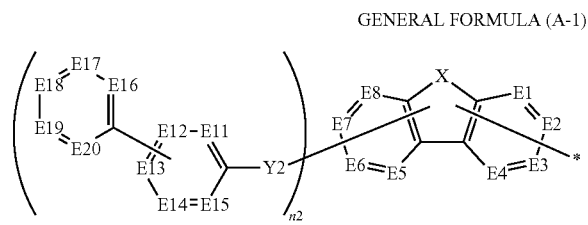

GENERAL FORMULA (A-1)

In General Formula (A-1), X represents —N(R)—, —O—, —S— or —Si(R)(R')—, and E1 to E8 each represent —C(R1)- or —N═, wherein R, R' and R1 each represent a hydrogen atom, a substituent or a linking site with Y1; Y2 represents simply a bond or a divalent linking group; E11 to E20 each represent —C(R2)═ or —N═, wherein at least one of E11 to E20 represents —N═, and wherein R2 represents a hydrogen atom, a substituent or a linking site; wherein at least one of E11 and E12 represents —C(R2)═, wherein R2 represents a linking site; n2 represents an integer of 1 to 4; and * represents a linking site with Y1 in General Formula (1).

[Chemical Formula 8]

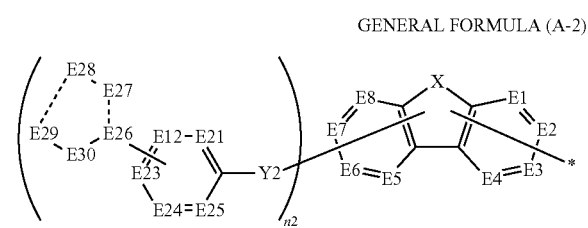

GENERAL FORMULA (A-2)

In General Formula (A-2), X represents —N(R)—, —O—, —S— or —Si(R)(R')—, and E1 to E8 each represent —C(R1)═ or —N═, wherein R, R' and R1 each represent a hydrogen atom, a substituent or a linking site with Y1; Y2 represents simply a bond or a divalent linking group; E21 to E25 each represent —C(R2)═ or —N═, and E26 to E30 each represent —C(R2)═, —N═, —O—, —S— or —Si(R3)(R4)-, wherein at least one of E21 to E30 represents —N═, and wherein R2 represents a hydrogen atom, a substituent or a linking site, and R3 and R4 each represent a hydrogen atom or a substituent; wherein at least one of E21 and E22 represents —C(R2)═, wherein R2 represents a linking site; n2 represents an integer of 1 to 4; and * represents a linking site with Y1 in General Formula (1).

[Chemical Formula 9]

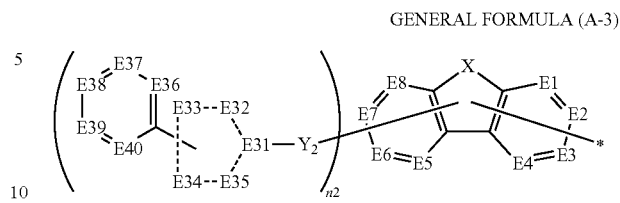

GENERAL FORMULA (A-3)

In General Formula (A-3), X represents —N(R)—, —O—, —S— or —Si(R)(R')—, and E1 to E8 each represent —C(R1)- or —N═, wherein R, R' and R1 each represent a hydrogen atom, a substituent or a linking site with Y1; Y2 represents simply a bond or a divalent linking group; E31 to E35 each represent —C(R2)═, —N═, —O—, —S— or —Si (R3)(R4)-, and E36 to E40 each represent —C(R2)═ or —N═, wherein at least one of E31 to E40 represents —N═, and wherein R2 represents a hydrogen atom, a substituent or a linking site, and R3 and R4 each represent a hydrogen atom or a substituent; wherein at least one of E32 and E33 represents —C(R2)═, wherein R2 represents a linking site; n2 represents an integer of 1 to 4; and * represents a linking site with Y1 in General Formula (1).

[Chemical Formula 10]

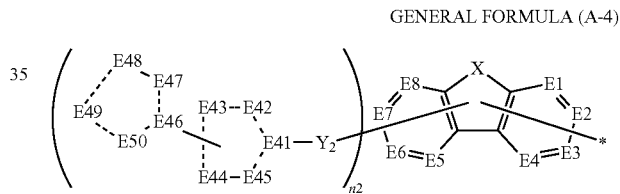

GENERAL FORMULA (A-4)

In General Formula (A-4), X represents —N(R)—, —O—, —S— or —Si(R)(R')—, and E1 to E8 each represent —C(R1)- or —N═, wherein R, R' and R1 each represent a hydrogen atom, a substituent or a linking site with Y1; Y2 represents simply a bond or a divalent linking group; E41 to E50 each represent —C(R2)═, —N═, —O—, —S— or —Si (R3)(R4)-, and E36 to E40 each represent —C(R2)═ or —N═, wherein at least one of E31 to E40 represents —N═, and wherein R2 represents a hydrogen atom, a hydrogen atom, a substituent or a linking site, and R3 and R4 each represent a hydrogen atom or a substituent; wherein at least one of E42 and E43 is represented —C(R2)═, wherein R2 represents a linking site; n2 represents an integer of 1 to 4; and * represents a linking site with Y1 in General Formula (1).

The group represented by any one of General Formulae (A-1) to (A-4) is described below.

The substituents represented by R, R' or R1 in —N(R)— or —Si(R)(R')— represented by X and in —C(R1)═ represented by each of E1 to E8 of the groups represented by any one of General Formulas (A-1) to (A-4) are each synonymous with the substituent represented by Y1 in General Formula (1).

The divalent linking group represented by Y2 of the group represented by any one of General Formulas (A-1) to (A-4) is synonymous with the divalent linking group represented by Y1 in General Formula (1).

The substituent represented by R2 of —C(R2)= represented by each of E11 to E20 in General Formula (A-1), each of E21 to E30 in General Formula (A-2), each of E31 to E40 in General Formula (A-3) or each of E41 to E50 in General Formula (A-4) is synonymous with the substituent represented by Y1 in General Formula (1).

Further preferred compound represented by General Formula (1) will be described below.

Compound Represented by General Formula (2)

Among the compounds represented by General Formula (1) according to the present invention, a compound represented by General Formula (2) is preferable. The compound represented by General Formula (2) will be described below.

[Chemical Formula 11]

GENERAL FORMULA (2)

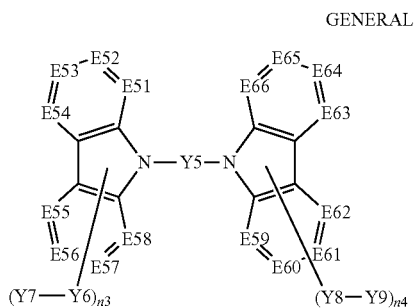

In General Formula (2), Y5 represents a divalent linking group which is an arylene group, a heteroarylene group or a combination of the arylene group and the heteroarylene group; E51 to E66 each represent —C(R3)= or —N=, wherein R3 represents a hydrogen atom or a substituent; Y6 to Y9 each represent a group derived from an aromatic hydrocarbon ring or a group derived from an aromatic heterocycle, wherein at least one of Y6 and Y7 and at least one of Y8 and Y9 each represent a group derived from an aromatic heterocycle containing an N atom; and n3 and n4 each represent an integer of 0 to 4, wherein the sum of n3 and n4 is 2 or more.

The arylene group and heteroarylene group represented by Y5 in General Formula (2) are respectively synonymous with the arylene group and heteroarylene group mentioned as an example of the divalent linking group represented by Y1 in General Formula (1). It is preferred that the divalent linking group which is an arylene group, a heteroarylene group or a combination thereof represented by Y5 contains, among the heteroarylene groups, a group derived from a condensed aromatic heterocycle formed by condensing three or more rings, and further, it is preferred that the group derived from the condensed aromatic heterocycle formed by condensing three or more rings is a group derived from a dibenzofuran ring or a group derived from a dibenzothiophene ring.

The substituent represented by R3 of —C(R3)= represented by each of E51 to E56 in General Formula (2) is synonymous with the substituent represented by Y1 in General Formula (1).

In General Formula (2), it is preferable that as groups represented by E51 to E66, six or more of E51 to E58 and six or more of E59 to E66 are each represented by —C(R3)=.

Examples of aromatic hydrocarbon ring used to form the group derived from an aromatic hydrocarbon ring represented by each of Y6 to Y9 in General Formula (2) include a benzene ring, a biphenyl ring, a naphthalene ring, an azulene ring, an anthracene ring, a phenanthrene ring, a pyrene ring, a chrysene ring, a naphthacene ring, a triphenylene ring, an o-terphenyl ring, an m-terphenyl ring, a p-terphenyl ring, an acenaphthene ring, a coronene ring, a fluorene ring, a fluoranthrene ring, a naphthacene ring, a pentacene ring, a perylene ring, a pentaphene ring, a picene ring, a pyrene ring, a pyranthrene ring, an anthranthrene ring and the like.

The aromatic hydrocarbon ring may have a substituent represented by Y1 in General Formula (1).

Examples of aromatic heterocycle used to form the group derived from an aromatic heterocycle represented by each of Y6 to Y9 include a furan ring, a thiophene ring, an ozazole ring, a pyrrole ring, a pyridine ring, a pyridazine ring, a pyrimidine ring, a pyrazine ring, a triazine ring, a benzimidazole ring, an oxadiazole ring, a triazole ring, an imidazole ring, a pyrazole ring, a triazole ring, an indole ring, an indazole ring, a benzimidazole ring, a benzothiazole ring, a benzoxazole ring, a quinoxaline ring, a quinazoline ring, a cinnoline ring, a quinoline ring, an isoquinoline ring, a phthalazine ring naphthylidine ring, a carbazole ring, a carboline ring, a diazacarbazole ring (which is a ring formed by further substituting one of carbon atoms constituting a carboline ring with a nitrogen atom) and the like.

The aromatic heterocycle may have a substituent represented by Y1 in General Formula (1).

Examples of aromatic heterocycle containing an N atom used to form a group derived from an aromatic heterocycle containing an N atom represented by each at at least one of Y6 and Y7 and at least one of Y8 and Y9 in General Formula (2) include an oxazole ring, a pyrrole ring, a pyridine ring, a pyridazine ring, a pyrimidine ring, a pyrazine ring, a triazine ring, a benzimidazole ring, an ozadiazole ring, a triazole ring, an imidazole ring, a pyrazole ring, a triazole ring, an indole ring, an indazole ring, a benzimidazole ring, a benzothiazole ring, a benzoxazole ring, a quinozaline ring, a quinazoline ring, a cinnoline ring, a quinoline ring, an isoquinoline ring, a phthalazine ring, a naphthylidine ring, a carbazole ring, a caboline ring, a diazacarbazole ring (which is a ring formed by further substituting one of carbon atoms constituting a carboline ring with a nitrogen, atom) and the like.

In General Formula (2), it is preferred that the groups represented by Y7 and Y9 are each a group derived from a pyridine ring.

In General Formula (2), it is preferred that the groups represented by Y6 and Y8 are each a group derived from a benzene ring.

Among the compounds represented by General Formula (2) according to the present invention, a further preferred compound will be described below.

Compound Represented by General Formula (3)

Among the compounds represented by General Formula (2), a compound represented by General Formula (3) is preferable. The compound represented by General Formula (3) will be described below.

[Chemical Formula 12]

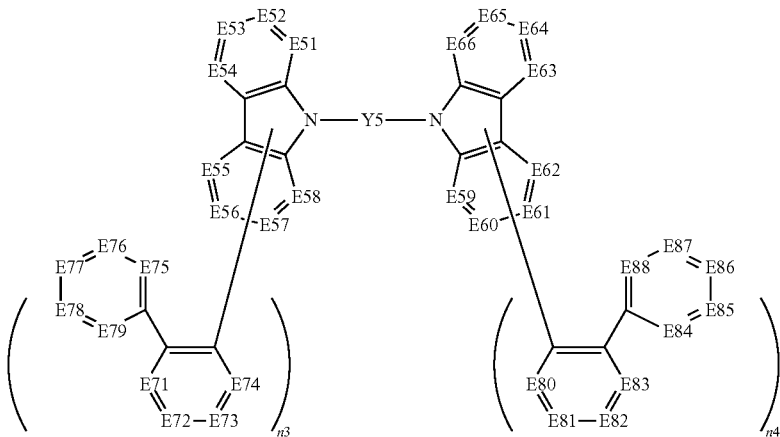

GENERAL FORMULA (3)

In General Formula (3), Y5 represents a divalent linking group which is an arylene group, a heteroarylene group or a combination of the arylene group and the heteroarylene group; E51 to E66 and E71 to E88 each represent —C(R3)= or —N=, wherein R3 represents a hydrogen atom or a substituent, and wherein at least one of E71 to E79 and at least one of E80 to E88 each represent —N=; and n3 and n4 each represent an integer of 0 to 4, wherein the sum of n3 and n4 is 2 or more.

The arylene group and heteroarylene group represented by Y5 in General Formula (3) are respectively synonymous with the arylene group and heteroarylene group mentioned as an example or the divalent linking group represented by Y1 in General Formula (1).

It is preferred that the divalent linking group which is an arylene group, a heteroarylene group or a combination thereof represented by Y5 contains, among the heteroarylene groups, a group derived from a condensed aromatic heterocycle formed by condensing three or more rings, and further, it is preferred that the group derived from the condensed aromatic heterocycle formed by condensing three or more rings is a group derived from a dibenzofuran ring or a group derived from a dibenzothiophene ring.

The substituent represented by R3 of —C(R3)= represented by each of E51 to E66 and E71 to E78 in General Formula (3) is synonymous with the substituent represented by Y1 in General Formula (1).

In General Formula (3), it is preferable that six or more of E51 to E58 and six or more of E59 to E66 are each represented by —C(R3)=.

In General Formula (3), it is preferable that at least one of E75 to E79 and at least one of E84 to E88 each represent —N=.

Further, in General Formula (3), it is preferable that one of E75 to E79 and one of E84 to E88 each represent —N=.

Further, in General Formula (3), it is preferable that E71 to E74 and E80 to E84 are each represented by —C(R3)=.

Further, in the compound represented by General Formula (2) or General Formula (3), it is preferred that E53 is represented by —C(R3)=, wherein R3 represents a liking site; and further, it is preferred that E61 is also represented by —C(R3)=, wherein R3 represents a liking site.

Furthermore, it is preferred that E75 and E84 are each represented by —N=, and E71 to E74 and E80 to E83 are each represented by —C(R3)=.

Concrete examples of the compound represented by General Formula (1), (2) or (3) of the present invention will be described bellow; however, the present invention is not limited thereto.

[Chemical Formula 13]

1

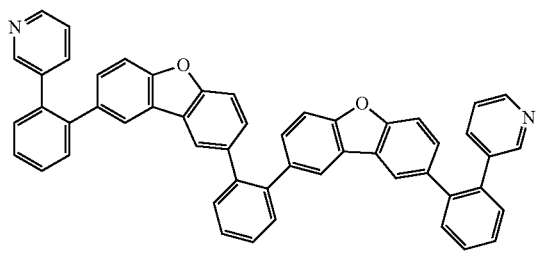

2

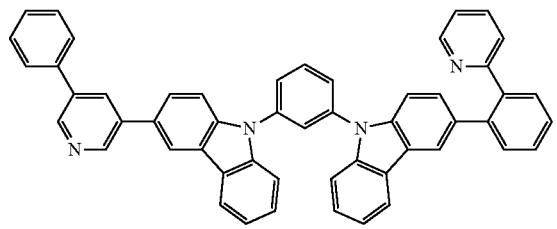

-continued
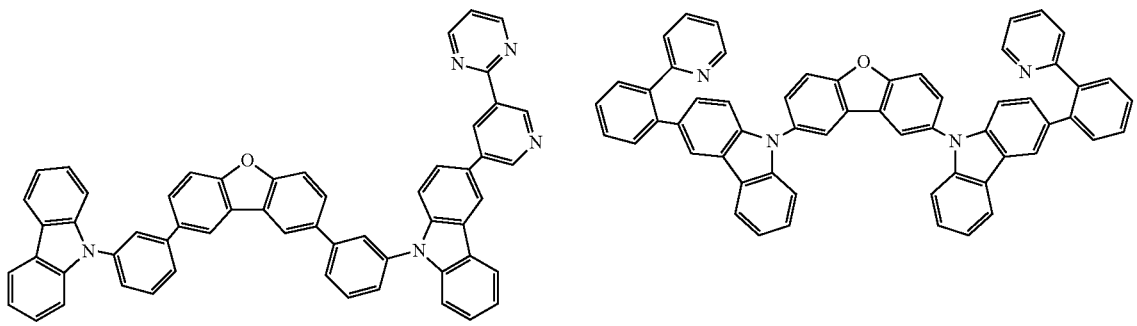
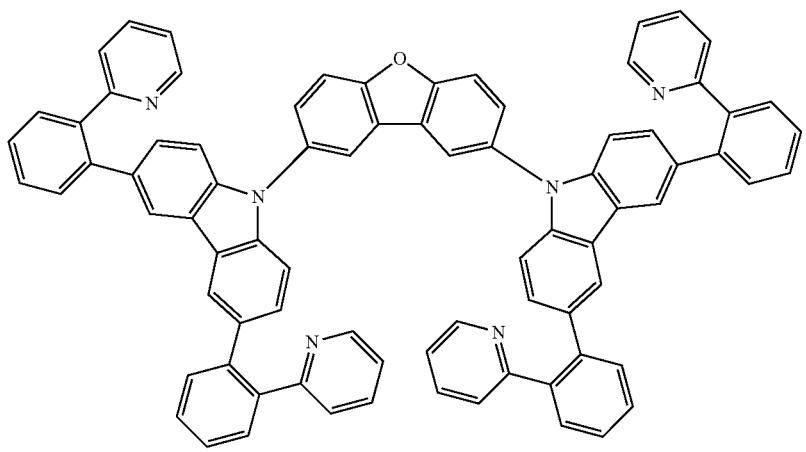
[Chemical Formula 14]
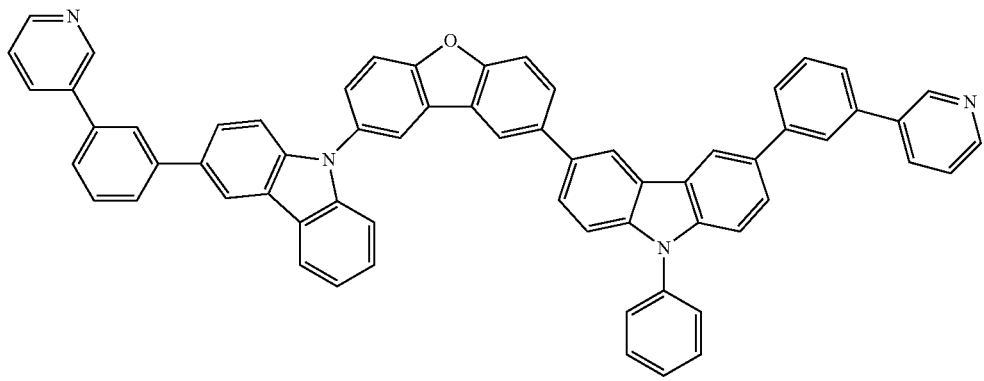
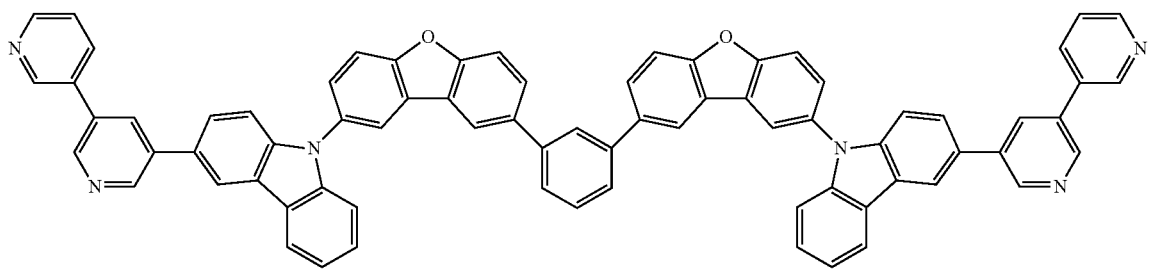

-continued
8
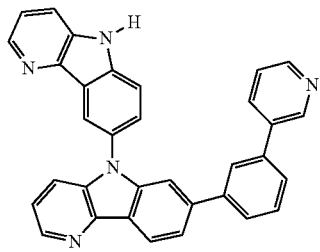
9
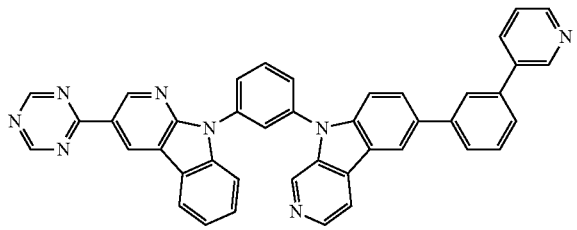
[Chemical Formula 15]
10
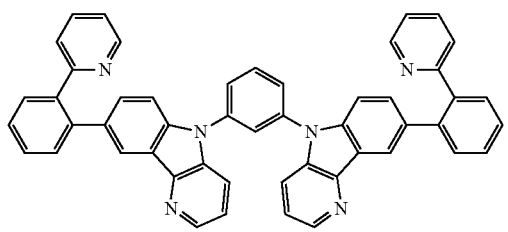
11
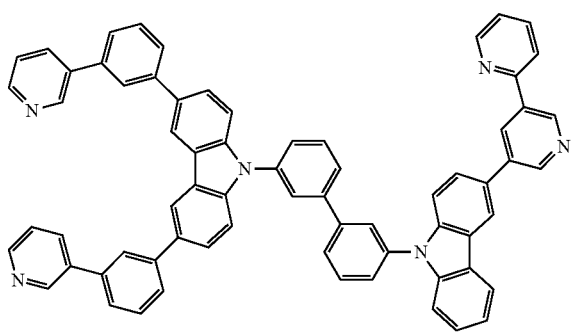
12
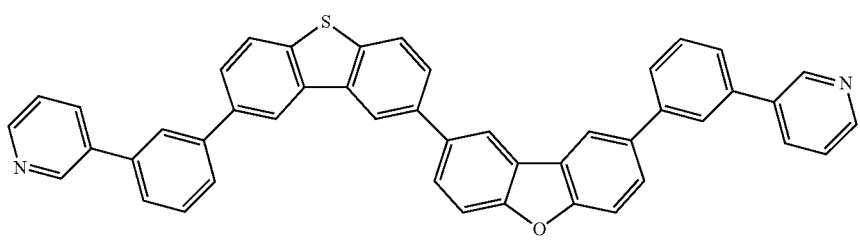
13
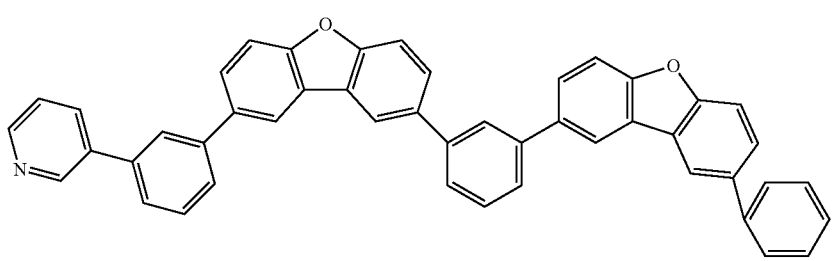
14
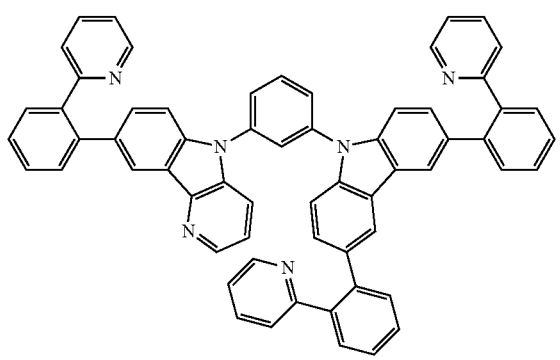
15
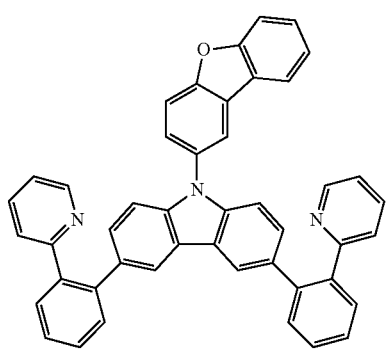

[Chemical Formula 16]
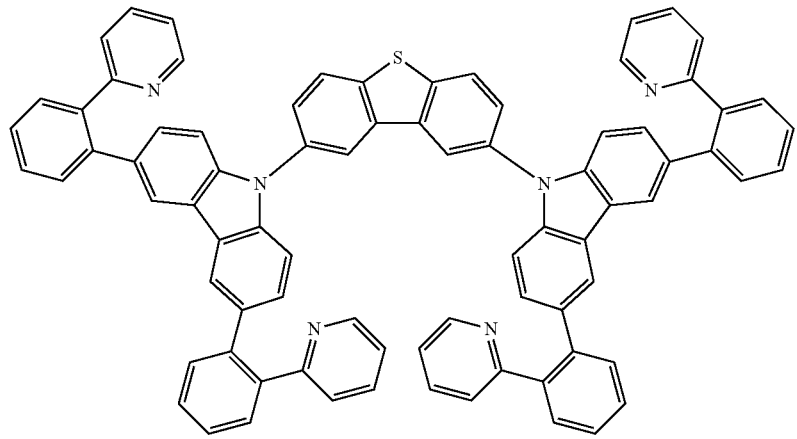
16
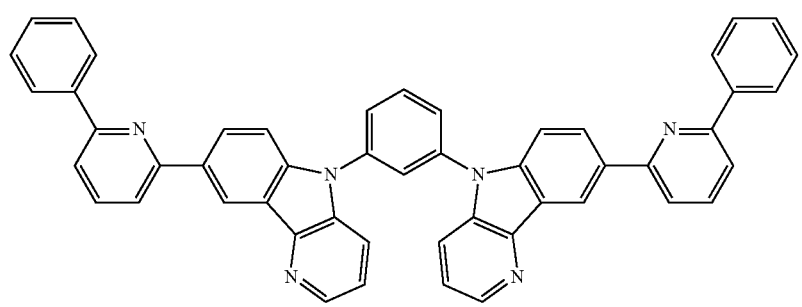
17
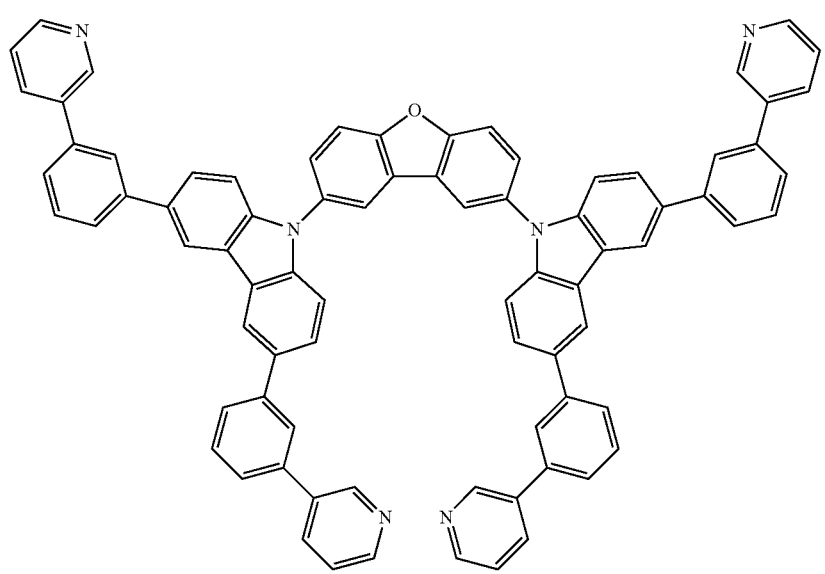
18

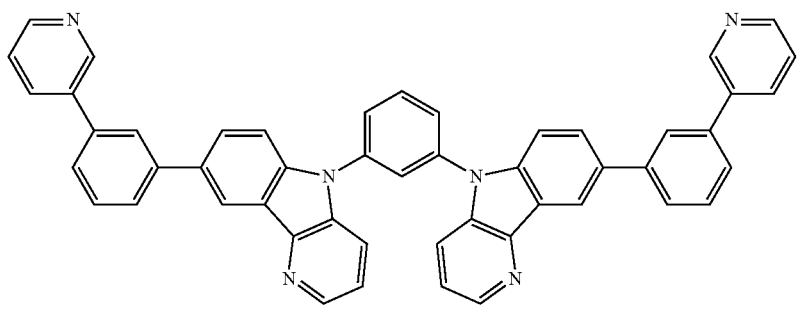
19
[Chemical Formula 17]
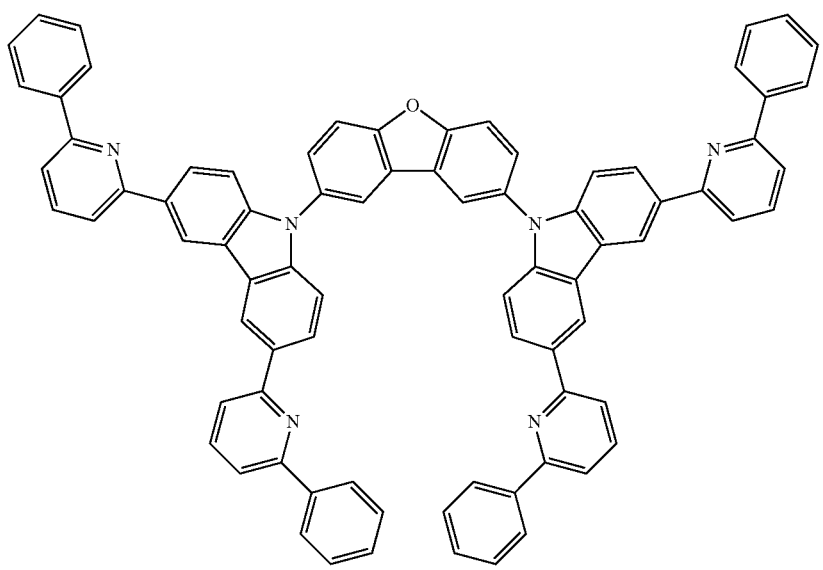
20
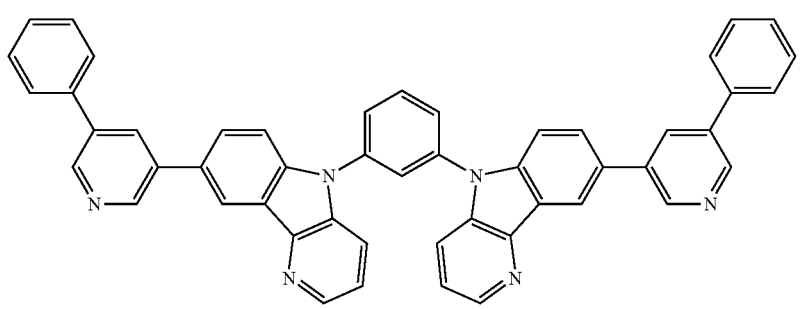
21
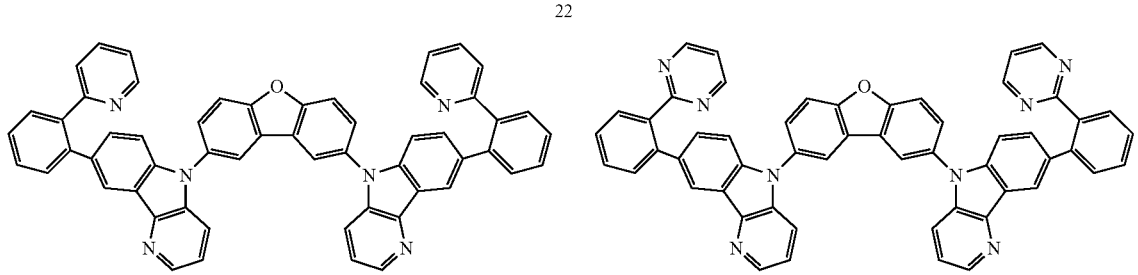
22    23

[Chemical Formula 18]
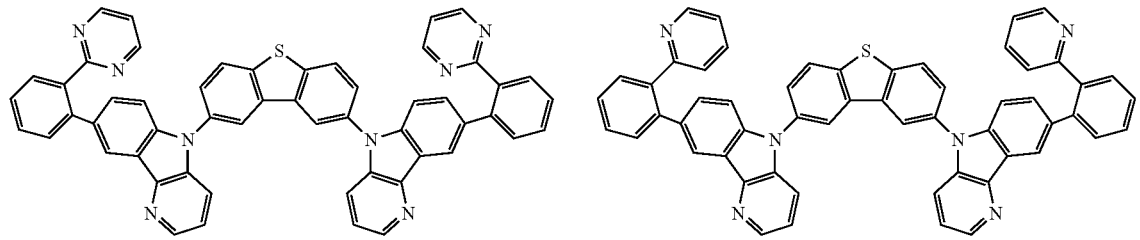
24
25
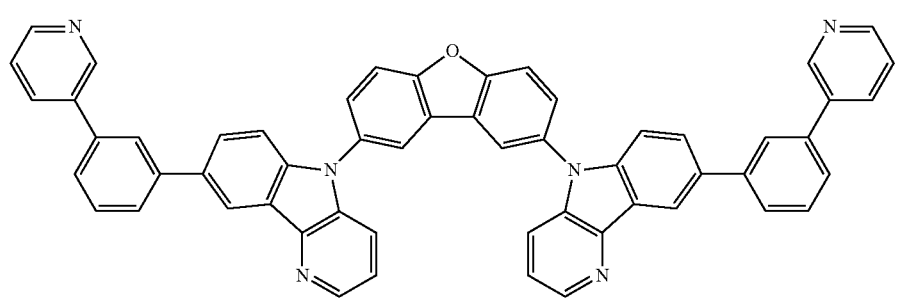
26
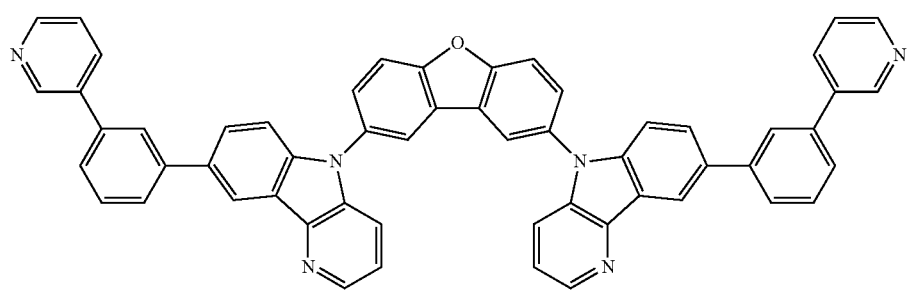
27
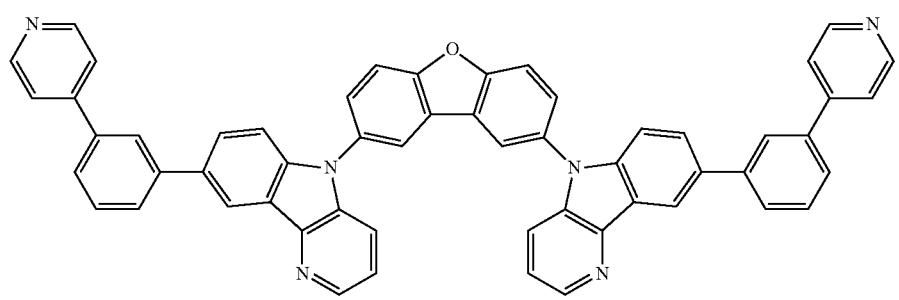
28
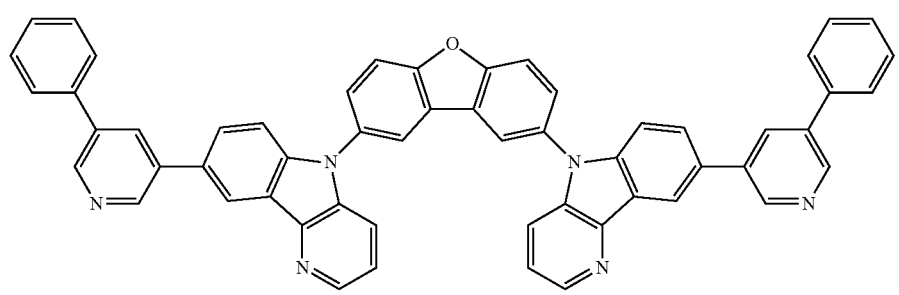
29

-continued
[Chemical Formula 19]
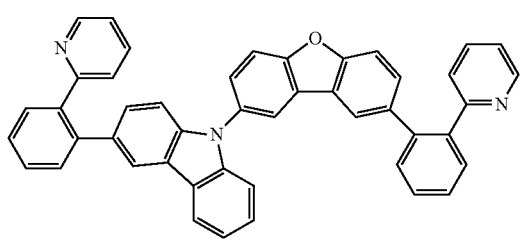
30
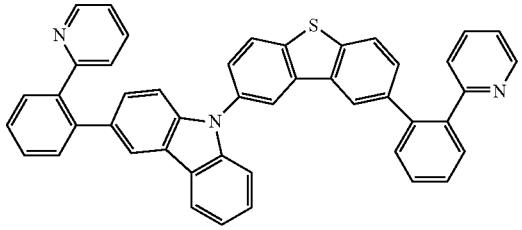
31
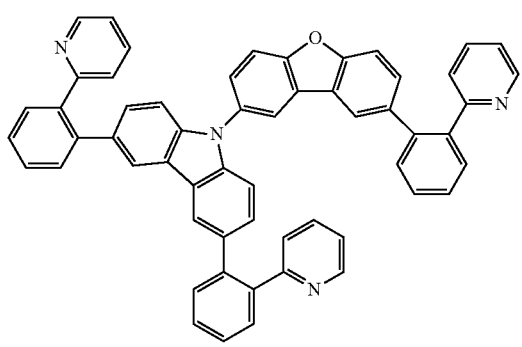
32
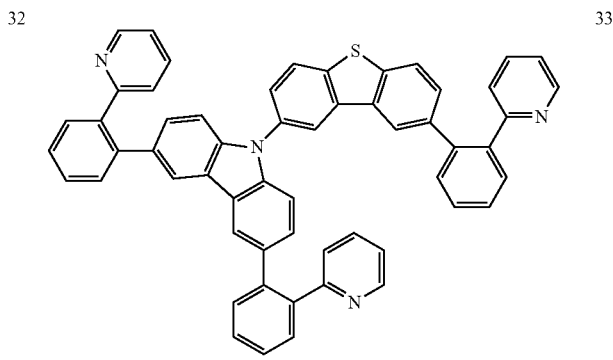
33
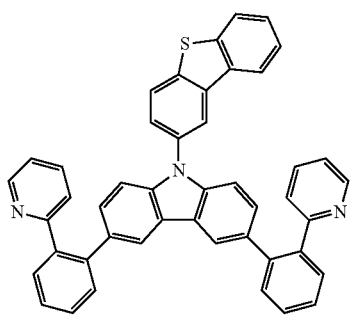
34
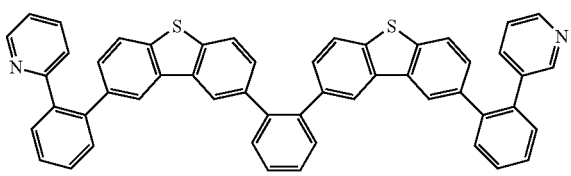
35
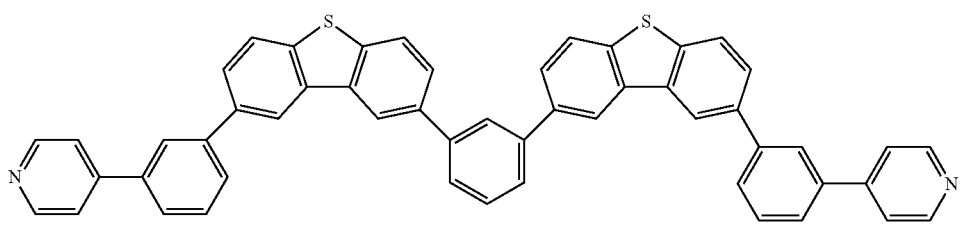
36
[Chemical Formula 20]
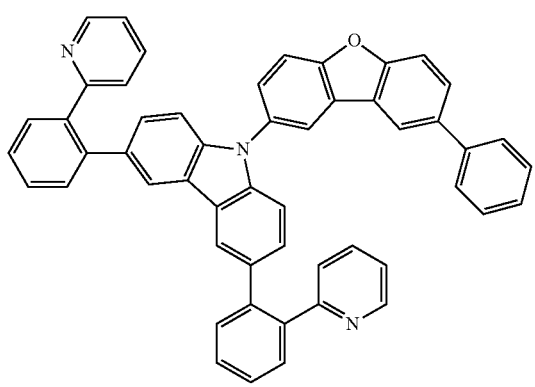
37
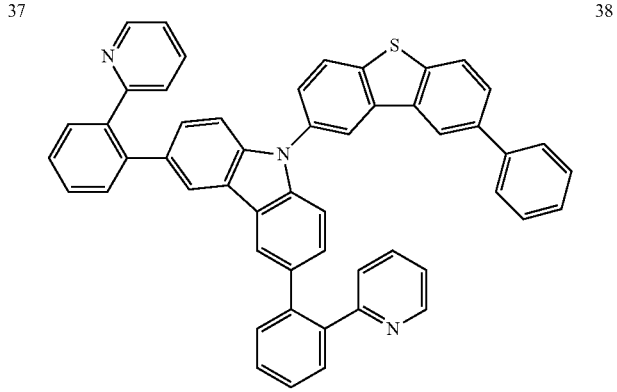
38

-continued
39
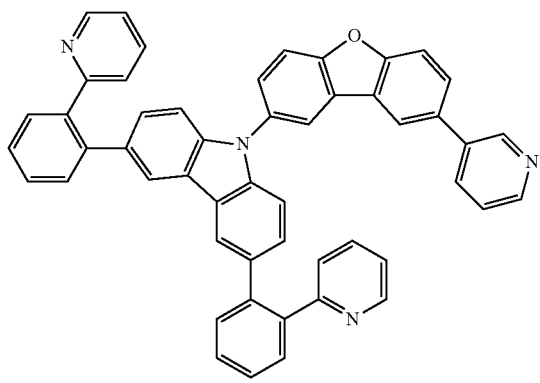
40
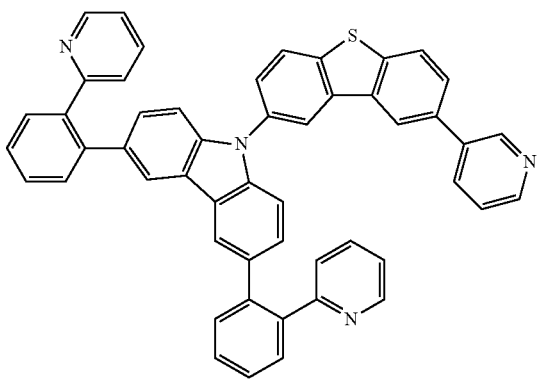
41
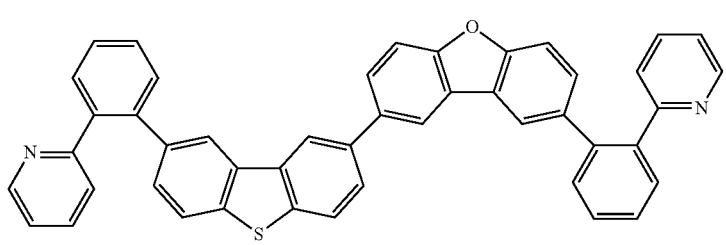
42
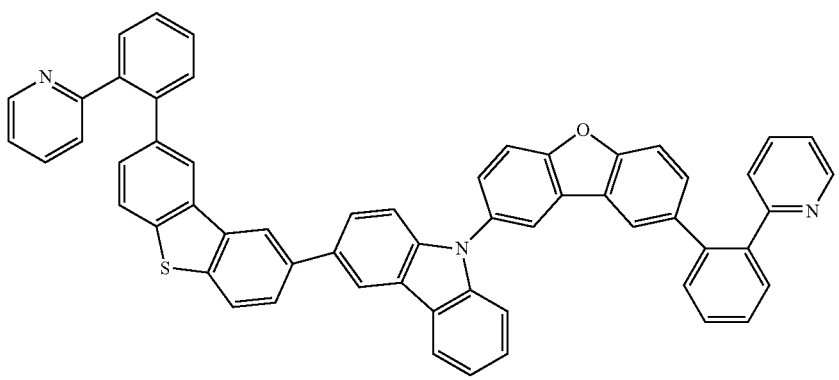
[Chemical Formula 21]
43
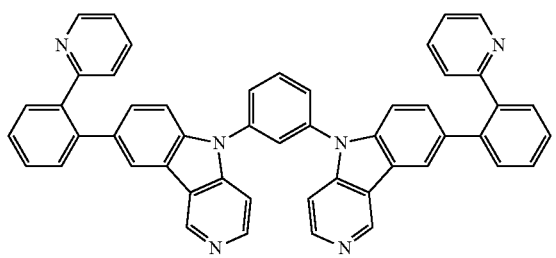
44
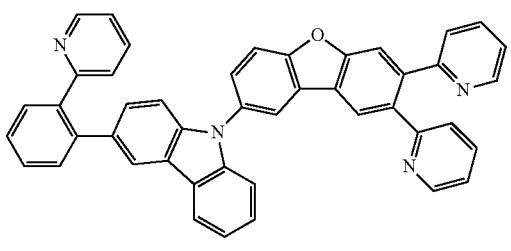

-continued
45
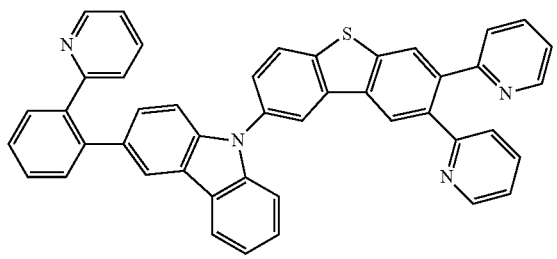
46
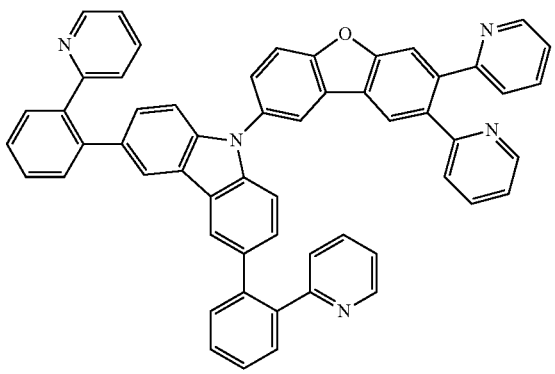
47
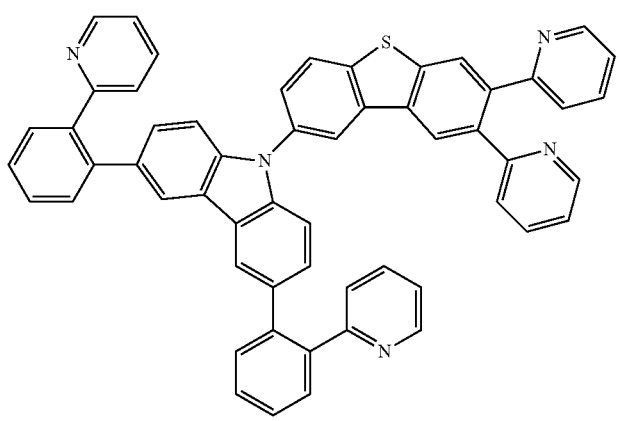
[Chemical Formula 22]
48
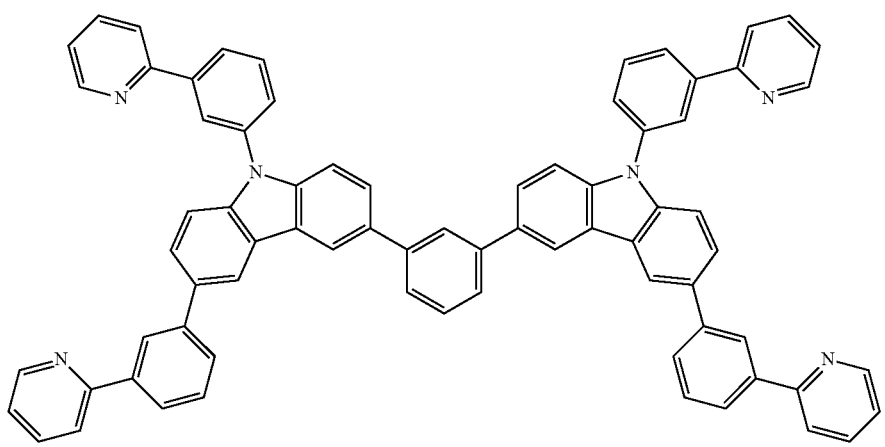
49
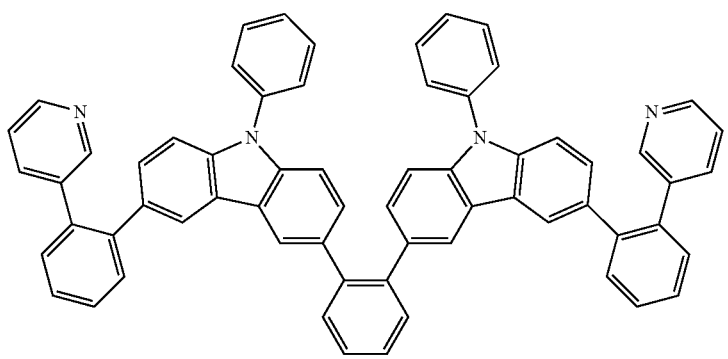

-continued
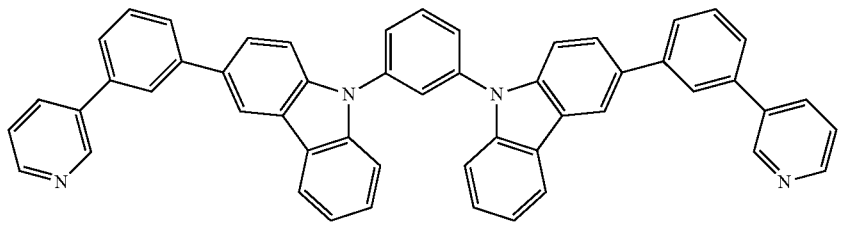
50
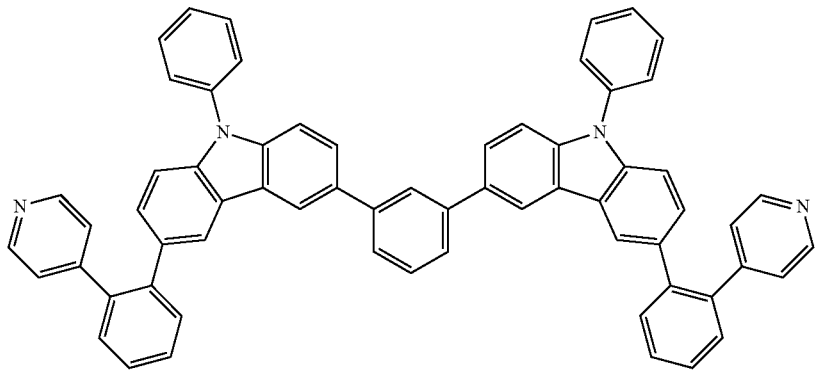
51
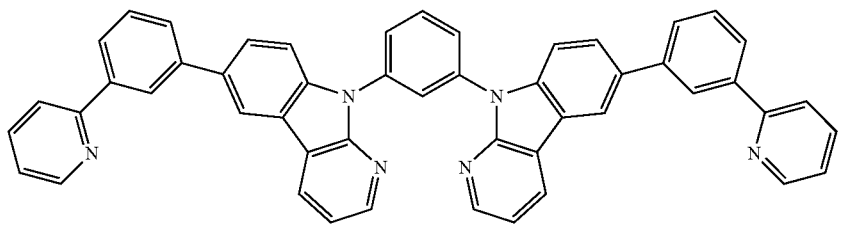
52
[Chemical Formula 23]
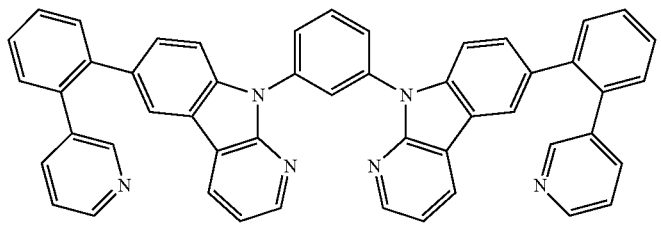
53
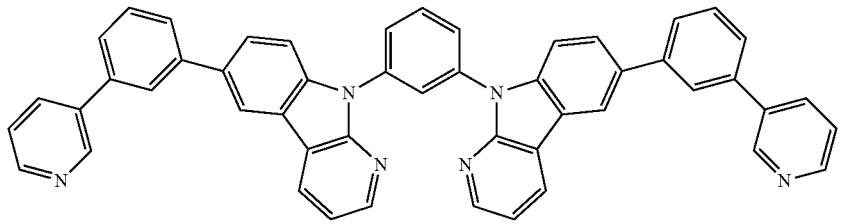
54
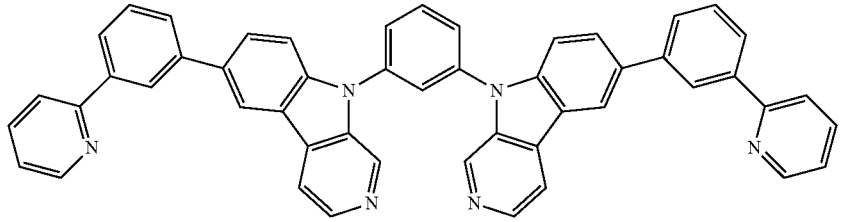
55

-continued
56
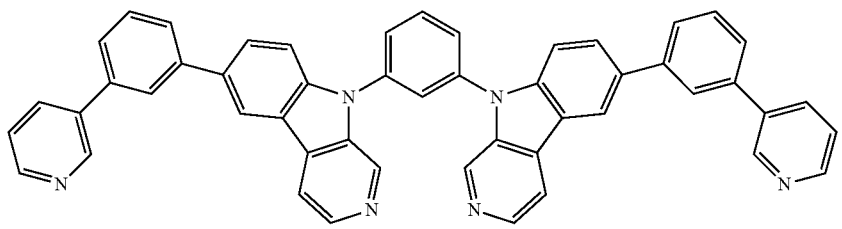
57
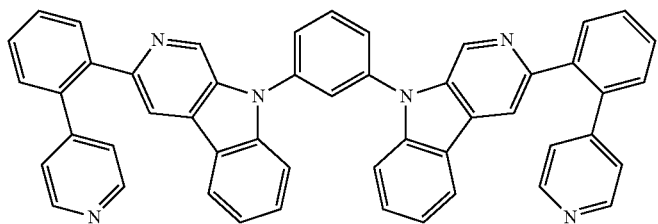
58
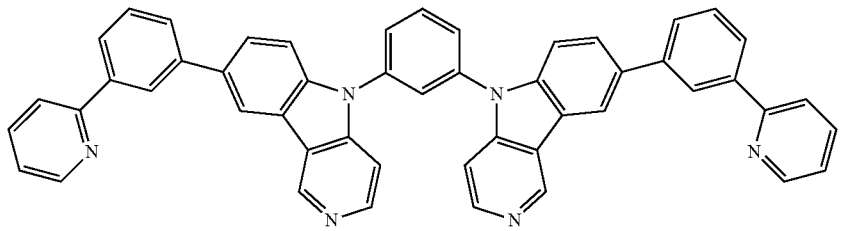
[Chemical Formula 24]
59 60
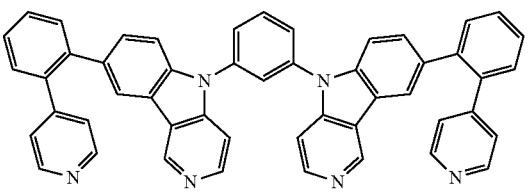
61
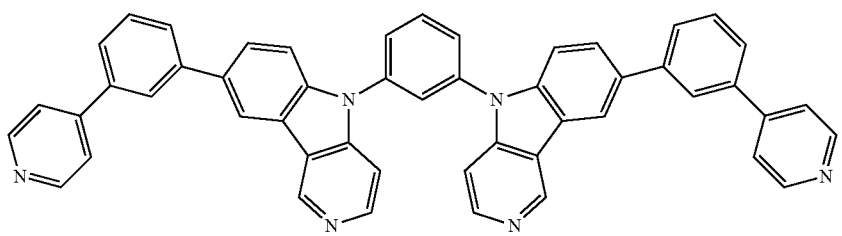
62
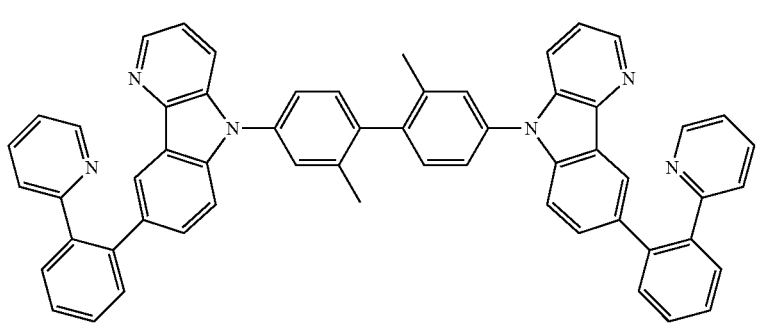

-continued
63
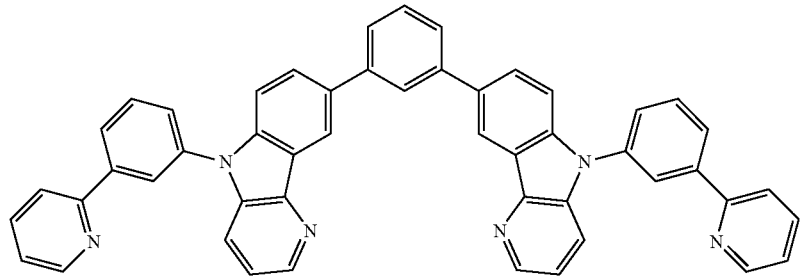
64
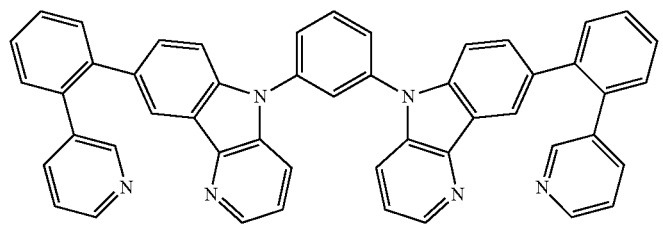
[Chemical Formula 25]
65
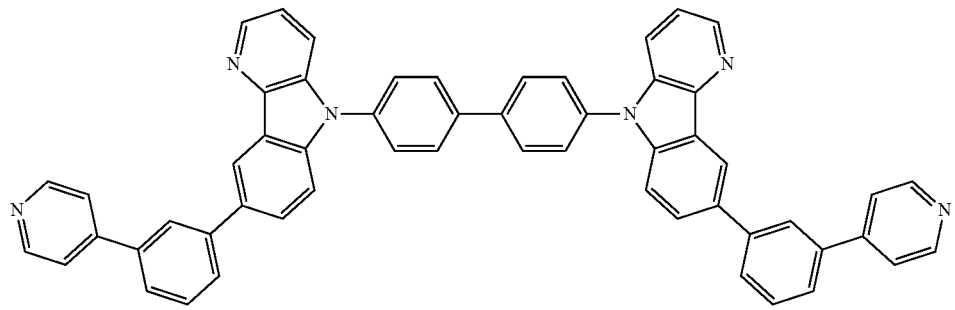
66
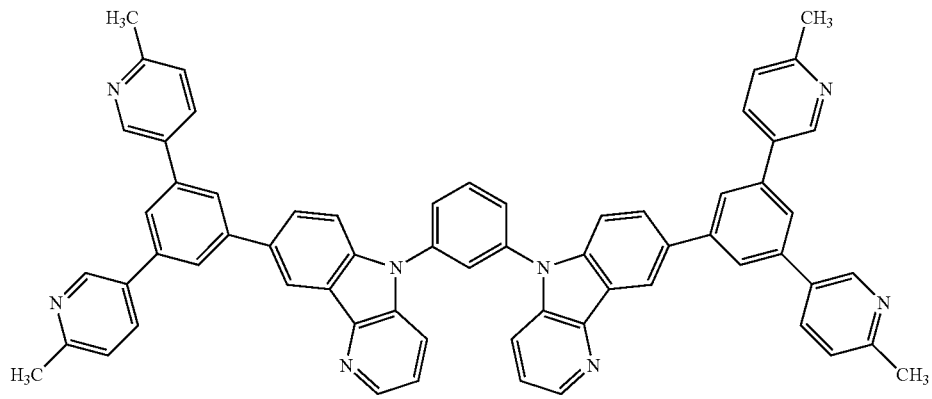

-continued
67
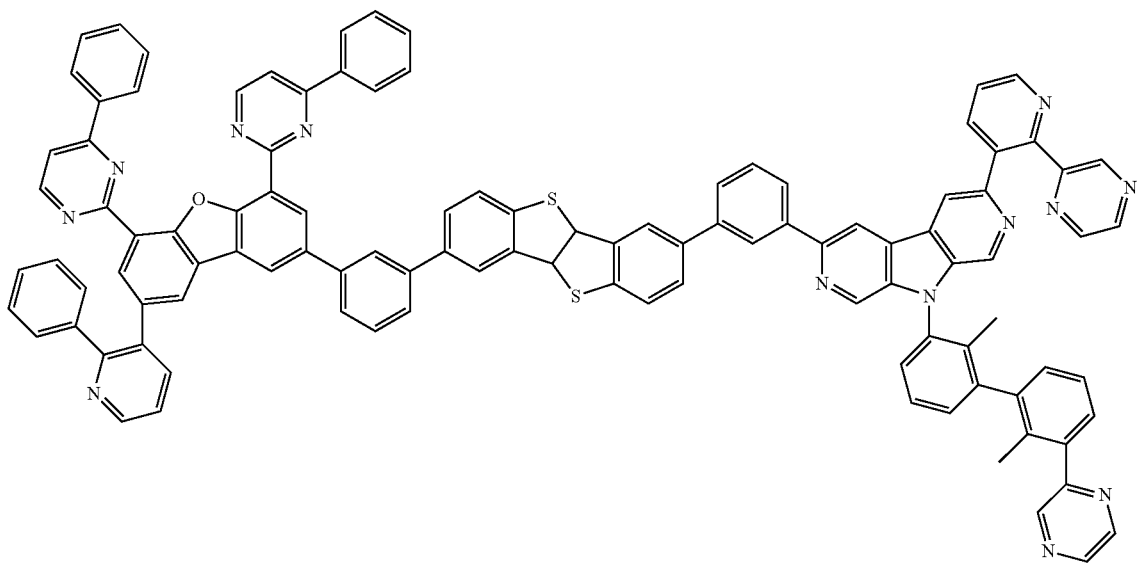
[Chemical Formula 26]
68
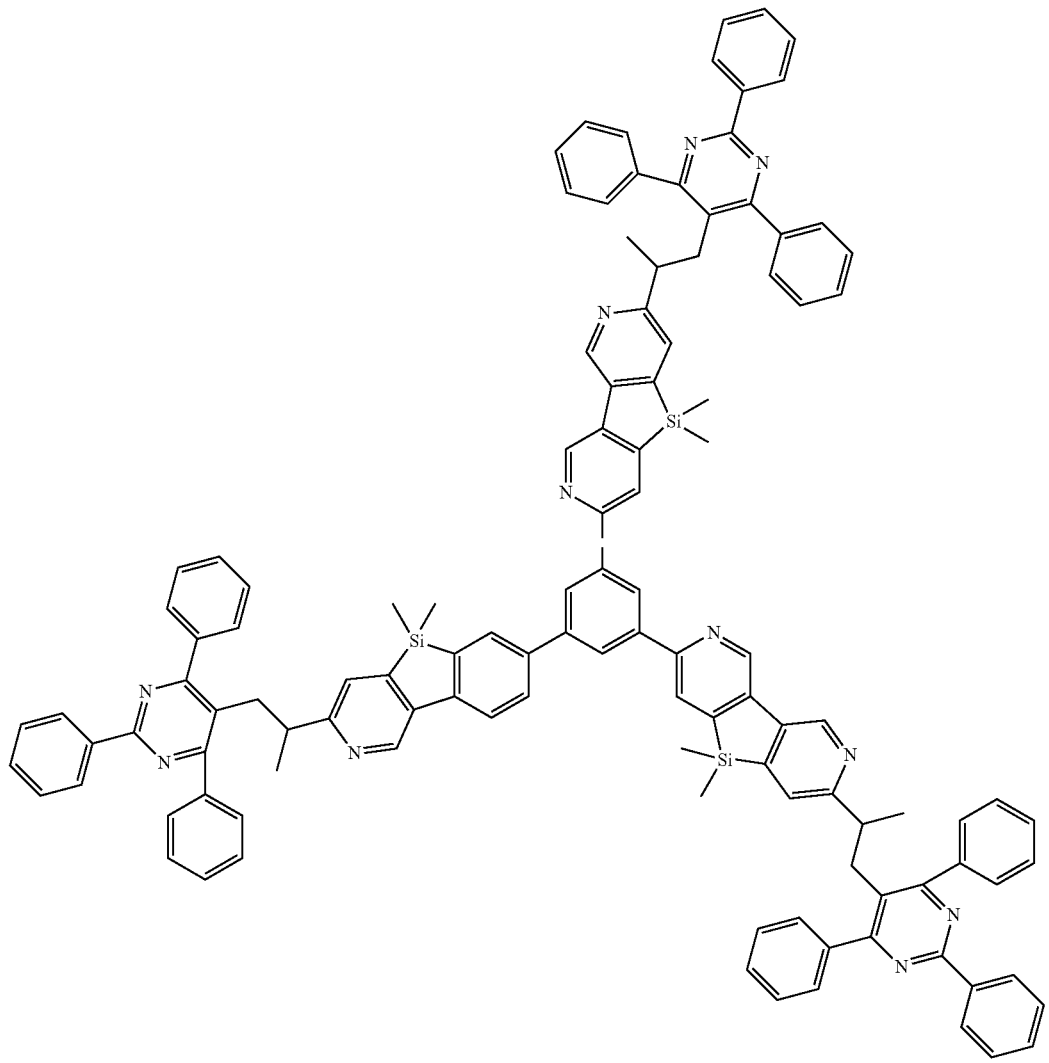

-continued
69
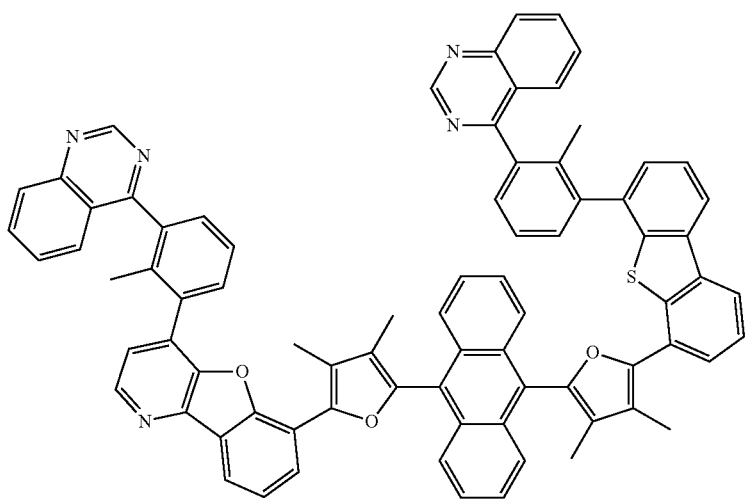
[Chemical Formula 27]
70
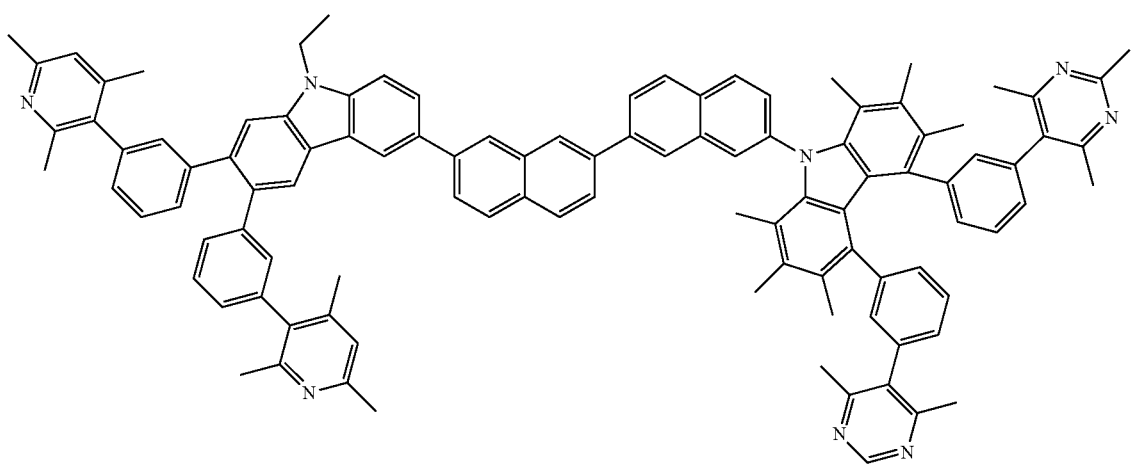
71
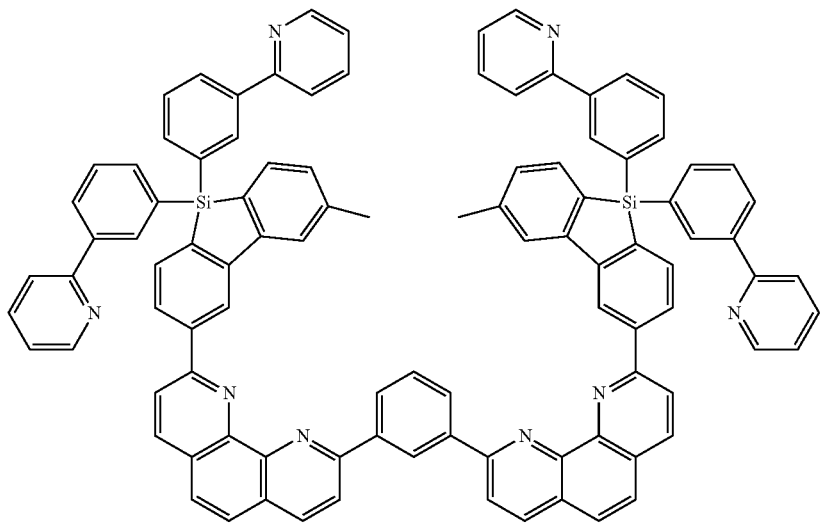

-continued
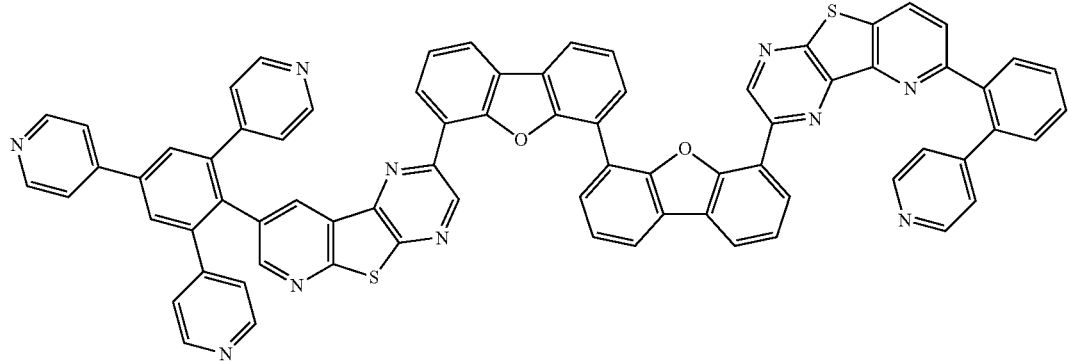
72
[Chemical Formula 28]
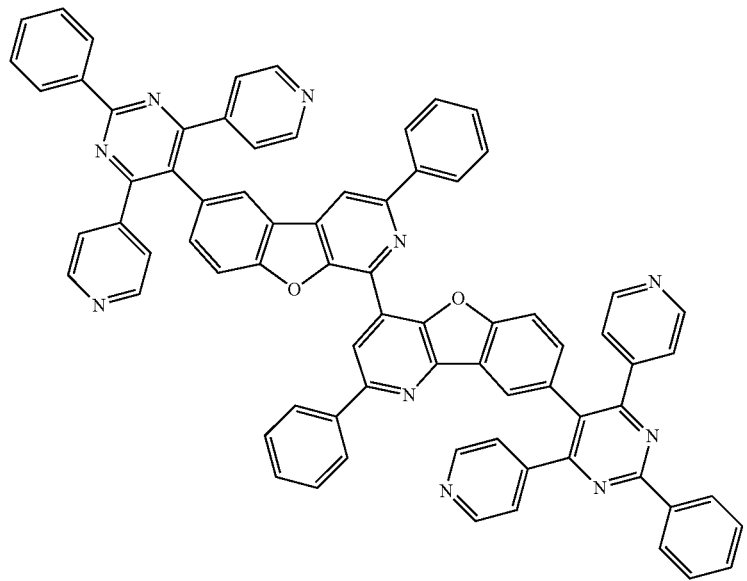
73
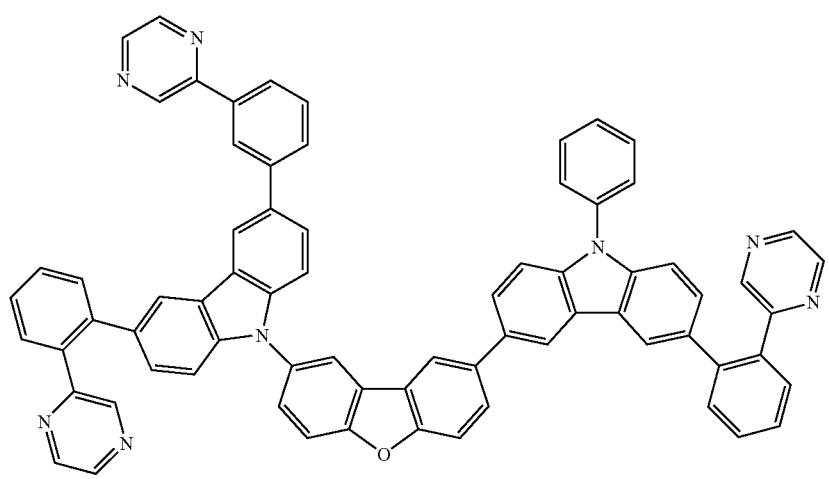
74

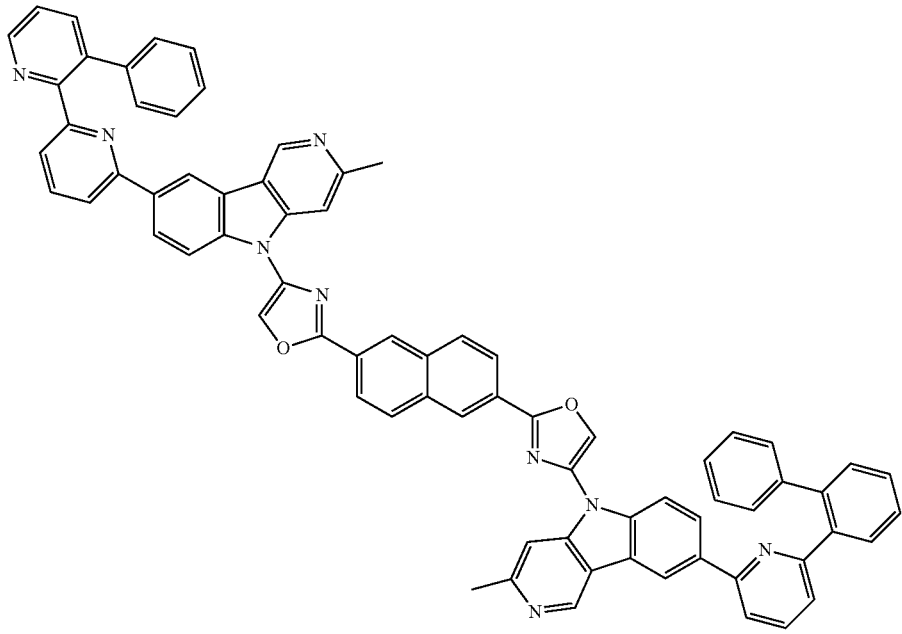
[Chemical Formula 29]
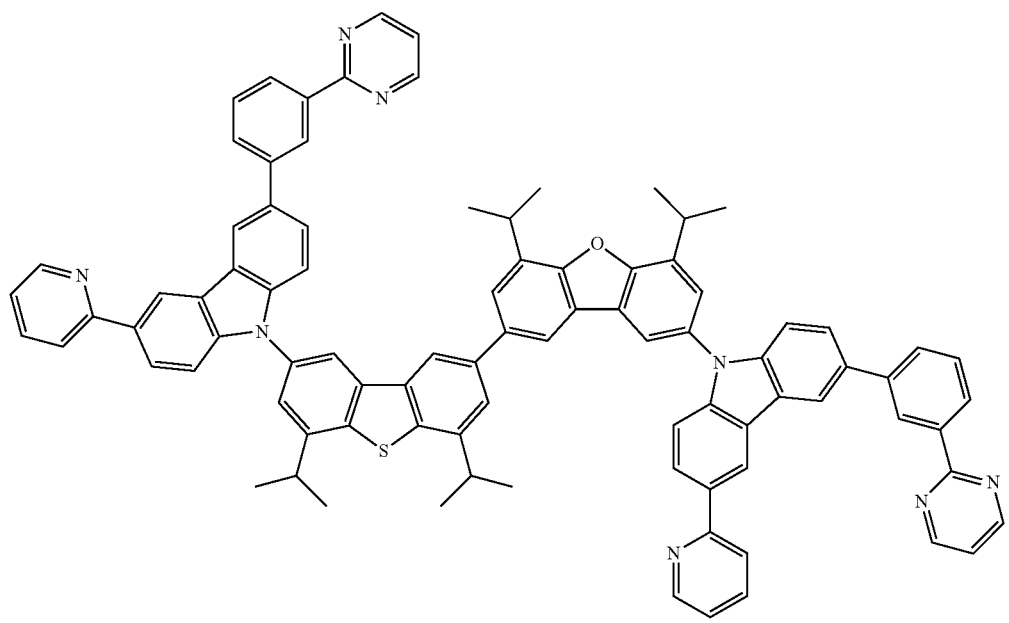

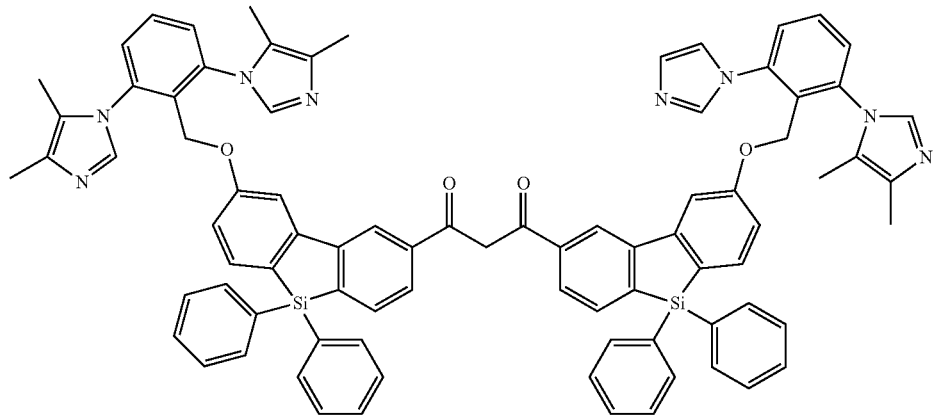
77
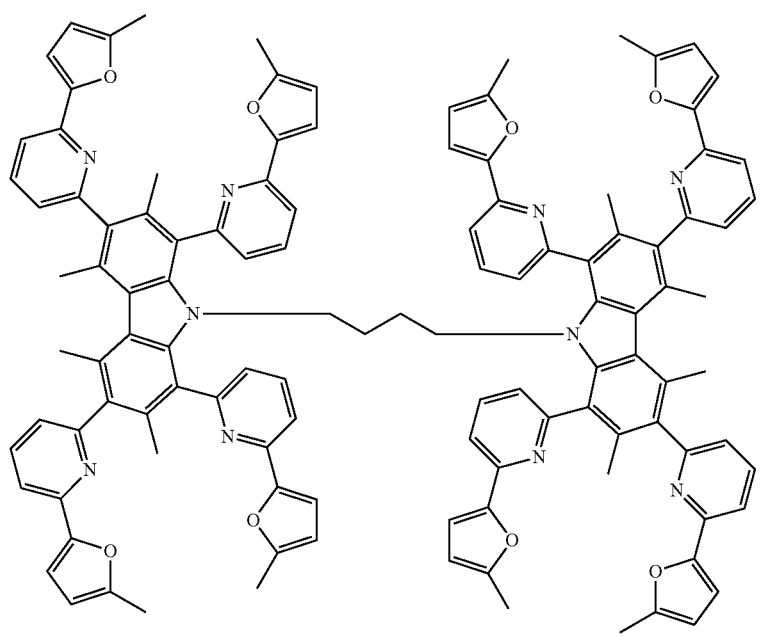
78

[Chemical Formula 30]
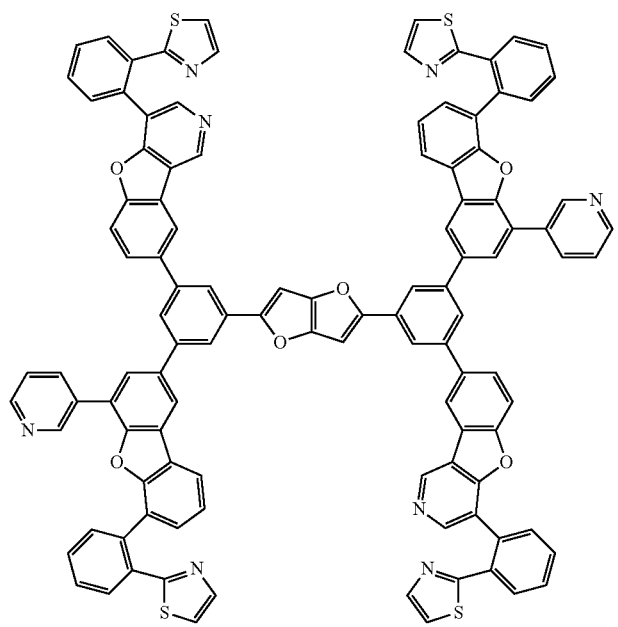
79
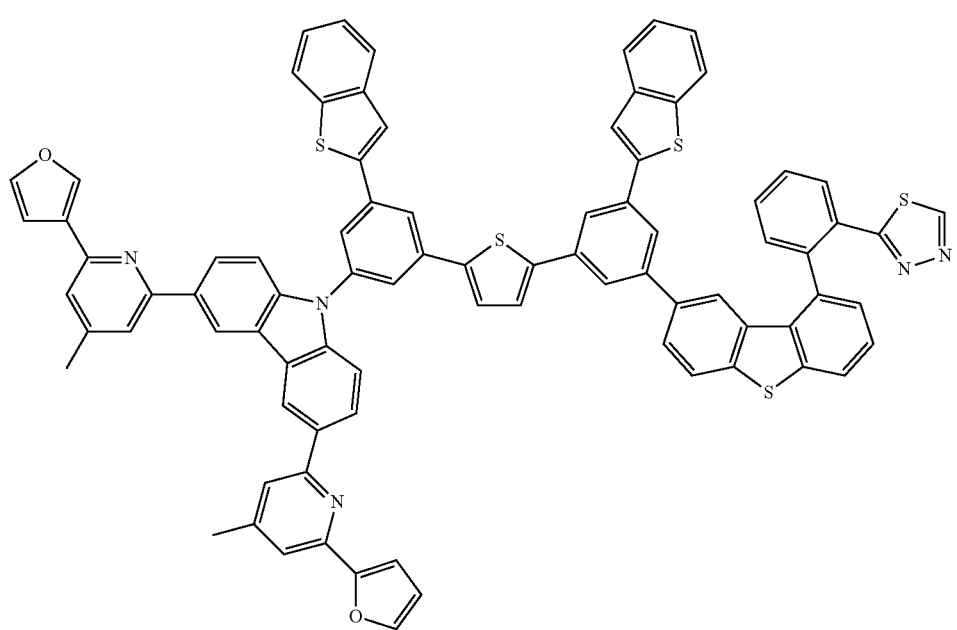
80

[Chemical Formula 31]
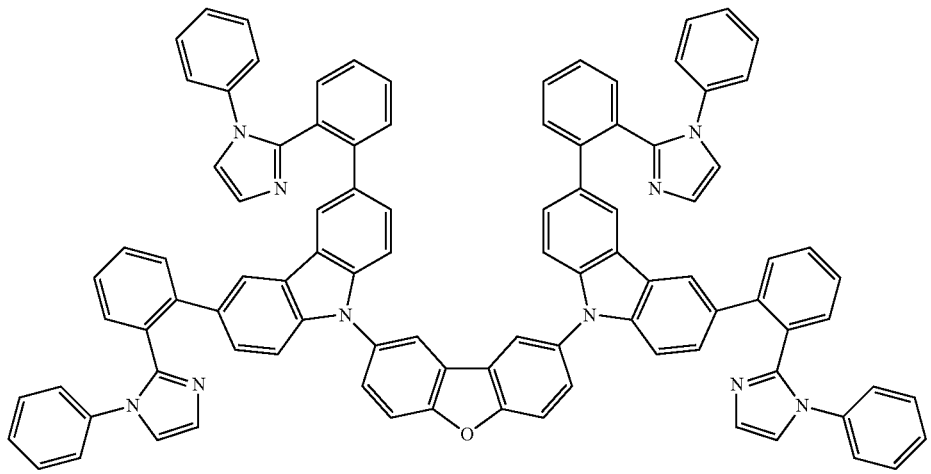
81
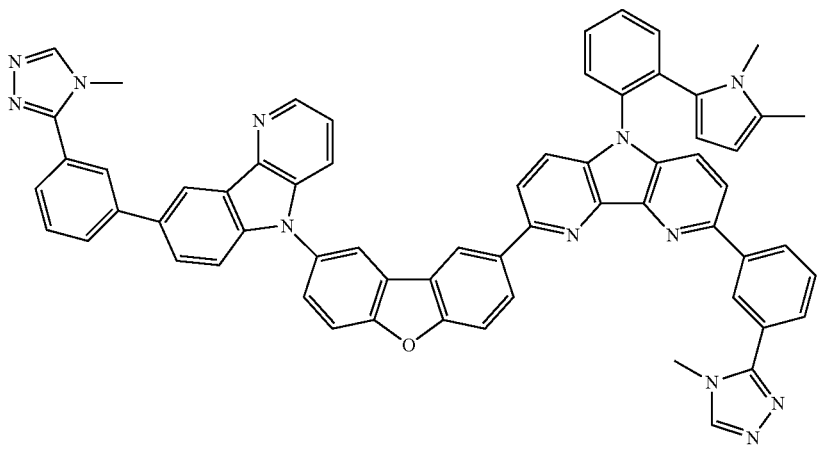
82
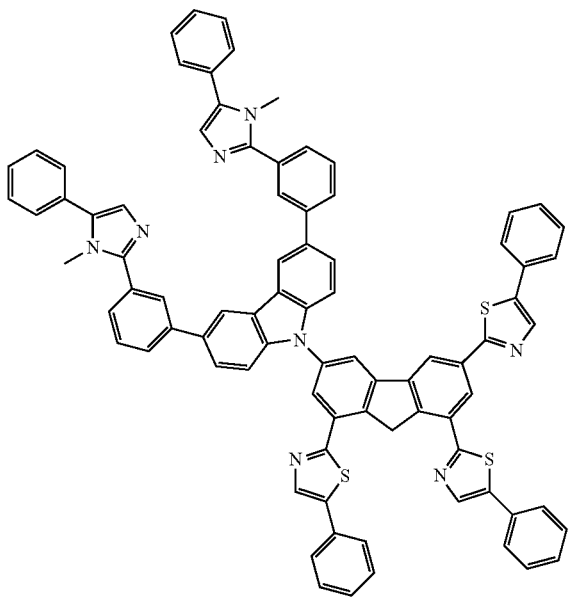
83

[Chemical Formula 32]
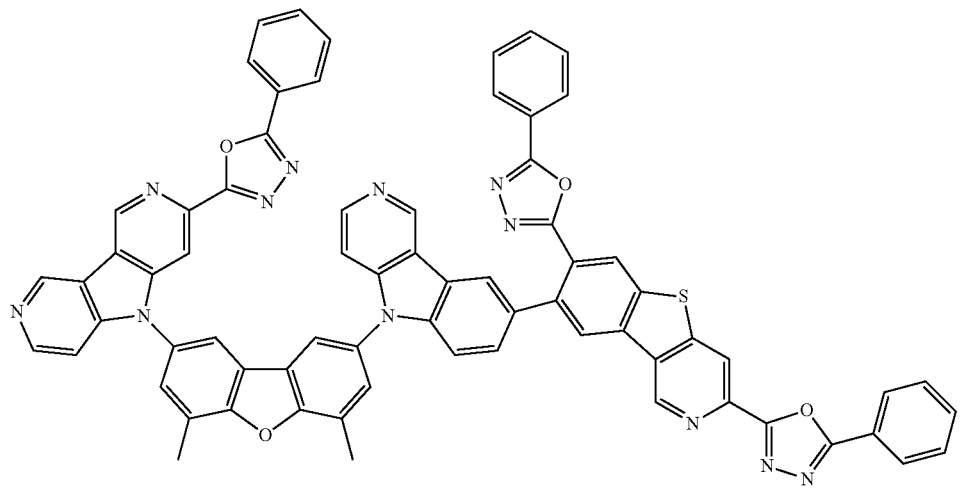
84
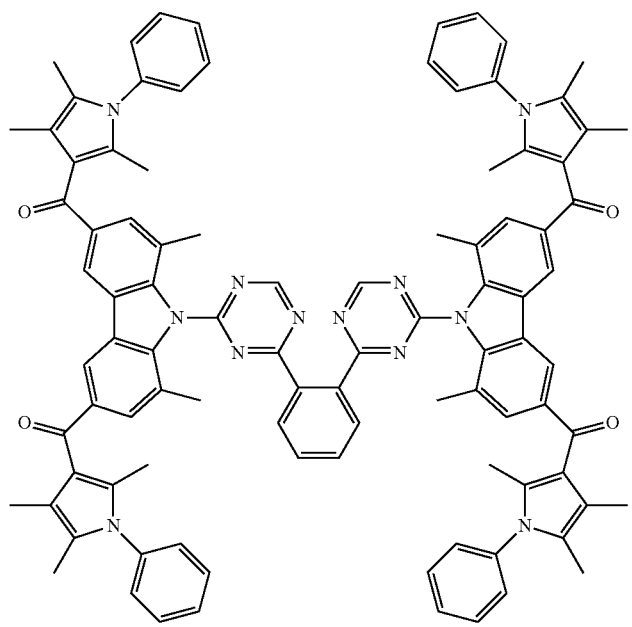
85

[Chemical Formula 33]
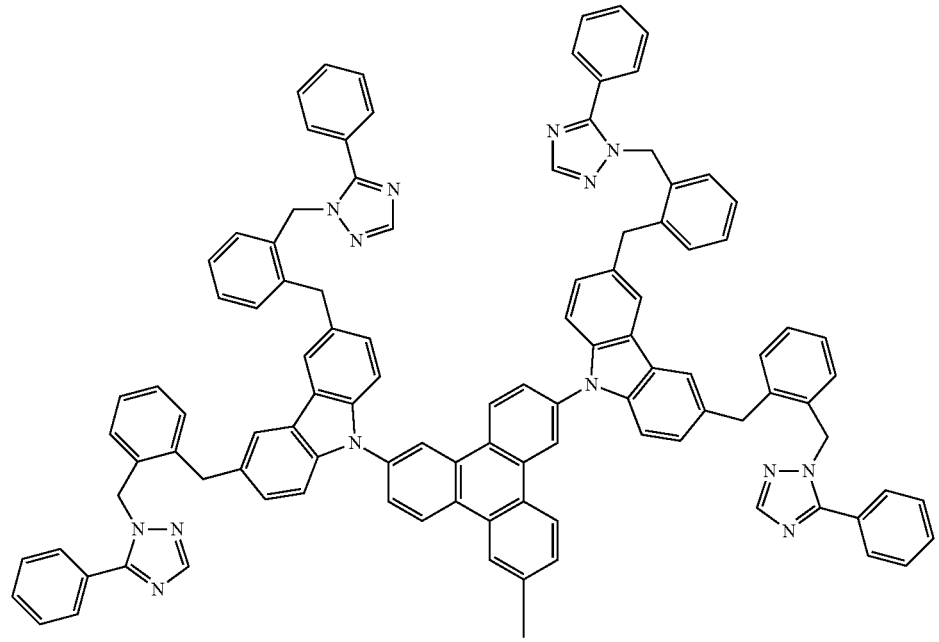
86
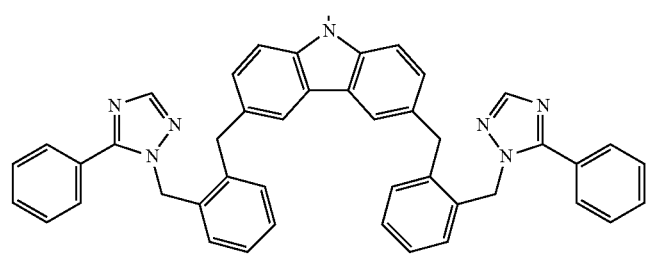
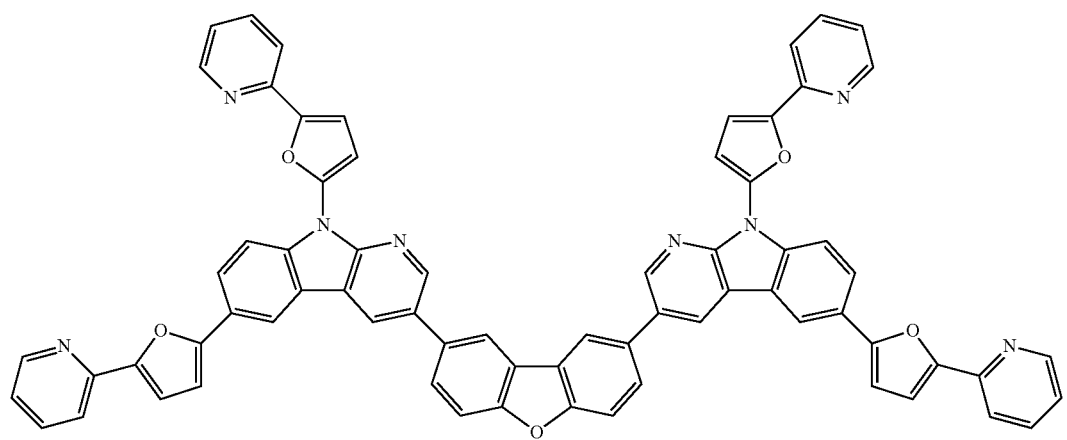
87

88
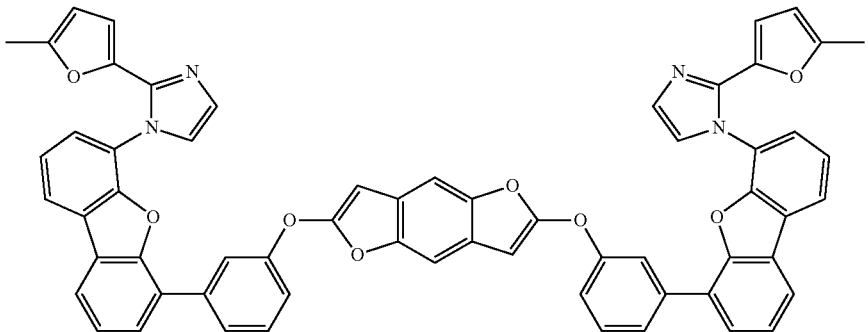
[Chemical Formula 34]
89
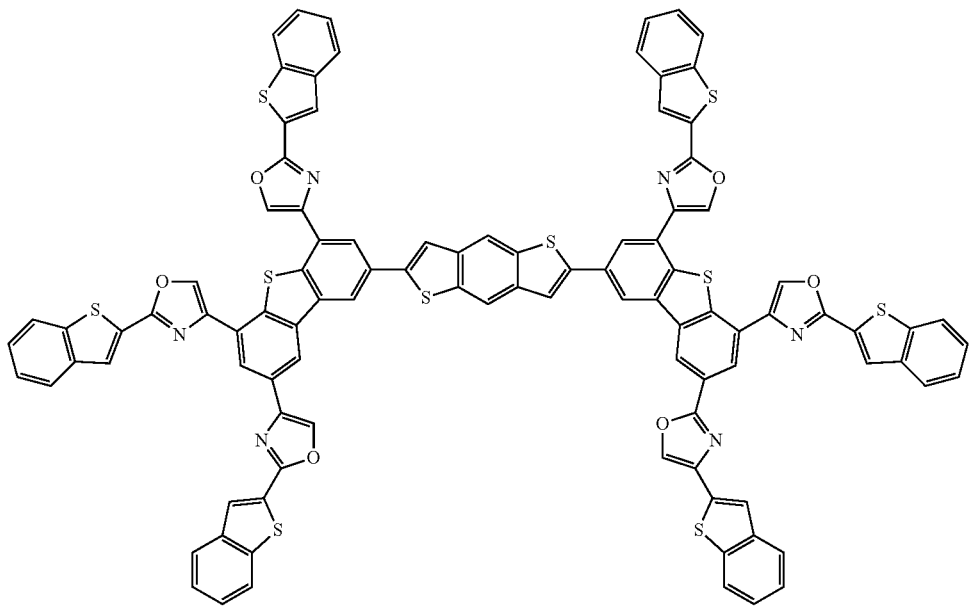
90 91
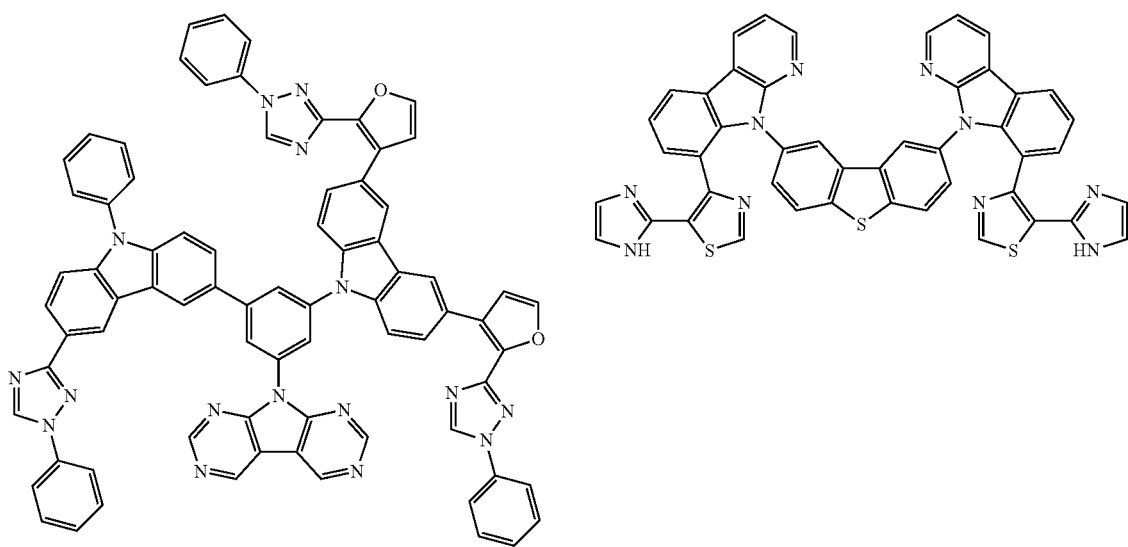

[Chemical Formula 35]
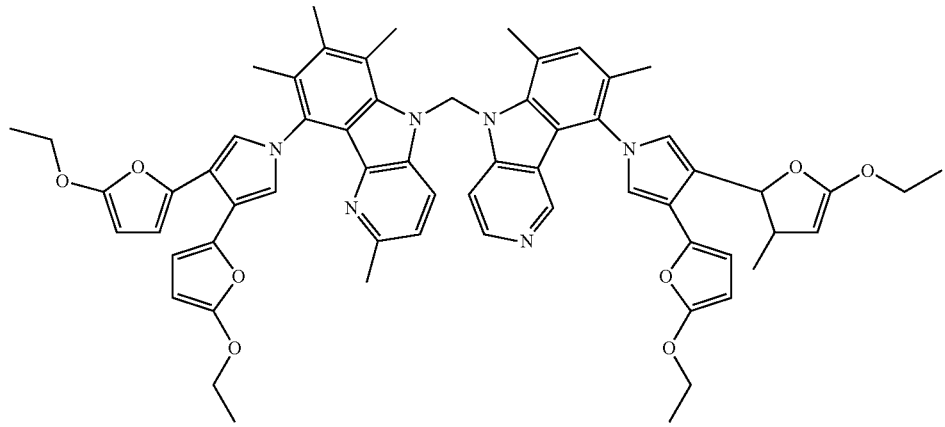
92
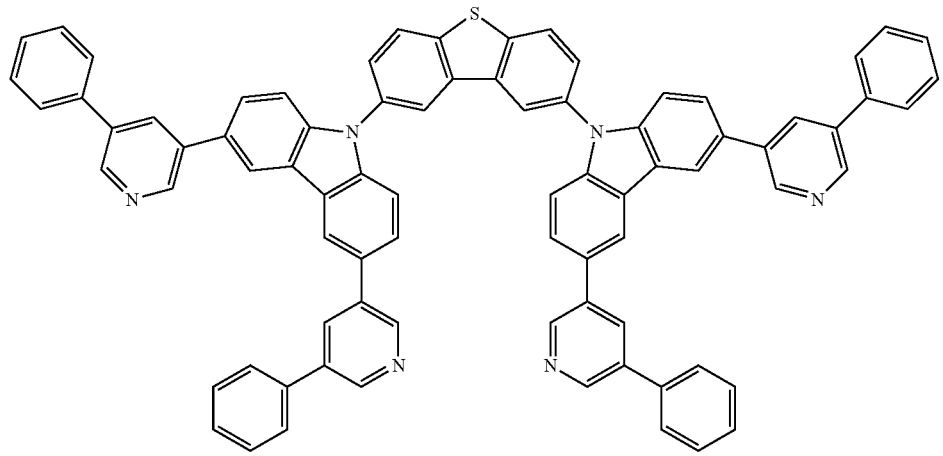
93
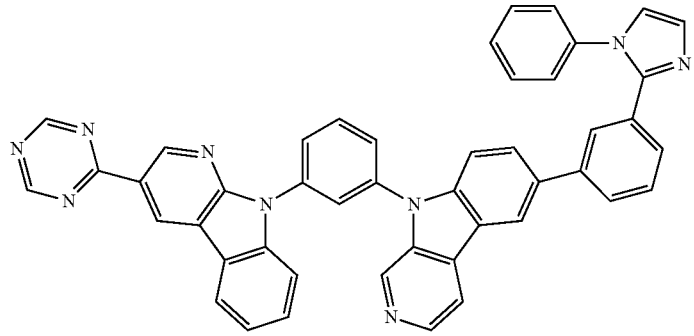
94

-continued
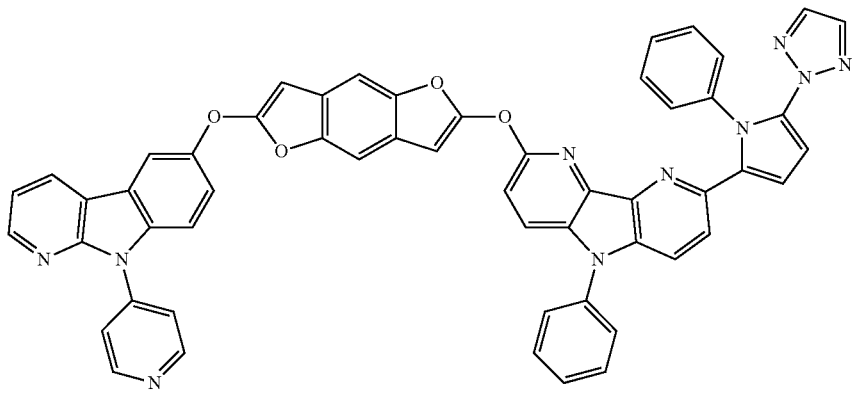
95
[Chemical Formula 36]
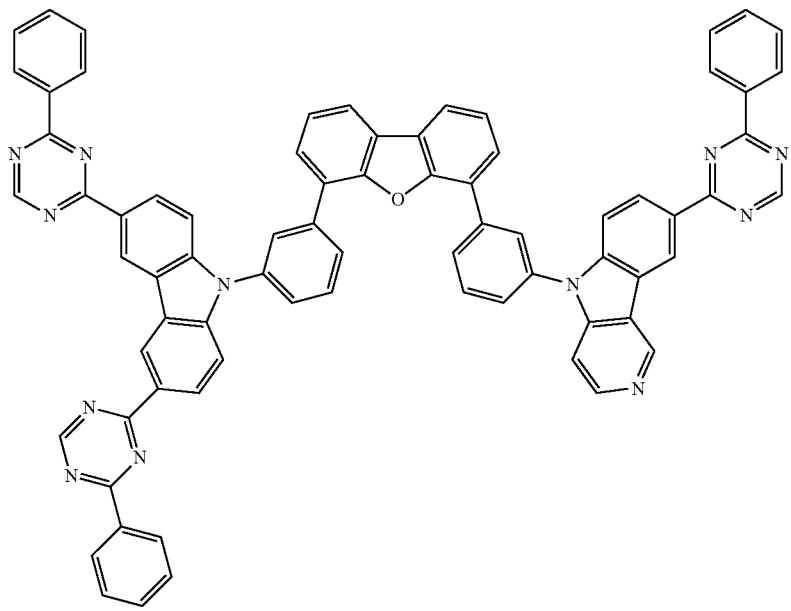
96
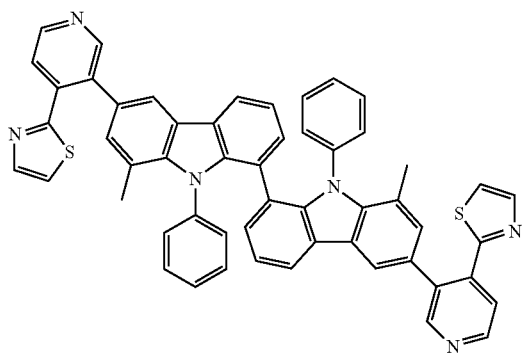
97
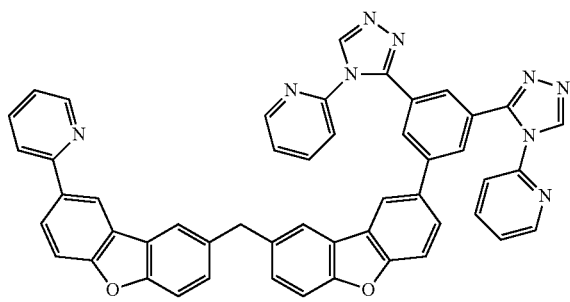
98

99
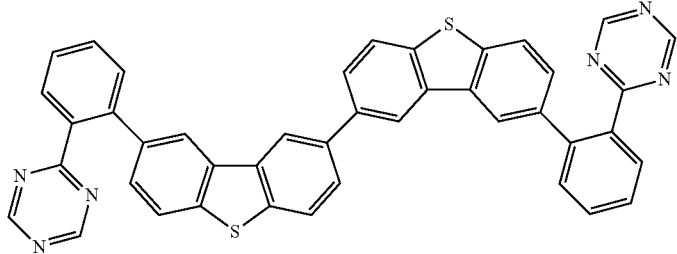
[Chemical Formula 37]
100
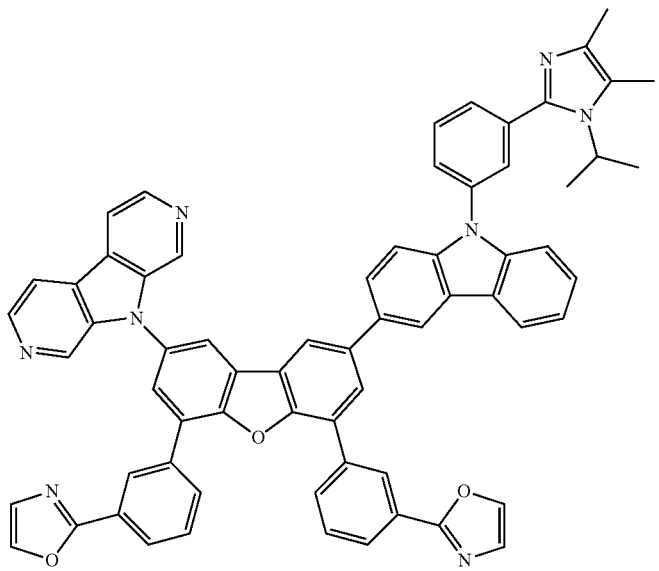
101
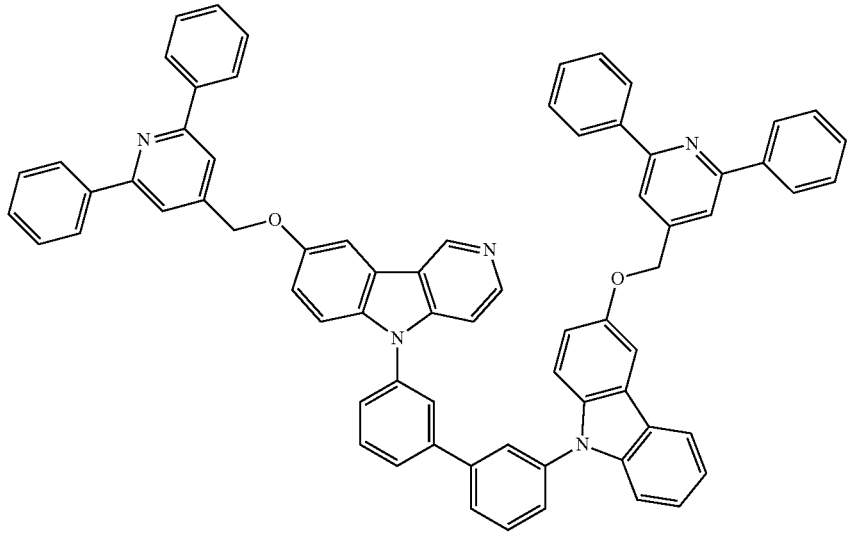

-continued
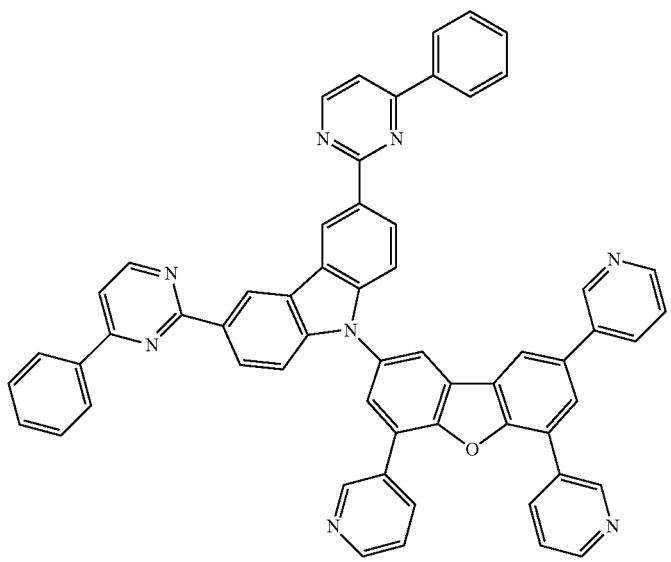
102
[Chemical Formula 38]
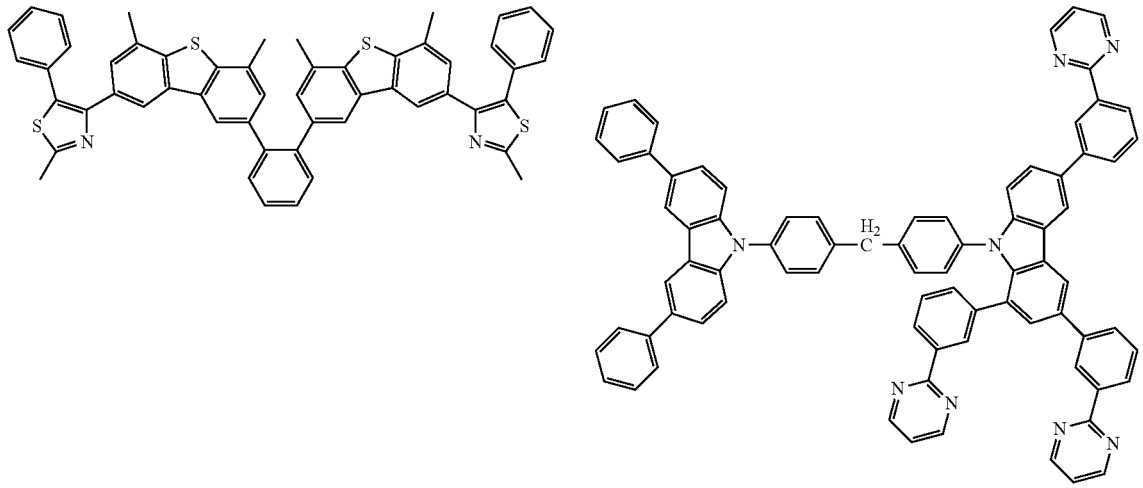
103  104
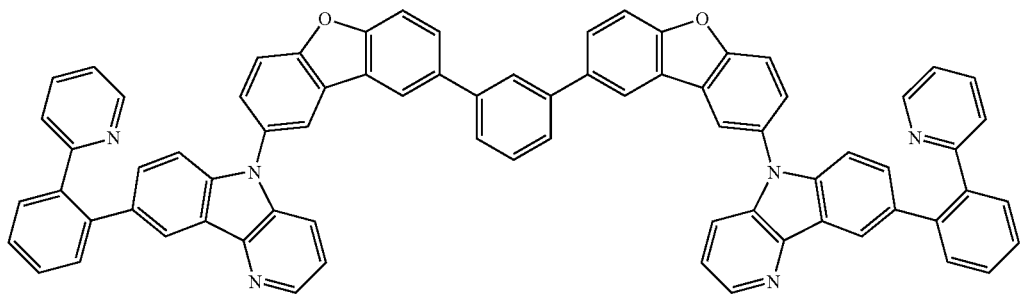
105

106
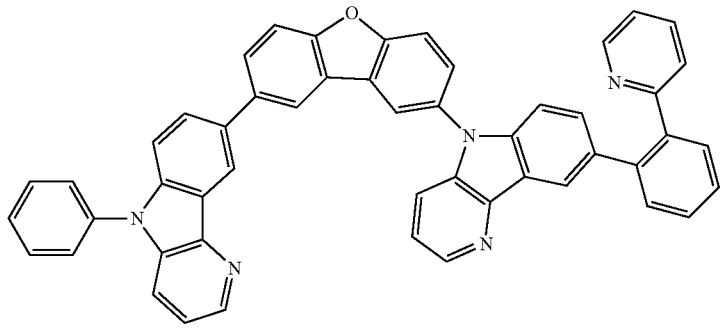
[Chemical Formula 39]
107
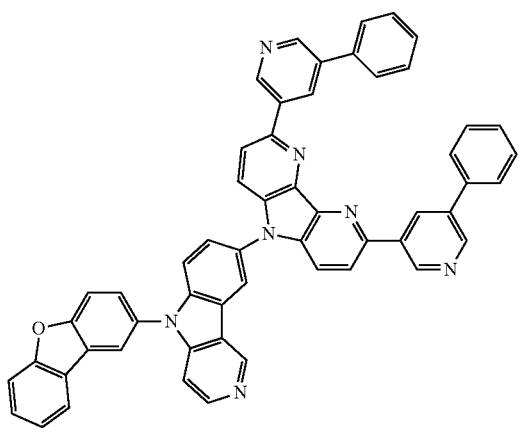
108
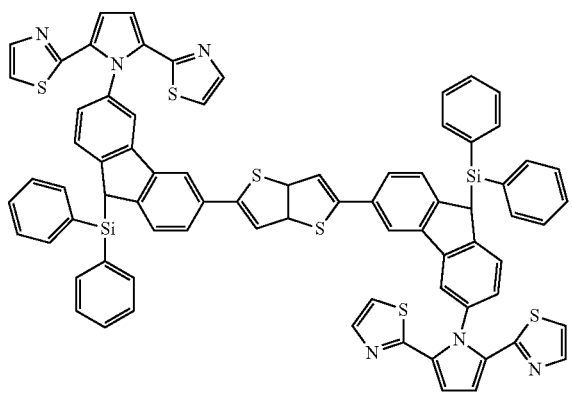
109
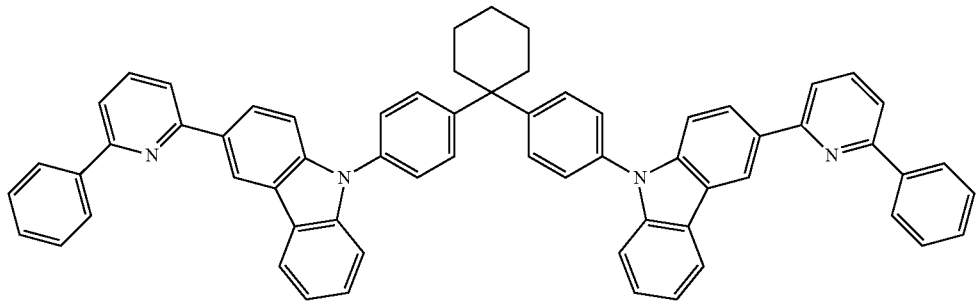
[Chemical Formula 40]
110
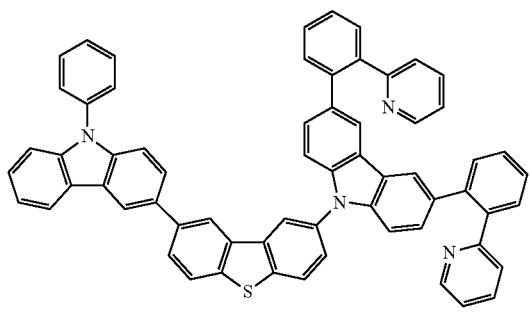
111
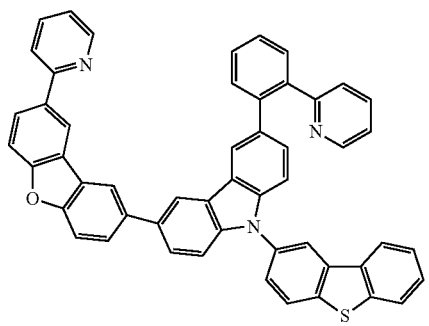

An example of synthesizing a typical compound is described below; however, the present invention is not limited thereto.

Example of Synthesizing Compound 5

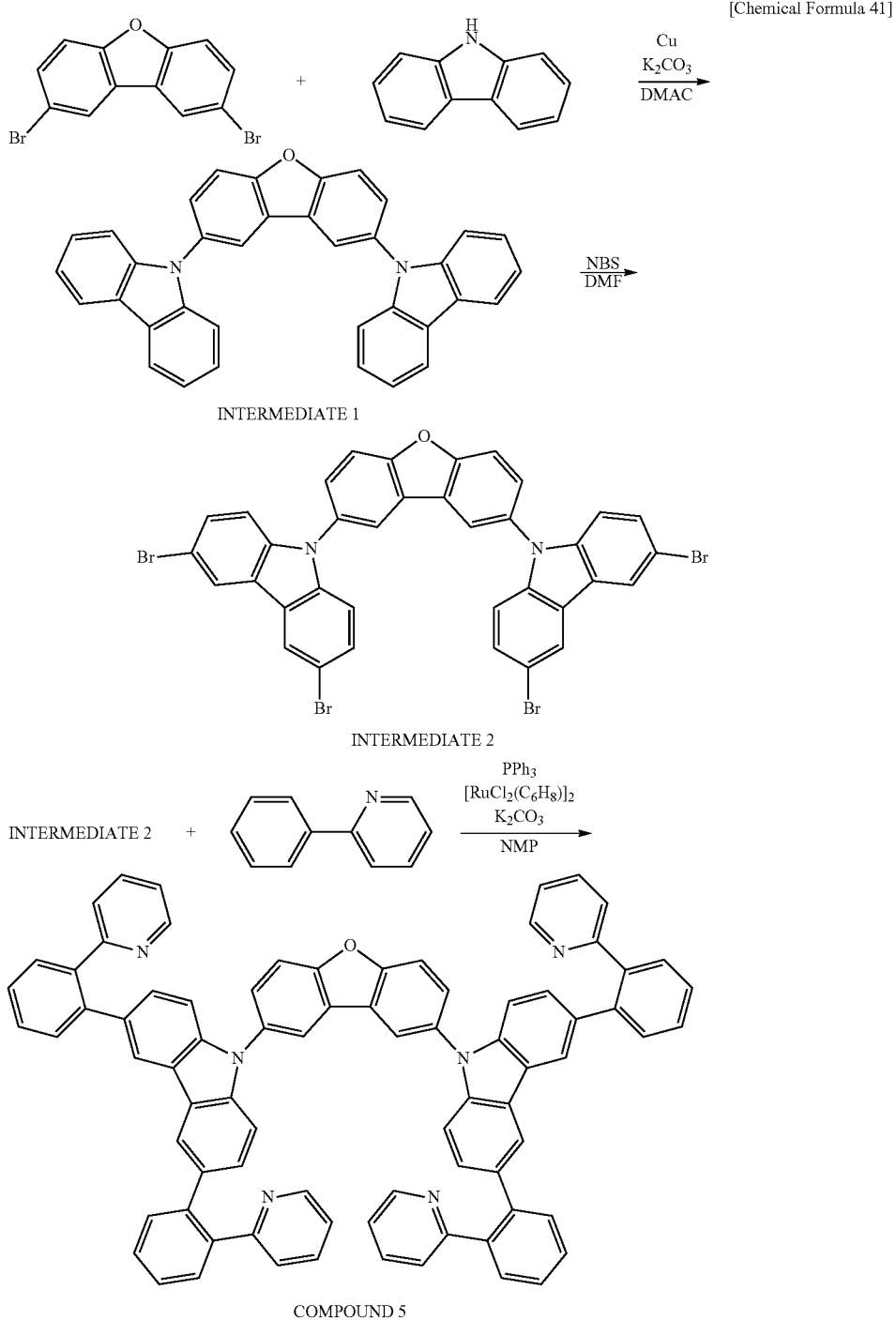

SYNTHESIS OF COMPOUND 5

[Chemical Formula 41]

Process 1: (Synthesis of Intermediate 1)

Under nitrogen atmosphere, 3,6-dibromodibenzofuran (1.0 mol), carbazole (2.0 mol), copper powder (3.0 mol) and potassium carbonate (1.5 mol) were mixed in 300 ml of DMAc (dimethylacetamide) and then stirred for 24 hours at 130° C. After the reaction liquid was cooled to room temperature, 1 L of toluene was added to the liquid, the resultant liquid was washed three times with distilled water, the solvent, was distilled under reduced pressure, and the residue was purified with silica gel flash chromatography (n-heptane:toluene=4.1 to 3.1) to obtain Intermediate 1 at a yield of 85%.

Process 2: (Synthesis of Intermediate 2)

At room temperature under atmospheric pressure, Intermediate 1 (0.5 mol) was dissolved into 100 ml of DMF, and NBS (2.0 mol) was added, and then the resultant liquid was stirred for one night at room temperature. The obtained precipitate was filtered and washed with methanol to obtain Intermediate 2 at a yield of 92%.

Process 3: (Synthesis of Compound 5)

Under nitrogen atmosphere, Intermediate 2 (0.25 mol), 2-phenylpyridine (1.0 mol), ruthenium complex $[(\eta_6\text{-}C_6H_6)RuCl_2]_2$ (0.05 mol), triphenylphosphine (0.2 mol) and potassium carbonate (12 mol) were mixed in 3 L of NMP (N-methyl-2-pyrrolidone), and then stirred for one night at 140° C.

After the reaction liquid wee cooled to room temperature, 5 L or dichloromethane was added to the liquid, and then the liquid was filtered. The solvent was distilled off from the filtrate under reduced pressure (800 Pa, 80° C.), and the (N-methyl-2-pyrrolidone) residue was purified with silica gel flash chromatography ($CH_2Cl_2$:$Et_3N$=20:1 to 10:1).

After the fractions were collected and the solvent was distilled off under reduced pressure, the residue was dissolved again into dichloromethane and washed three times with water. After the organic phase was dried with anhydrous magnesium sulfate, the solvent was distilled off under reduced pressure to obtain Compound 5 at a yield of 68%.

Auxiliary Electrode

Figure 2:
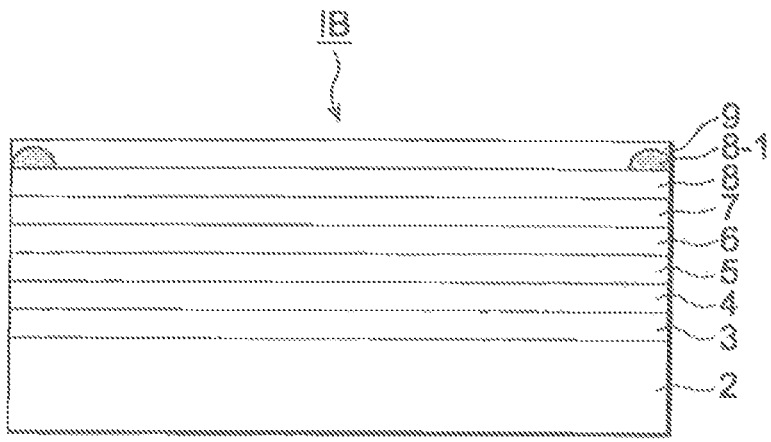
FIG. 2 is a cross-sectional view showing another example of the configuration of the organic electroluminescence element according to the present invention.

As shown in FIG. 2, in the present invention, it is possible to configure an organic EL element 1B which has an auxiliary electrode 8-1 arranged between the cathode 8 and the adjacent layer 9 in order to reduce resistance.

It is preferred that a metal having low resistance, such as aurum, platinum, argent, copper, aluminum or the like, is used to form the auxiliary electrode. Examples of the method for forming the auxiliary electrode include a deposition method, a sputtering method, a printing method, an ink-jet method, an aerosol jet method and the like. It is preferred that the line width of the auxiliary electrode is 50 μm or less in view of aperture ratio of the cathode, and the thickness of the auxiliary electrode is 1μ or more in view of electrical conductivity.

Electron Transporting Layer

In the present invention, it is preferred that an electron transporting layer containing an electron transporting compound is further provided between the cathode and the light emitting layer.

The electron transporting layer is formed of a material having a function to transport electrons; in a broad sense, an electron injecting layer (not shown) and a hole blocking layer (not shown) are included in the electron transporting layer. One electron transporting layer or a plurality of electron transporting layers can be provided.

Conventionally, an electron transporting material (which also functions as a hole blocking material) used either for an electron transporting layer, in the case where one electron transporting layer is provided, or for an electron transporting layer adjacent to the side of the cathode with respect to the light emitting layer, in the case where a plurality of electron transporting layers are provided, has a function of transferring electrons injected from the cathode to the light emitting layer; and can be selected from known compounds. Examples of the aforesaid known compounds include a nitro-substituted fluorene derivative, a diphenylquinone derivative, a thiopyrandioxide derivative, carbodiimide, a fluorenylidenemethane derivative, anthraquinonedimethane, an anthrone derivative, an oxadiazole derivative and the like. Further, in the aforesaid oxadiazole derivative, a thiadiazole derivative formed by substituting an oxygen atom of an ozadiazole ring with a sulfur atom and a quinoxaline derivative having a quinoxaline ring which is known as an electron withdrawing group may also be used as the material of the electron transporting layer. Further, a polymer material in which any of these materials is introduced into a polymer chain or a polymer material in which a polymer main chain is constituted by any of these materials may also be used.

Further, metal complexes of an 8-quinolinol derivative such as tris(8-quinolinol)aluminum ($Alq_3$), tris(5,7-dichloro-8-quinolinol)aluminum, tris(5,7-dibromo-8-quinolinol)aluminum, tris(2-methyl-8-quinolinol)aluminum, tris(5-methyl-8-quinolinol)aluminum, bis(8-quinolinol)zinc (Znq) and the like, as well as metal complexes formed by substituting the central metal of the aforesaid metal complexes with In, Mg, Cu, Ca, Sn, Ga or Pb may also be used as the material of the electron transporting layer.

Further, metal-free or metal phthalocyanine and those formed by substituting the terminal of metal-free or metal phthalocyanine with an alkyl group, a sulfonic acid group or the like may be preferably used as the material of the electron transporting layer. Further, the distyrylpyrazine derivative mentioned as an example of the material for the light emitting layer may also be used as the material of the electron transporting layer; and, similar to the cases of the hole injecting layer and the hole transporting layer, inorganic semiconductors such as an n-type Si and an n-type SiC may also be used as the material of the electron transporting layer.

The electron transporting layer can be formed by forming the aforesaid material into a thin film by a known method such as a vacuum deposition method, a spin courting method, a casting method, a printing method (which includes an ink-jet method), an LE method or the like. The thickness of the electron transporting layer is not particularly limited; however, it is typically within a range about from 5 nm to 5 μm preferably within a range from 5 nm to 200 nm. The electron transporting layer may have a single layer structure formed of one type of the aforesaid materials, or formed of two or more types of the aforesaid materials.

Further, it is also possible to dope impurities into the electron transporting layer to improve n-property. Examples of doping impurities into the electron transporting layer include those described in documents such as Japanese Unexamined Patent Application Publication Nos. 4-297076, 10-270172, 2000-196140 and 2001-102175 and J. Appl. Phys., 95, 5773 (2004). Further, in the present invention, it is preferred that the electron transporting layer contains kalium, kalium compound and/or the like. For example, potassium fluoride or the like can be used as the kalium compound. If the n-property of the electron transporting layer is improved in the aforesaid manner, it is possible to produce an element which consumes lower electric power.

Further, it is preferred that the electron transporting layer containing a kalium compound such as potassium fluoride is used since it increases the transmission and reduces the resistance of the cathode of the present invention. This is because if the cathode of the present invention is formed on the electron transporting layer containing a kalium compound such as potassium fluoride, growth of the thin-film of silver can be controlled in a preferable direction, and therefore electrical conductivity can be ensured even if the film thickness of the film is smaller.

In the present invention, the compounds represented by general formulas (1) to (3) described in the section of the adjacent layer can be preferably used as the material of the electron transporting layer (i.e., the electron transporting compound).

Light Emitting Layer

The light emitting layer used in the present invention contains a phosphorescent compound and/or a fluorescent compound as light emitting material(s).

The light emitting layer is a layer where electrons and holes injected from electrodes, or from an electron transporting layer and a hole transporting layer are recombined to emit light, and light emitting portion may be either the inside of the light emitting layer or an interface between the light emitting layer and its adjacent layer.

The structure of the light emitting layer is not particularly limited as long as the light emitting material contained therein satisfies light emitting requirements. Further, the light emitting layer may also be a plurality of light, emitting layers having the same emission spectrum and/or emission maximum wavelength. In such a case, it is preferable that, a non-luminescent intermediate layer is provided between each two light emitting layers.

The total thickness of the light emitting layers is preferably within a range front 1 nm to 100 nm and, and more preferably within a range from 1 nm to 30 nm in view of obtaining a lower driving voltage. Incidentally, the total thickness of the light emitting layers is, if the non-luminescent intermediate layer is provided between each two light emitting layers, the total thickness including the thickness of the intermediate layer (s).

The thickness of each light emitting layer as preferably to be adjusted to a range from 1 nm to 50 nm, and further preferably to be adjusted to a range from 1 nm to 20 nm. The relationship between the thickness of a blue light emitting layer, the thickness of a green Light emitting layer and the thickness of a red light emitting layer is net particularly limited.

The light emitting layers can be formed by forming a thin film of a light emitting material or a host compound, which are to be described later, using a known thin film forming method such as a vacuum, deposition, method, a spin coating method, a casting method, an LE method, an ink-jet method or the like.

Each light, emitting layer may be formed of a plurality of materials in mixture; or a phosphorescent material and a fluorescent material (also referred to as "fluorescent dopant" or "fluorescent compound") may be used in mixture in the same light emitting layer 6.

It is preferred that the light emitting layer contains a host compound (also referred to as light-emitting host or the like) and a light emitting material (also referred to as light-emitting dopant compound), and light is emitted by the light emitting material.

(Host Compound)

The host compound contained in the light emitting layer of the organic EL element 1A is a compound whose phosphorescence quantum yield preferably is, when emitting phosphorescence at room temperature (25° C.), less than 0.1, and further preferably is less than 0.01. Further, it is preferred that the volume ratio of the host compound of the compounds contained in the light emitting layer 6 is 50% or more.

One type of known host compound may be used as the host compound, or a plurality of types of known host compounds may be used as the host compound. By using a plurality of types of known host compounds, it is possible to adjust transfer of electrical charges, and it is possible to increase the efficiency of the organic EL element 1A. Further, by using a plurality of types of light emitting materials described later, it is possible to mix different colors of emission light, and therefore it is possible to obtain any emission color.

A known low-molecular compound, a high-molecular compound having a repeating unit, or a low-molecular compound having a polymerizable group such as a vinyl group or an epoxy group (a deposition polymerizable emission host) may be used as the host compound.

It is preferred that the known host compound is a compound which has hole transporting capability and electron transporting capability, which prevents increase in emission wavelength, and which has high Tg (glass transition temperature). The glass transition temperature (Tg) herein is a value obtained by using DSC (Differential Scanning Colorimetry) in conformity with JIS-K-7121.

Concrete examples (H1 to H79) of the host compound possible to be used in the present invention are shown below; however, the present invention is not limited thereto. Incidentally, in host compounds H68 to H79, x and y represent ratio of a random copolymer. Such ratio can be set to x:y=1:10, for example.

[Chemical Formula 42]

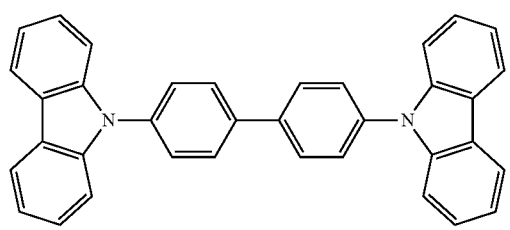

H1

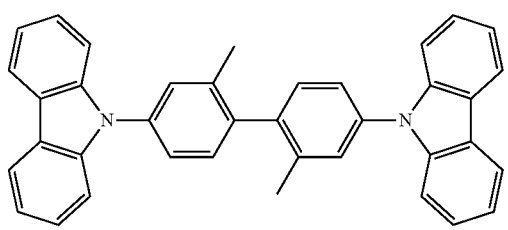

H2

-continued
H3
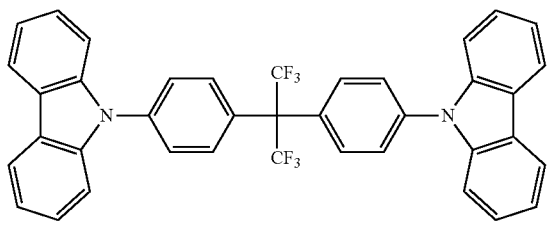
H4
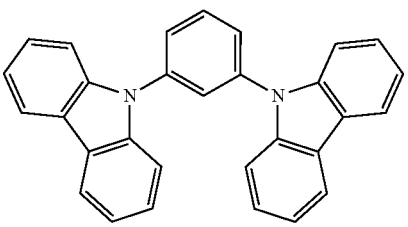
H5
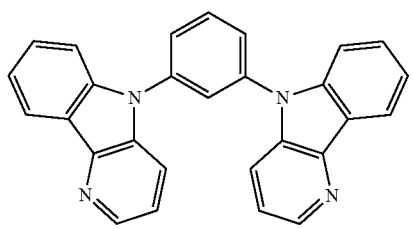
H6
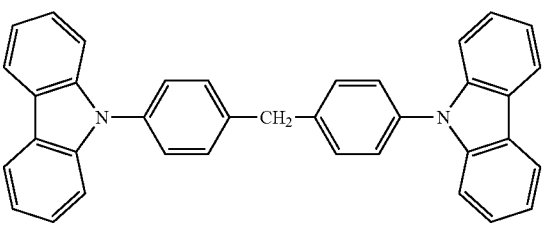
H7
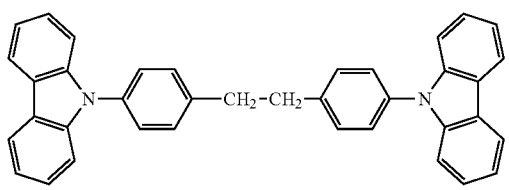
H8
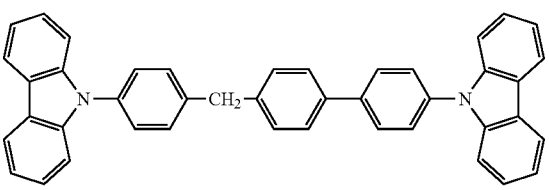
H9
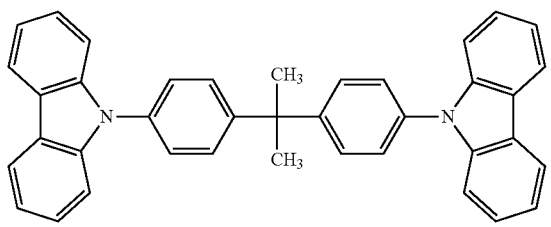
[Chemical Formula 43]
H10
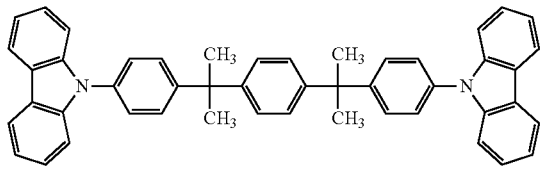
H11
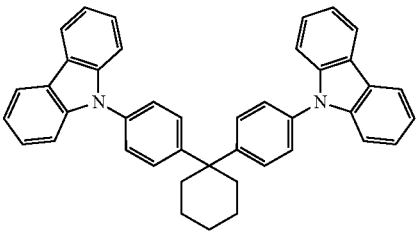
H12
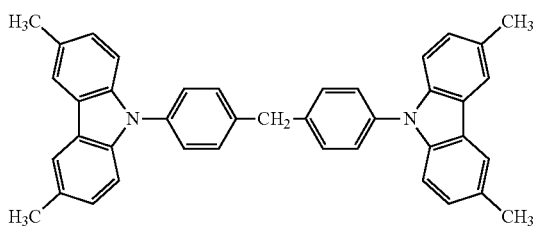
H13
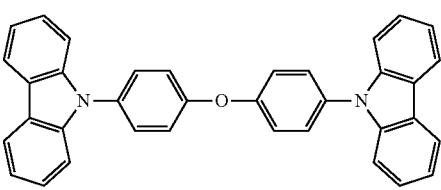

-continued
H14
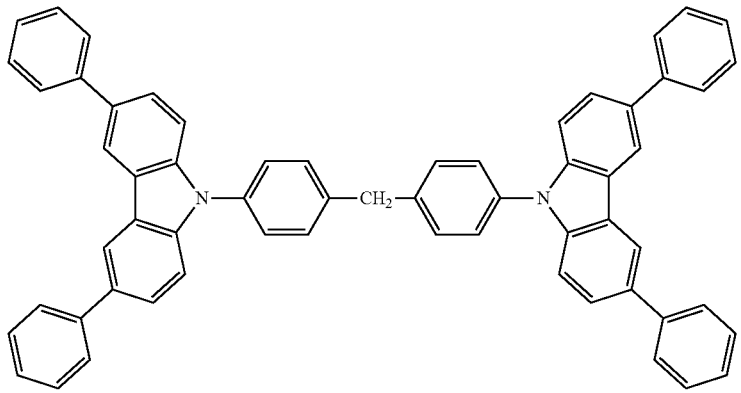
[Chemical Formula 44]
H15  H16
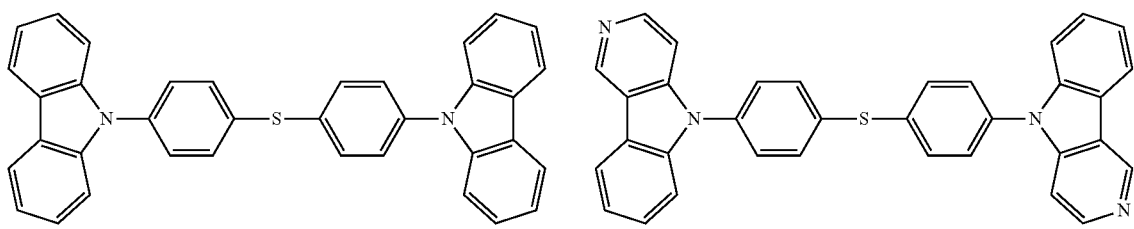
H17  H18
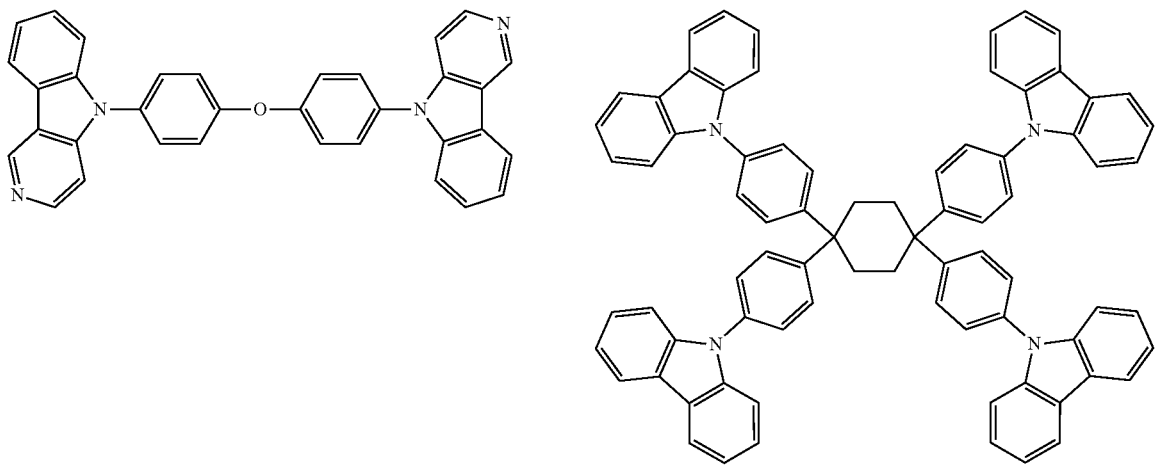
H19
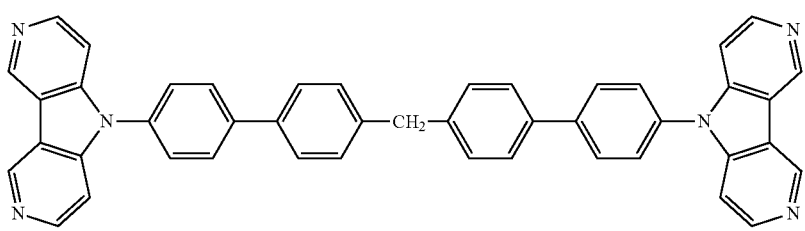
H20
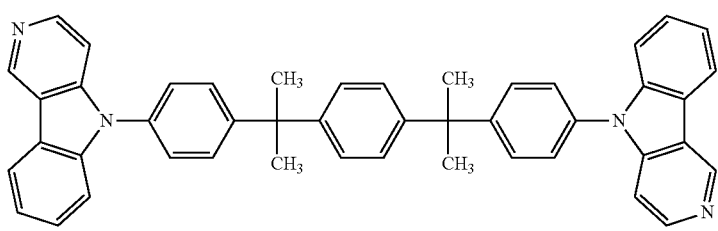

-continued
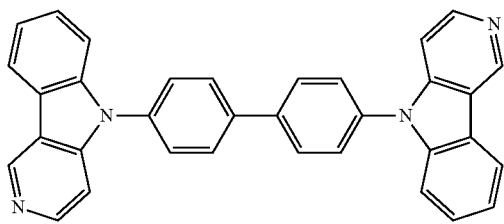
H21
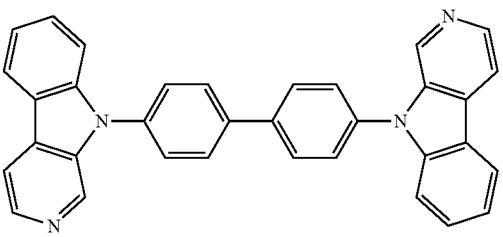
H22
[Chemical Formula 45]
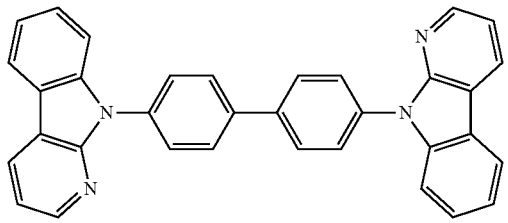
H23
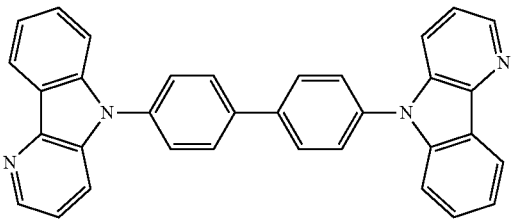
H24
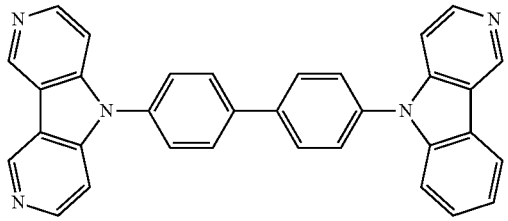
H25
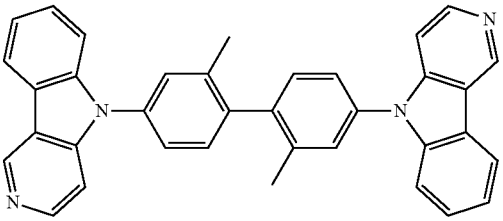
H26
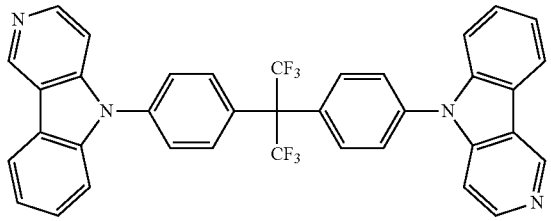
H27
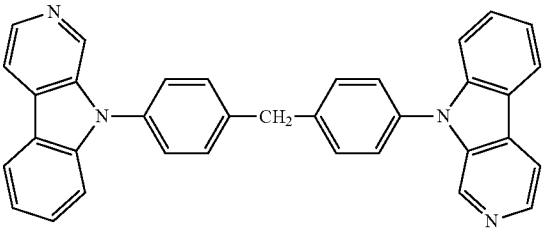
H28
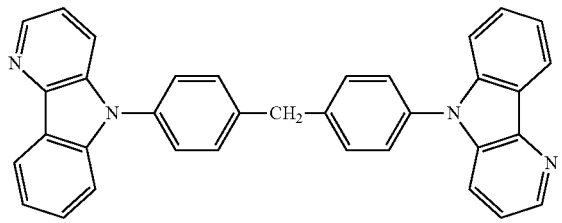
H29
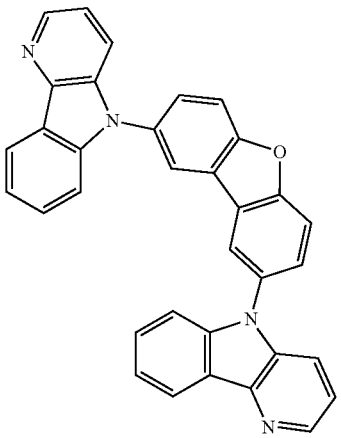
H30

[Chemical Formula 46]
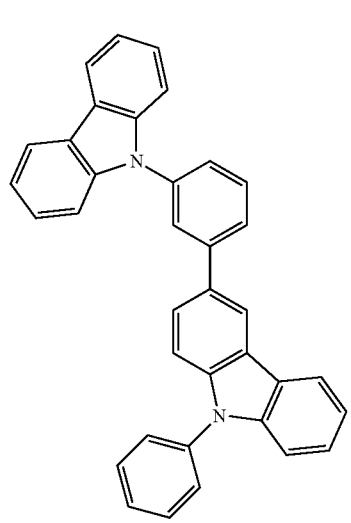
H31
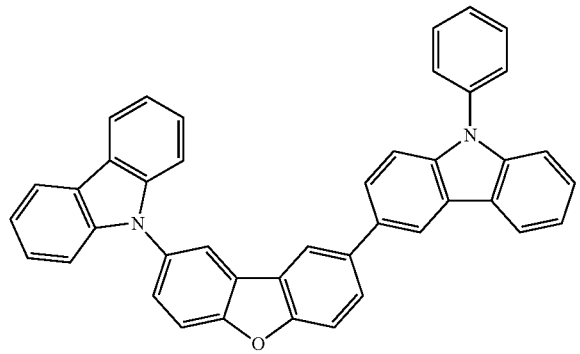
H32
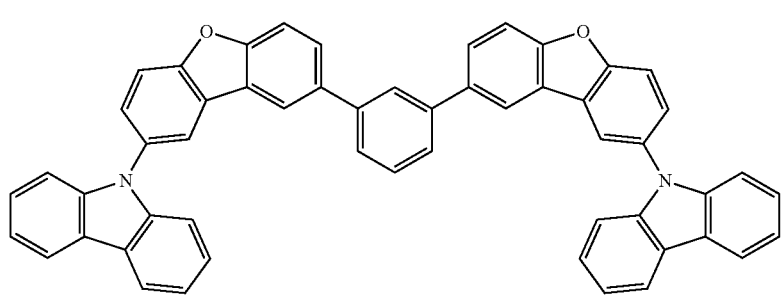
H33
[Chemical Formula 47]
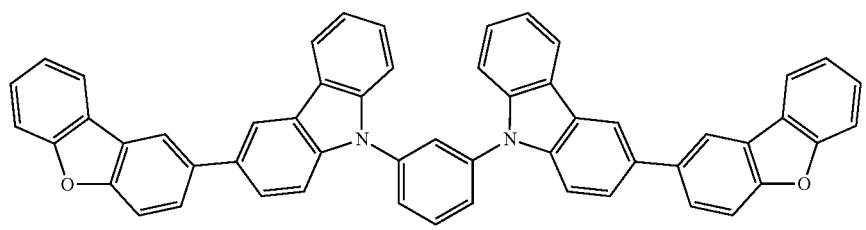
H34
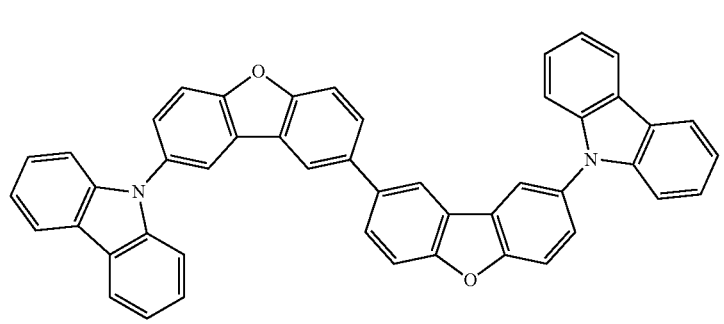
H35

-continued
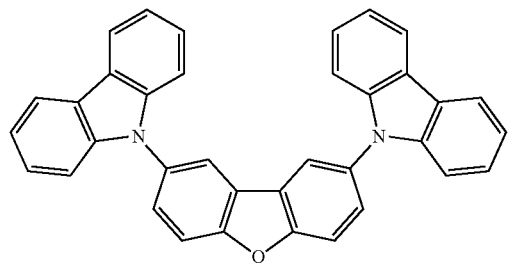
H36
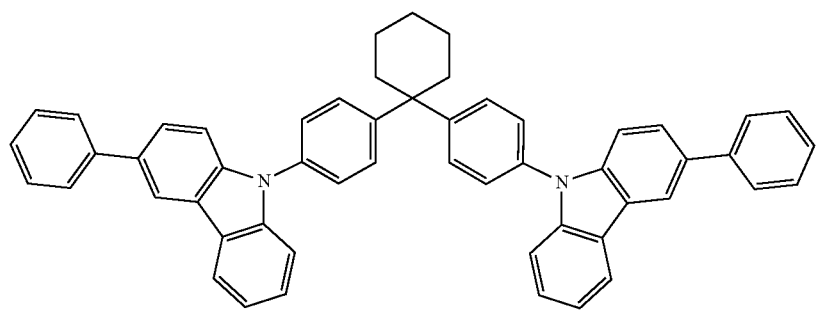
H37
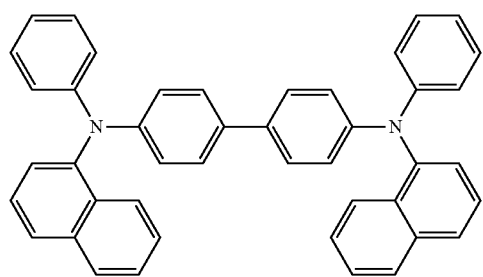
H38
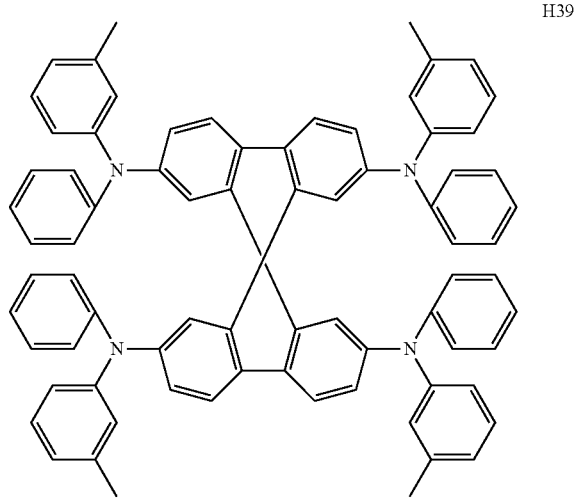
H39
[Chemical Formula 48]
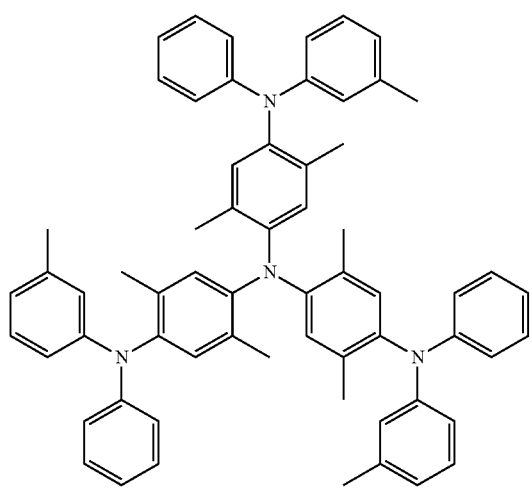
H40
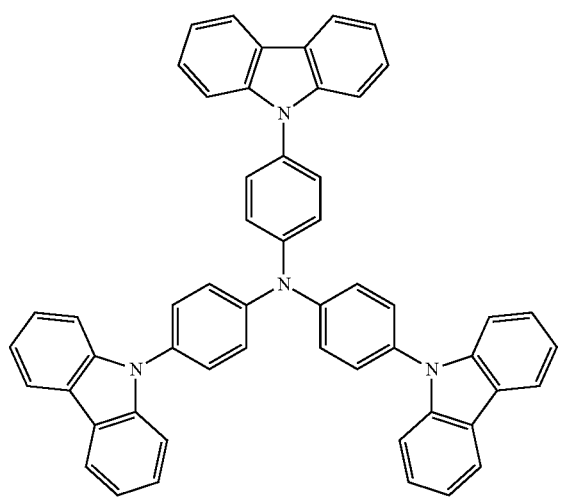
H41

-continued
H42
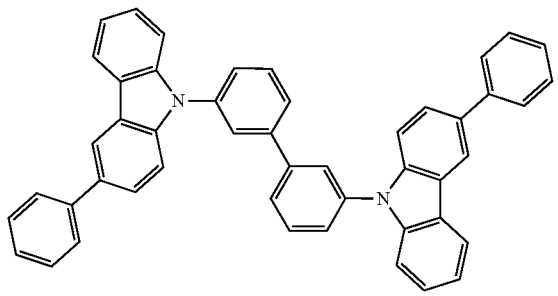
H43
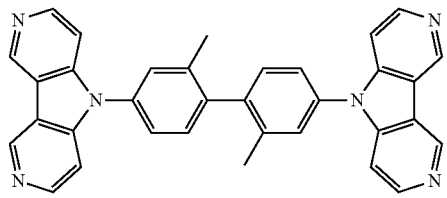
H44
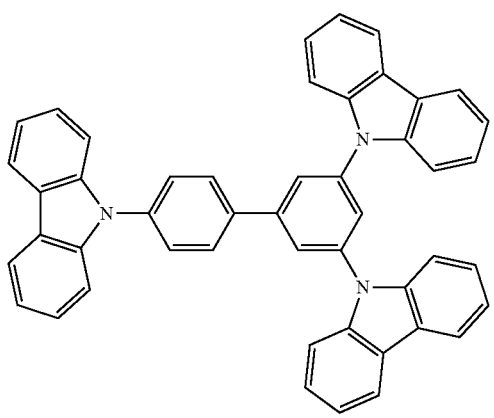
H45
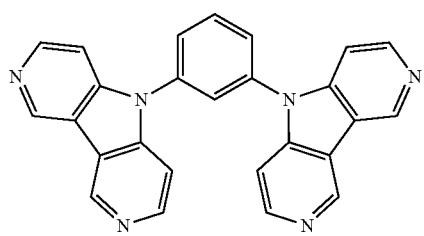
H46
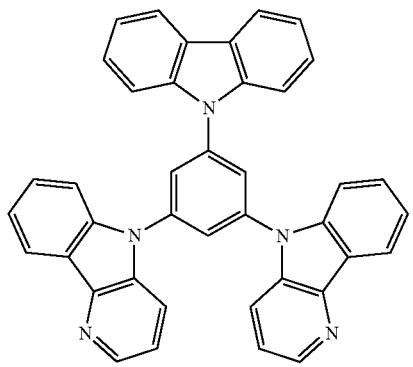
H47
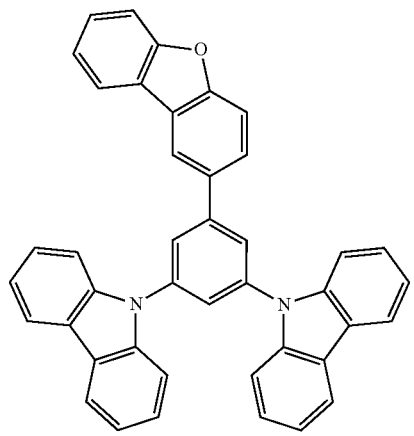
[Chemical Formula 49]
H48
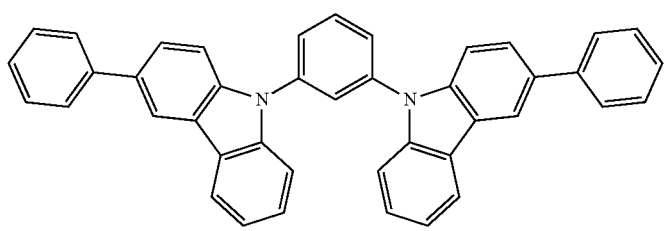

-continued
H49
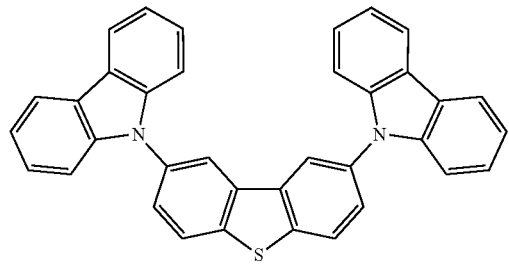
H50
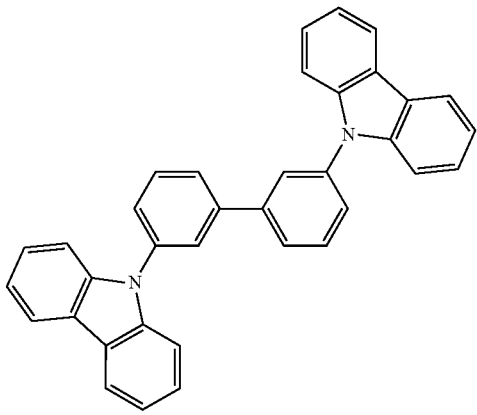
H51
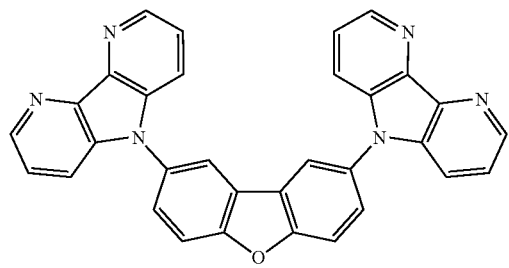
H52
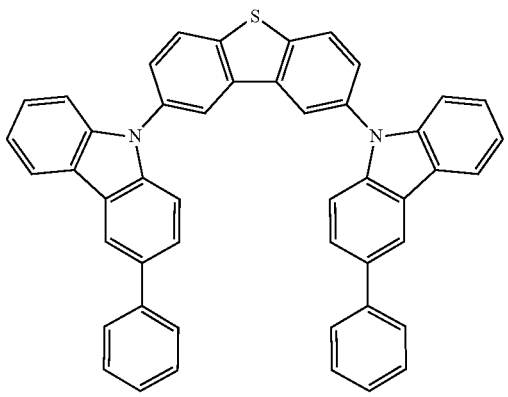
H53
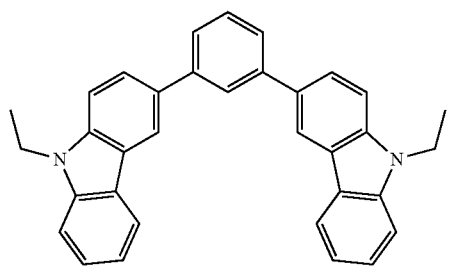
H54
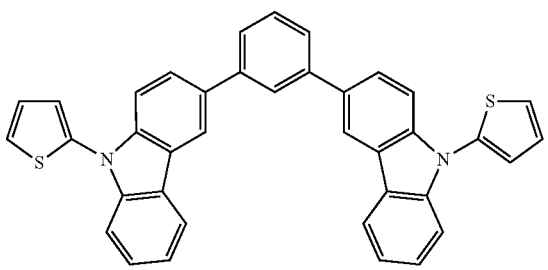
H55
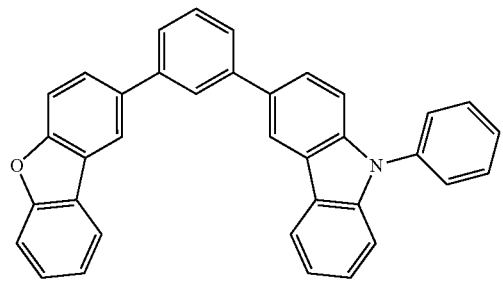

[Chemical Formula 50]
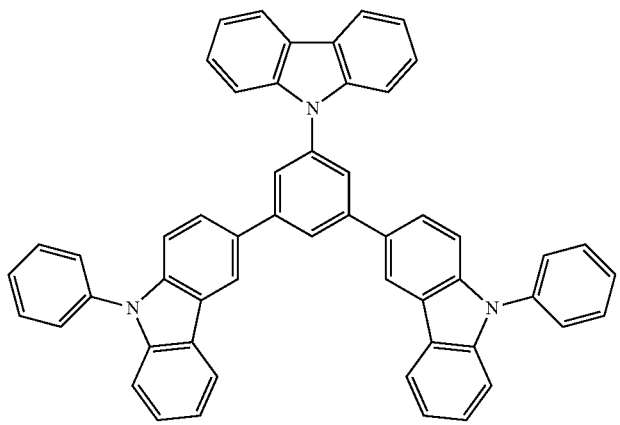
H56
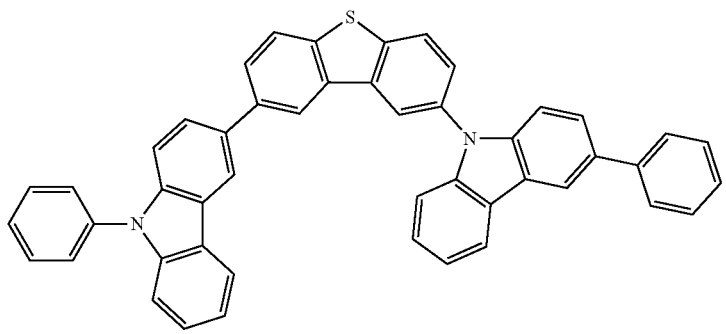
H57
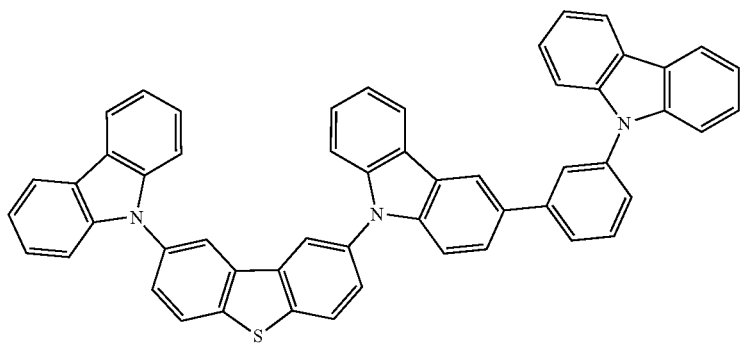
H58
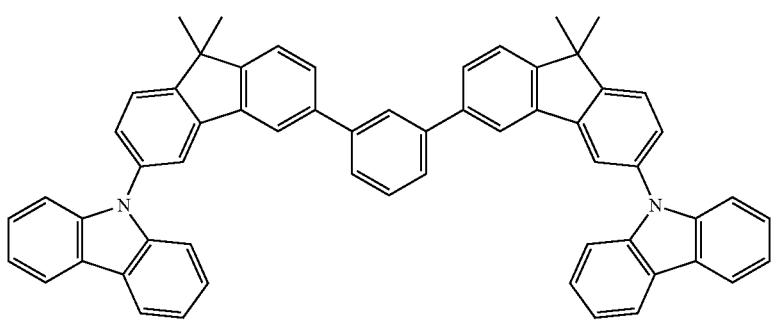
H59

[Chemical Formula 51]
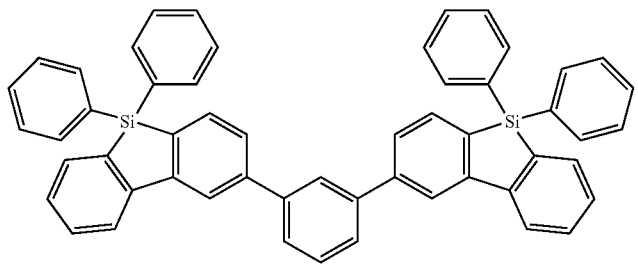
H60
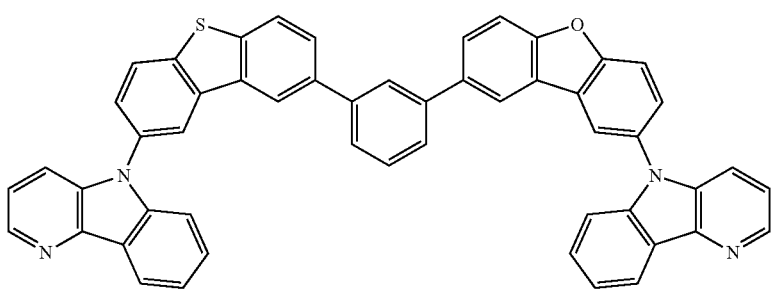
H61
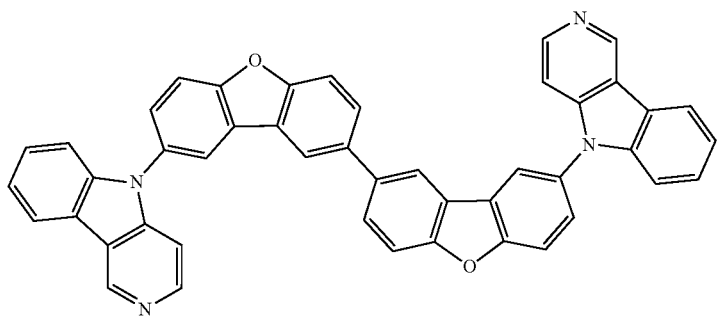
H62
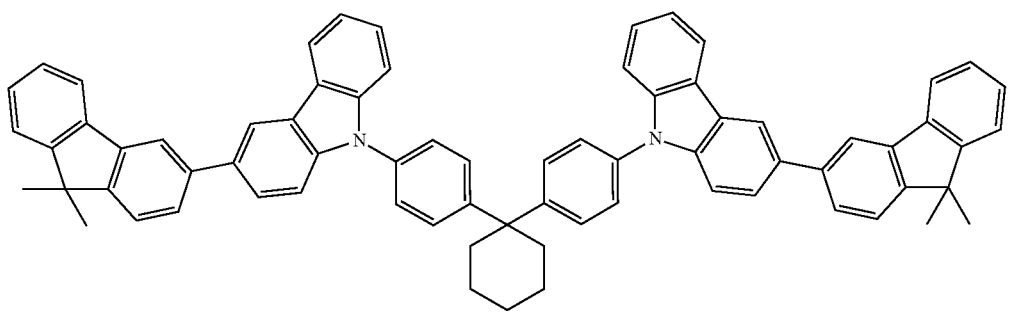
H63
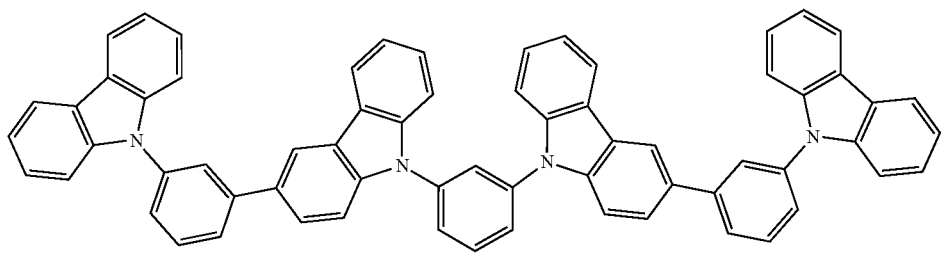
H64

[Chemical Formula 52]
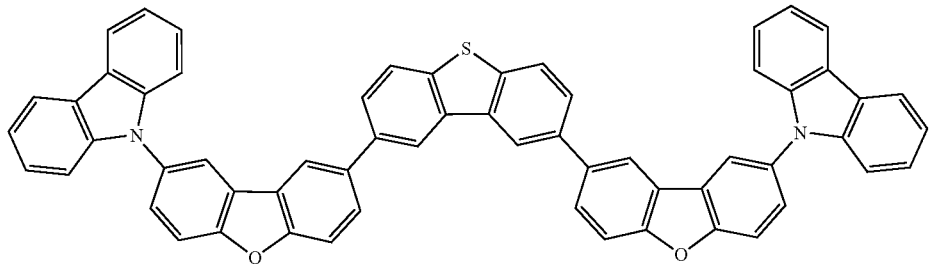
H65
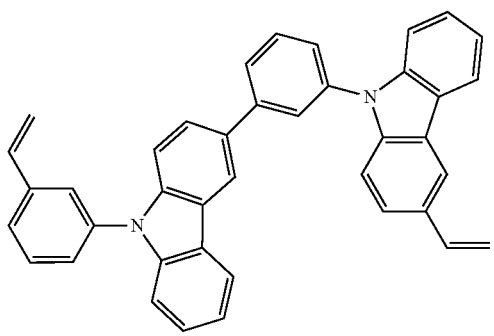
H66
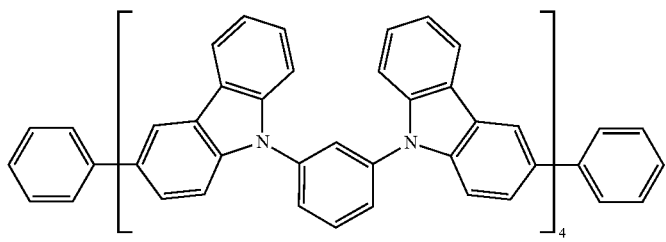
H67
[Chemical Formula 53]
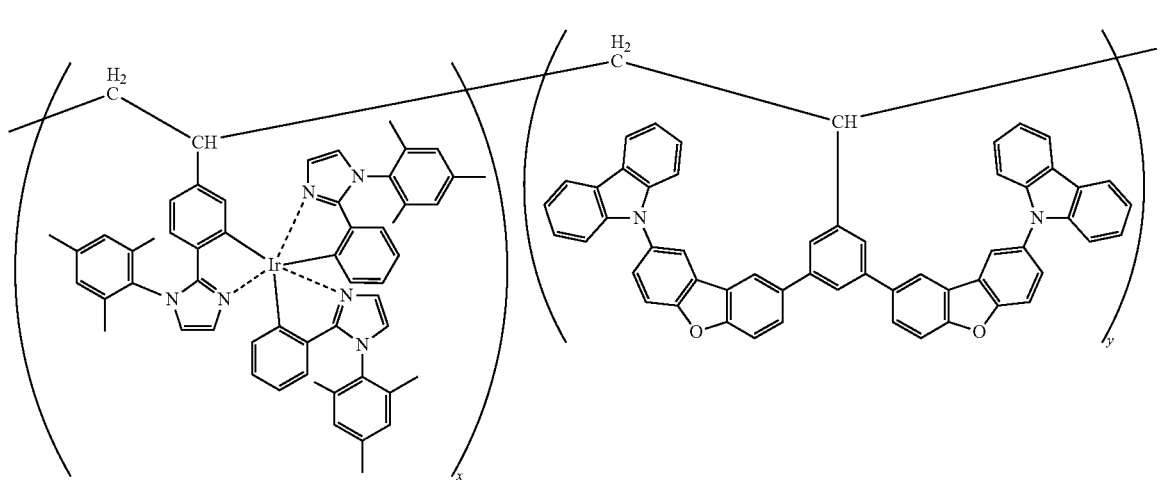
H68
x:y = 1:10
random co-polymer

[Chemical Formula 54]
H69
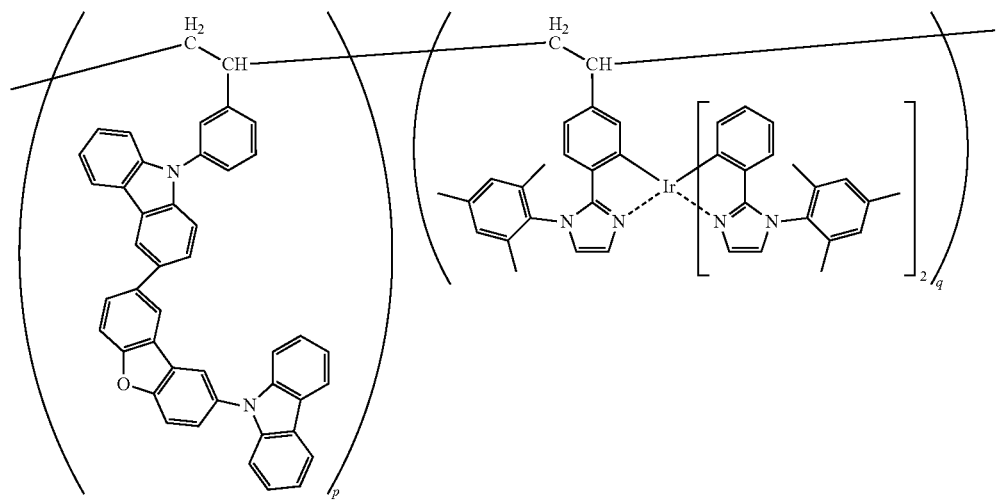
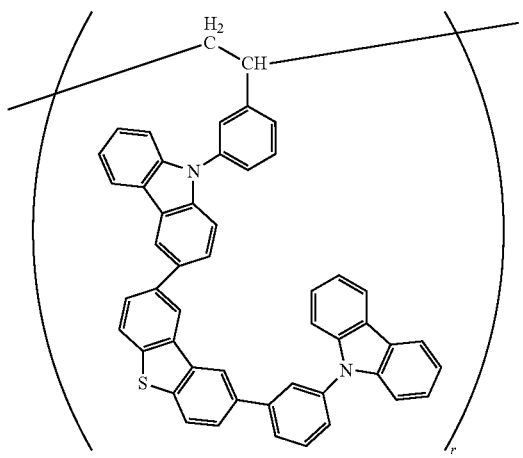
[Chemical Formula 55]
H70
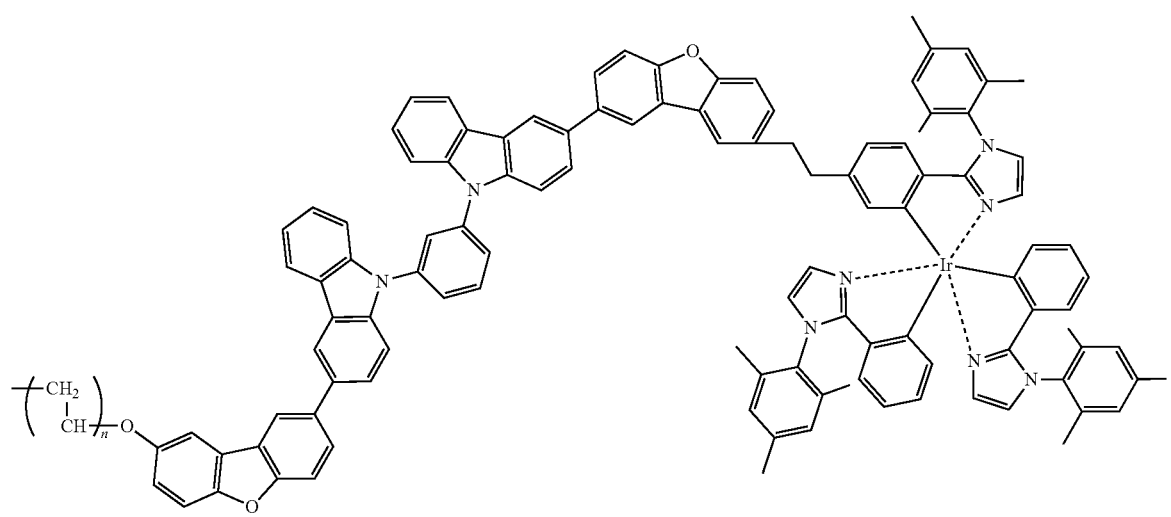

[Chemical Formula 56]
H71
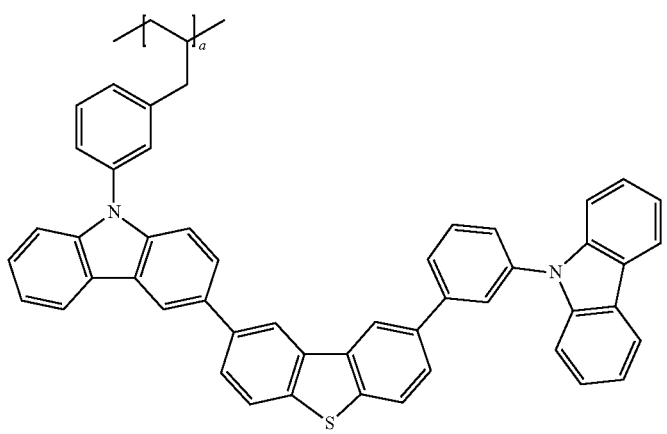
H72
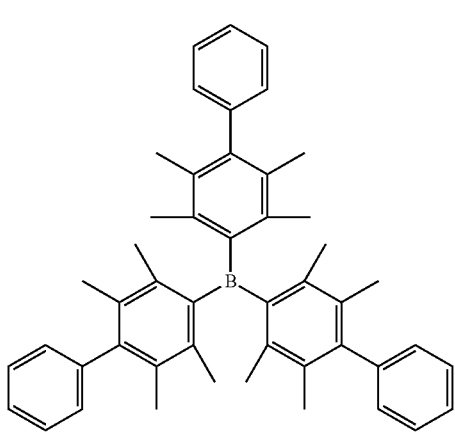
H73
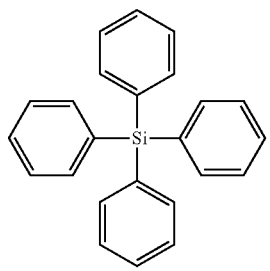
H74
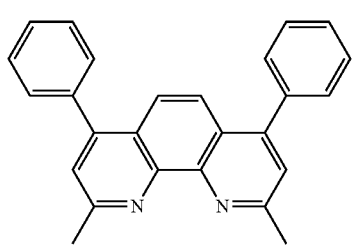
H75
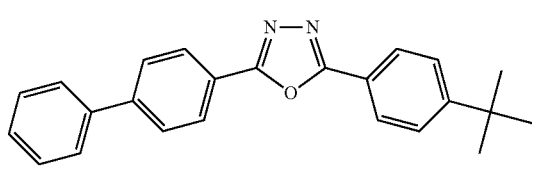
H76
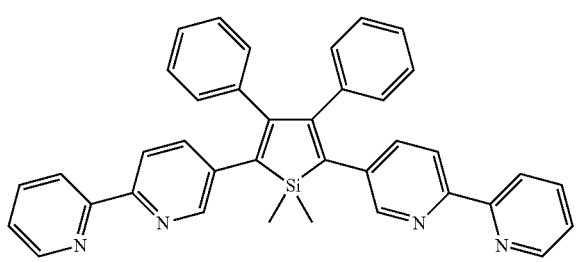
H77
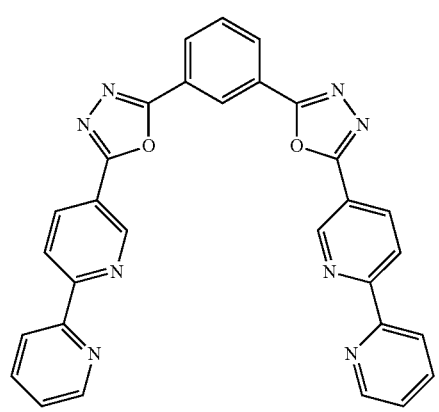

H78

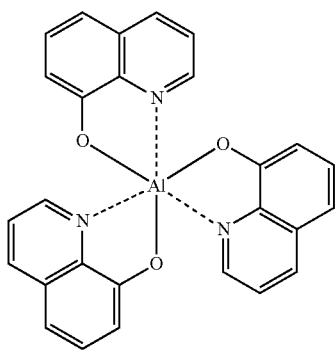

H79

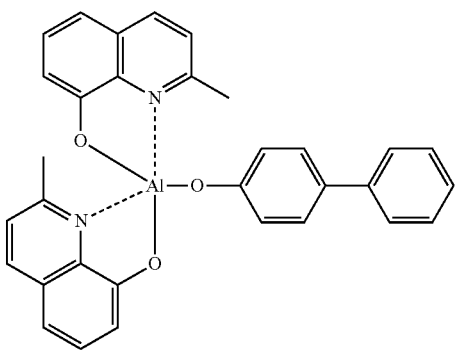

Concrete examples of the known host compound possible to be used are described in the following documents, for example: for example, Japanese Unexamined Patent Application Publication Nos. 2001-257076, 2002-308855, 2001-313179, 2002-319491, 2001-357977, 2002-334786, 2002-3860, 2002-334787, 2002-15871, 2002-334788, 2002-43056, 2002-334789, 2002-75645, 2002-338579, 2002-105445, 2002-343568, 2002-141173, 2002-352957, 2002-203683, 2002-363227, 2002-231453, 2003-3165, 2002-234888, 2003-27048, 2002-255934, 2002-260861, 2002-280183, 2002-299060, 2002-302516, 2002-305083, 2002-305084, 2002-303837 and the like.

(Light Emitting Material)

Examples of the light emitting material possible to be used in the present invention include a phosphorescent compound (also referred to as phosphorescent material).

A phosphorescent compound is a compound in which light emission from an excited triplet state is observed; to be specific, a phosphorescent compound is a compound which emits phosphorescence at room temperature (25° C.) and which exhibits a phosphorescence quantum yield 0.01 or more at 25° C.; however, preferable phosphorescence quantum yield is 0.1 or more.

The phosphorescence quantum yield can be measured by a method described on page 398 of Spectroscopy II of Lecture of Experimental Chemistry, vol. 7, 4th edition) (1992, published by Maruzen Co., Ltd.). The phosphorescence quantum yield in a solution can be measured by using various solvents. In the present invention, in the case where a phosphorescent compound as used, it is only necessary to achieve the aforesaid phosphorescence quantum yield (0.01 or more) with any one of arbitrary solvents.

Examples of light-emitting principle of the phosphorescent compound include the following two: one is an energy transfer type, in which carriers recombine on a host compound that transports the carriers, so as to generate an excited state of the host compound, and the energy is transferred to a phosphorescent compound to thereby emit light from the phosphorescent compound; the other is a carrier trap type, wherein a phosphorescent compound serves as a carrier trap, and carriers recombine on the phosphorescent compound to thereby emit light from the phosphorescent compound. In either case, the energy of the phosphorescent compound in excited state is required to be lower than that of the host compound.

The phosphorescent compound can be suitably selected from the known phosphorescent compounds used for light emitting layers of organic EL elements; the phosphorescent compound is preferably a complex compound containing a metal of groups 8 to 10 in the periodic table of elements, and further preferably an iridium compound, an osmium compound, a platinum compound (a platinum complex compound) or a rare-earth complex, and most preferably an iridium compound.

In the present invention, at least one light emitting layer may contain two or more types of phosphorescent compounds, and the ratio of concentration or the phosphorescent compounds may vary in a direction or the thickness of the light emitting layer.

It is preferred that the content of the phosphorescent compounds is equal to or higher than 0.1 vol. % but less than 30 vol. % of the total amount of the light emitting layer.

Compound Represented by General Formula 4

It is preferred that the compound (i.e., the phosphorescent compound) contained in the light emitting layer is a compound represented by the following General Formula (4).

It is preferred that the phosphorescent compound (also referred to as phosphorescent metal complex) represented by General Formula (4) is contained in the light emitting layer of the organic EL element of the present invention as a light-emitting dopant; however, the phosphorescent compound may also be contained in a constituent layer other than the light emitting layer (note that constituent layers of the organic EL element 1 of the present invention will be described later in more detail).

[Chemical Formula 57]

GENERAL FORMULA (4)

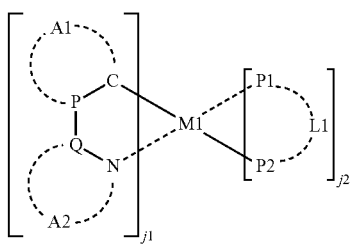

In General Formula (4), P and Q each represent a carbon atom or a nitrogen atom; A1 represents an atom group which forms an aromatic hydrocarbon ring or an aromatic heterocycle with P—C; A2 represents an atom group which forms an aromatic heterocycle with Q-N; P1-L1-P2 represents a bidentate ligand, wherein P1 and P2 each independently represent a carbon atom, a nitrogen atom or an oxygen atom, and L1 represents an atom group which forms the bidentate ligand with P1 and P2; j1 represents an integer of 1 to 3, and j2 represents an integer of 0 to 2, wherein the area of j1 and j2 is 2 or 3; and M1 represents a transition metal element of groups 8 to 10 in the periodic table of elements.

In General Formula (4), P and Q each represent a carbon atom or a nitrogen atom.

Examples of the aromatic hydrocarbon ring which is formed by A1 with P—C in General Formula (4) include a benzene ring, a biphenyl ring, a naphthalene ring, an azulene ring, an anthracene ring, a phenanthrene ring, a pyrene ring, a chrysene ring, a naphthacene ring, a triphenylene ring, an o-terphenyl ring, an m-terphenyl ring, a p-terphenyl ring, an acenaphthene ring, a coranene ring, a fluorene ring, a fluoranthrene ring, a naphthacene ring, a pentacene ring, a perylene ring, a pentaphene ring, a picene ring, a pyrene ring, a pyranthrene ring, an anthranthrene ring and the like.

Each of these rings may further have a substituent represented by Y1 in General Formula (1).

Examples of the aromatic heterocycle which is formed by A1 with P—C in General Formula (4) include a furan ring, a thiophene ring, an oxazole ring, a pyrrole ring, a pyridine ring, a pyridazine ring, a pyrimidine ring, a pyrazine ring, a triazine ring, a benzimidazole ring, an oxadiazole ring, a triazole ring, an imidazole ring, a pyrazole ring, a triazole ring, an indole ring, a benzimidazole ring, a benzothiazole ring, a benzoxazole ring, a quinozaline ring, a quinazoline ring, a phthalazine ring, a carbazole ring, an azacarbazole ring and the like.

Here, the azacarbazole ring indicates a ring formed by substituting at least one of carbon atoms of a benzene ring constituting a carbazole ring with a nitrogen atom.

These rings may each have a substituent represented by Y1 in General Formula (1).

Examples of the aromatic heterocycle which is formed by A2 with Q-N in General Formula (4) include an oxazole ring, an oxadiazole ring, an oxatriazole ring, an isoxazole ring, a tetrazole ring, a thiadiazole ring, a thiatriazole ring, an isothiazole ring, a pyrrole ring, a pyridine ring, a pyridazine ring, a pyrimidine ring, a pyrazine ring, a triazine ring, an imidazole ring, a pyrazole ring, a triazole ring and the like.

These rings may each have a substituent represented by Y1 in General Formula (1).

In General Formula (4), P1-L1-P2 represents a bidentate ligand. P1 and P2 each independently represent a carbon atom, a nitrogen atom or an oxygen atom; L1 represents an atom group which forms the bidentate ligand with P1 and P2.

Examples of the bidentate ligand represented by P1-L1-P2 in General Formula (4) include phenylpyridine, phenylpyrazole, phenylimidazole, phenyltriazole, phenyltetrazole, pyrazabole, acetylacetone, picolinic acid and the like.

In General Formula (4), j1 represents an integer of 1 to 3, j2 represents an integer of 0 to 2, and the sum or j1 and j2 is 2 or 3, wherein it is preferred that j2 is 0.

In General Formula (4) M1 represents a transition metal element (also simply referred to as transition metal) of groups 8 to 10 in the periodic table of elements, wherein it is preferred that transition metal element is iridium.

Compound Represented by General Formula (5)

Among the compounds represented by General Formula (4), a compound represented by the following General Formula (5) is further preferable.

[Chemical Formula 58]

GENERAL FORMULA (5)

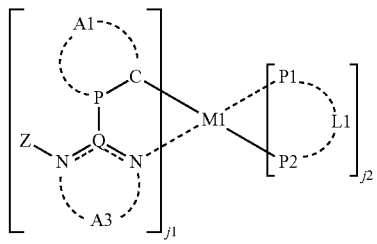

In General Formula (5), Z represents a hydrocarbon ring group or a heterocyclic group; P and Q each represent a carbon atom or a nitrogen atom; A1 represents an atom group which forms an aromatic hydrocarbon ring or an aromatic heterocycle with P—C; A3 represents —C(R01)=C(R02)-, —N=C(R02)-, —C(R01)=N— or —N=N—, wherein R01 and R02 each represent a hydrogen atom or a substituent; P1-L1-P2 represents a bidentate ligand, wherein P1 and P2 each independently represent a carbon atom, a nitrogen atom or an oxygen atom, and L1 represents an atom group which forms the bidentate ligand with P1 and P2; j1 represents an integer of 1 to 3, and j2 represents an integer of 0 to 2, wherein the sum of j1 and j2 is 2 or 3; and M1 represents a transition metal element of groups 8 to 10 in the periodic table of elements.

Examples of the hydrocarbon ring group represented by Z in General Formula (5) include a non-aromatic hydrocarbon ring group and an aromatic hydrocarbon ring group, wherein examples of the non-aromatic hydrocarbon ring group include a cyclopropyl group, a cyclopentyl group, a cyclohexyl group and the like. These groups may each be a non-substituted group or may each have a substituent described later.

Further, examples of the aromatic hydrocarbon ring group (also referred to as aromatic hydrocarbon group, aryl group or the like) include a phenyl group, a p-chlorophenyl group, a mesityl group, a tolyl group, a xylyl group, a naphthyl group, an anthryl group, an azulenyl group, an acenaphthenyl group, a fluorenyl group, a phenanthryl group, an indenyl group, a pyrenyl group, a biphenyl group and the like.

These groups may each be a non-substituted group or may each have a substituent represented by Y1 in General Formula (1).

Examples of the heterocyclic group represented by Z in General Formula (5) include a non-aromatic heterocyclic group, an aromatic heterocyclic group and the like, wherein examples of the non-aromatic heterocyclic group include groups derived from: an epoxy ring, an aziridine ring, a thiirane ring, an ozetane ring, an azetidine ring, a thietane ring, a tetrahydrothiophene ring, a dioxorane ring, a pyrrolidine ring, a pyrazolidine ring, an imidazolidine ring, an ozazolidine ring, a tetrahydrothiophene ring, a sulfonane ring, a thiazolidine ring, an ε-caprolactone ring, an ε-caprolactam ring, a piperidine ring, a hexahydropyridazine ring, a hexahydropyrimidine ring, a piperazine ring, a morpholine ring, a tetrahydropyrane ring, a 1,3-dioxane ring, a 1,4-diozane ring, a trioxane ring, a tetrahydrothiopyrane ring, a thiomorpholine ring, a thiomorpholine-1,1-dioxide ring, a pyranose ring, a diazabicyclo[2,2,2]-octane ring and the like.

These groups may each be a non-substituted group or may each have a substituent represented by Y1 in General Formula (1).

Examples of the aromatic heterocyclic group include a pyridyl group, a pyrimidinyl group, a furyl group, a pyrrolyl group, an imidazolyl group, a benzimidazolyl group, a pyrrazolyl group, a pyradinyl group, a triazolyl group (for example, a 1,2,4-triazole-1-yl group, a 1,2,3-triazole-1-yl group and the like), an oxazolyl group, a benzoxazolyl group, a triazolyl group, an isooxazolyl group, an isothiazolyl group, a furazanyl group, a thienyl group, a quinolyl group, a benzofuryl group, a dibenzofuryl group, a benzothienyl group, a dibenzothienyl group, an indolyl group, a carbazolyl group, a carbolinyl group, a diazacarbazolyl group (indicating a ring forced by substituting one of carbon atoms constituting a carboline ring of a carbolinyl group with a nitrogen atom), a quinoxalinyl group, a pyridazinyl group, a triazinyl group, a quinazolinyl group, a phthalazinyl group and the like.

These groups may each be a non-substituted group or may each have a substituent represented by Y1 in General Formula (1).

The group represented by Z is preferably an aromatic hydrocarbon ring group or an aromatic heterocyclic group.

Examples of the aromatic hydrocarbon ring which is formed by A1 with P-G in General Formula (5) include a benzene ring, a biphenyl ring, a naphthalene ring, an azulene ring, an anthracene ring, a phenanthrene ring, a pyrene ring, a chrysene ring, a naphthacene ring, a triphenylene ring, an o-terphenyl ring, an m-terphenyl ring, a p-terphenyl ring, an acenaphthene ring, a coronene ring, a fluorene ring, a fluoranthrene ring, a naphthacene ring, a pentacene ring, a perylene ring, a pentaphene ring, a picene ring, a pyrene ring, a pyranthrene ring, an anthranthrene ring and the like.

Each of these rings may further have a substituent represented by Y1 in General Formula (1).

Examples of the aromatic heterocycle which is formed by A1 with P—C in General Formula (5) include a furan ring, a thiophene ring, an oxazole ring, a pyrrole ring, a pyridine ring, a pyridazine ring, a pyrimidine ring, a pyrazine ring, a triazine ring, a benzimidazole ring, an oxadiazole ring, a triazole ring, an imidazole ring, a pyrazole ring, a triazole ring, an indole ring, a benzimidazole ring, a benzothiazole ring, a benzoxazole ring, a quinoxaline ring, a quinazoline ring, a phthalazine ring, a carbazole ring, a carboline ring, an azacarbazole ring and the like.

Here, the azacarbazole ring indicates a ring formed by substituting at least one of carbon a atoms of a benzene ring constituting a carbazole ring with a nitrogen atom.

Each of these rings may further have a substituent represented by Y1 in General Formula (1).

The substituent represented by each of R01 and R02 in C(R01)=C(R02)-, —N=C(R02)- and —C(R01)=N— represented by A3 in General Formula (5) is synonymous with the substituent represented by Y1 an General Formula (1).

Examples of the bidentate ligand represented by P1-L1-P2 in General Formula (5) include phenylpyridine, phenylpyrazole, phenylimidazole, phenyltriazole, phenyltetrazole, pyrazabole, acetylacetone, picolinic acid and the like.

Further, j1 represents an integer of 1 to 3, j2 represents an integer or 0 to 2, and the sum of j1 and j2 is 2 or 3, wherein it is preferred that j2 is 0.

The transition metal element (also simply referred to as transition metal) of groups 8 to 10 in the periodic table of elements represented by M1 in General Formula (5) is synonymous with the transition metal element or groups 8 to 10 in the periodic table of elements represented by M1 in General Formula (4).

Compound Represented by General Formula (6)

A compound represented by the following General Formula (6) is one of preferable examples of the compounds represented by General Formula (5).

[Chemical Formula 59]

GENERAL FORMULA (6)

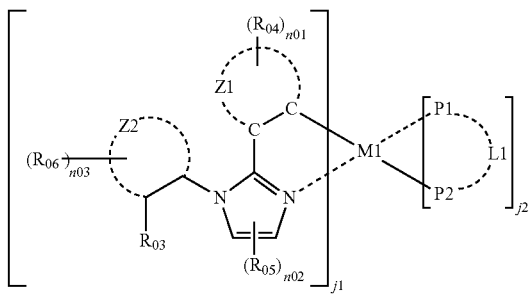

In General Formula (6) $R_{03}$ represents a substituent, $R_{04}$ represents a hydrogen atom or a substituent, and a plurality of $P_{04}$ may be bonded to each other to form a ring; n01 represents an integer of 1 to 4; $R_{05}$ represents a hydrogen atom or a substituent, and a plurality of $R_{05}$ may be bonded to each other to form a ring; n02 represents an integer of 1 to 2; $R_{04}$ represents a hydrogen atom or a substituent, and a plurality of $P_{04}$ may be bonded to each other to form a ring; n03 represents an integer of 1 to 4; Z1 represents an atom group necessary to form, along with C—C, 6-membered aromatic hydrocarbon ring, or a 5-membered or 6-membered aromatic heterocycle; Z2 represents an atom group necessary to form a hydrocarbon ring group or a heterocyclic group; P1-L1-P2 represents a bidentate ligand, wherein P1 and P2 each independently represent a carbon atom, a nitrogen atom or an oxygen atom, and L1 represents an atom group which forms the bidentate ligand with P1 and P2; j1 represents an integer of 1 to 3, and j2 represents an integer of 0 to 2, wherein the sum of j1 and j2 is 2 or 3; and M1 represents a transition metal element of groups 8 to 10 in the periodic table of elements. $R_{03}$ and $R_{06}$ may be bonded to each other to form a ring, and the same goes for "$R_{04}$ and $R_{06}$" and "$R_{05}$ and $R_{06}$".

The substituents respectively represented by $R_{03}$, $R_{04}$, $R_{05}$, and $R_{06}$ in General Formula (6) are each synonymous with the substituent represented by Y1 in General Formula (1).

Examples of the 6-membered aromatic hydrocarbon ring which is formed by Z1 with C—C in General Formula (6) include a benzene ring and the like.

Each of these rings may further have a substituent represented by Y1 in General Formula (1).

Examples of the 5-membered or 6-membered aromatic heterocycle which is formed by Z1 with C—C in General Formula (6) include an oxazole ring, an ozadiazole ring, an oxatriazole ring, an isozazole ring, a tetrazole ring, a thiadiazole ring, a thiatriazole ring, an isothiazole ring, a thiophene ring, furan ring, a pyrrole ring, a pyridine ring, a pyridazine ring, a pyrimidine ring, a pyrazine ring, a triazine ring, an imidazole ring, a pyrazole ring, a triazole ring and the like.

Each of these rings may further have a substituent represented by Y1 in General Formula (1).

Examples of the hydrocarbon ring group represented by Z2 in General Formula (6) include a non-aromatic hydrocarbon ring group and an aromatic hydrocarbon ring group, wherein examples of the non-aromatic hydrocarbon ring group include a cyclopropyl group, a cyclopentyl group, a cyclohexyl group and one like. These groups may each be a non-substituent or may each have a substituent described later.

Further, examples of the aromatic hydrocarbon ring group (also referred to as aromatic hydrocarbon group, aryl group or the like) include a phenyl group, a p-chlorophenyl group, a mesityl group, a tolyl group, a xylyl group, a naphthyl group, an anthryl group, an azulenyl group, an acenaphthenyl group, a fluorenyl group, a phenanthryl group, an indenyl group, a pyrenyl group, a biphenyl group and the like. These groups may each be a non-substituted group or may each have a substituent represented by Y1 in General Formula (1).

Examples of the heterocyclic group represented by Z2 in General Formula (6) include a non-aromatic heterocyclic group, an aromatic heterocyclic group and the like, wherein examples of the non-aromatic heterocyclic group include groups derived from: an epoxy ring, an aziridine ring, a thiirane ring an oxetane ring, an azetidine ring, a thietane ring, a tetrahydrofuran ring, a dioxorane ring, a pyrrolidine ring, a pyrazolidine ring, an imidazolidine ring, an oxazolidine ring, a tetrahydrothiophene ring, a sulforane ring, a thiazolidine ring, an ε-caprolactone ring, an ε-caprolactam ring, a piperidine ring, a hexahydropyridazine ring, a hexahydropyrimidine ring, a piperazine ring, a morpholine ring, a tetrahydropyrane ring, a 1,3-dioxane ring, a 1,4-dioxane ring, a trioxane ring, a tetrahydrothiopyrane ring, a thiomorpholine ring, a thiomorpholine-1,1-dioxide ring, a pyranose ring, a diazabicyclo[2,2,2]-octane ring and the like. These groups may each be a non-substituted group or may each have a substituent represented by Y1 in General Formula (1).

Examples of the aromatic heterocyclic group include a pyridyl group, a pyrimidinyl group, a furyl group, a pyrrolyl group, an imidazolyl group, a benzimidazolyl group, a pyrrazolyl group, a pyradinyl group, a triazolyl group (for example, a 1,2,4-triazole-1-yl group, a 1,2,3-triazole-1-yl group and the like), an oxazolyl group, a benzoxazolyl group, a triazolyl group, an isooxazolyl group, an isothiazolyl group, a furazanyl group, a thienyl group, a quinolyl group, a benzofuryl group, an indolyl group, a carbazolyl group, a dibenzothienyl group, an indolyl group, a carbazolyl group, a carbolinyl group, a diazacarbazolyl group (indicating a ring formed by substituting one of carbon atoms constituting a carboline ring of a carbolinyl group with a nitrogen atom), a quinoxalinyl group, a pyridazinyl group, a triazinyl group, a quinazolinyl group, a phthalazinyl group and the like.

These rings may each be a non-substituted group or may each have a substituent represented by Y1 an General Formula (1).

It is preferred that, in General Formula (6), the groups formed by Z1 and Z2 is a benzene ring.

The bidentate ligand represented by P1-L1-P2 in General Formula (6) is synonymous with the bidentate ligand represented by P1-L1-P2 in General Formula (4).

The transition metal element of groups 8 to 10 in the periodic table of elements represented by M1 in General Formula (6) is synonymous with the transition metal element of groups 8 to 10 in the periodic table of elements represented by M1 in General Formula (4).

The phosphorescent compound may be suitably selected from the known phosphorescent compounds used for light emitting layers of organic EL elements.

The phosphorescent compound of the present invention is preferably a complex compound containing a metal of groups 8 to 10 in the periodic table of elements, and further preferably an iridium compound, an osmium compound, a platinum compound (a platinum complex compound) or a rare-earth complex, and most preferably an iridium compound.

Concrete examples (PT-1 to Pt-3, A-1, Ir-1 to Ir-45) of the phosphorescent compound of the present invention are shown below; however, the present invention is not limited thereto. Note that, in these compounds, m and n each represent number of replication.

[Chemical Formula 60]

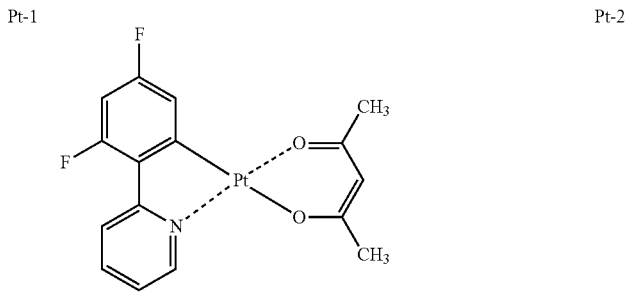

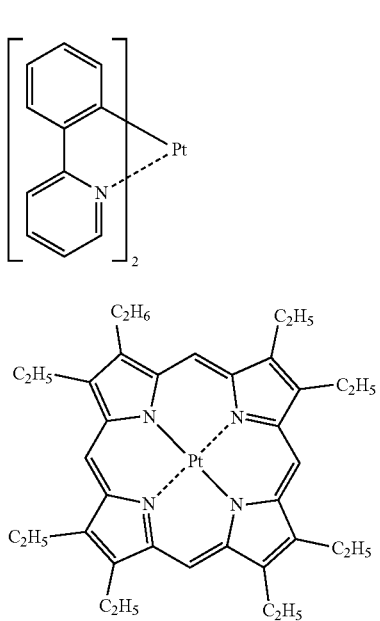

-continued
A-1
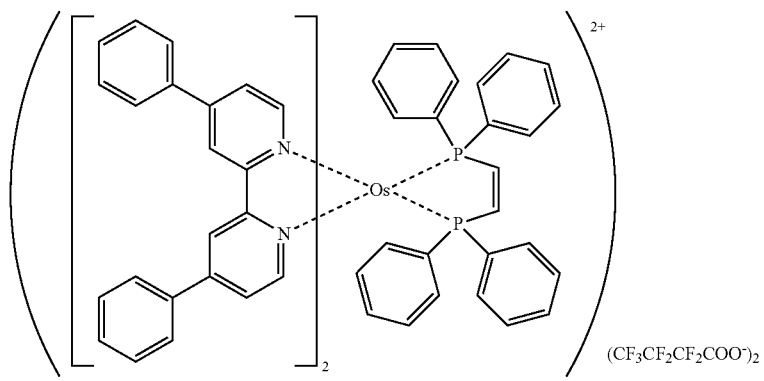
(CF₃CF₂CF₂COO⁻)₂
[Chemical Formula 61]
Ir-1          Ir-2
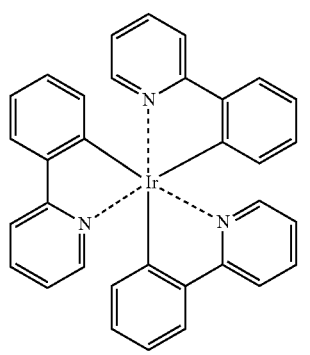 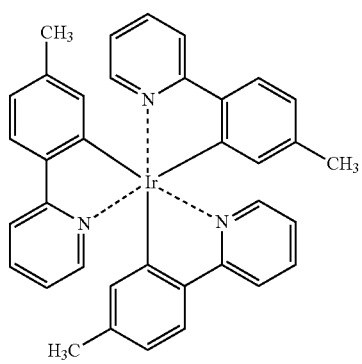
Ir-3          Ir-4
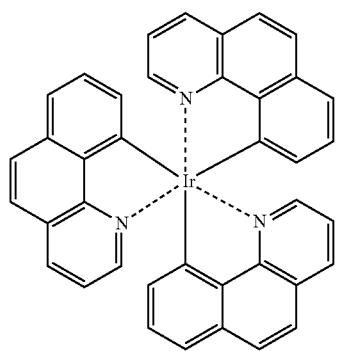 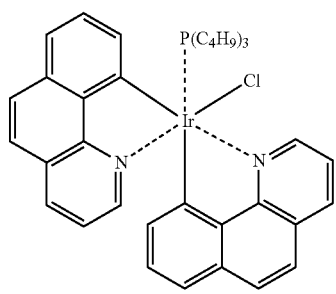
Ir-5          Ir-6
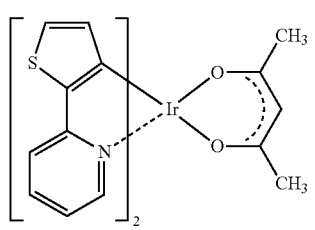 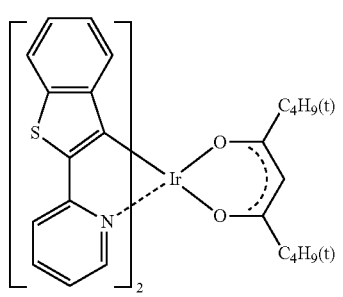

[Chemical Formula 62]
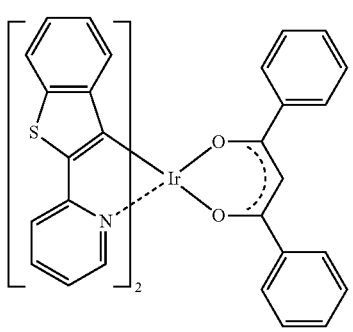 Ir-7
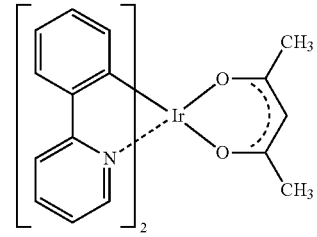 Ir-8
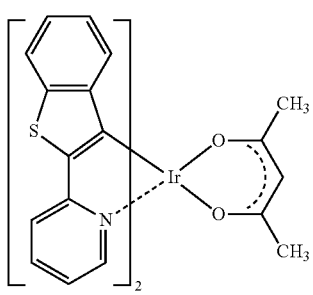 Ir-9
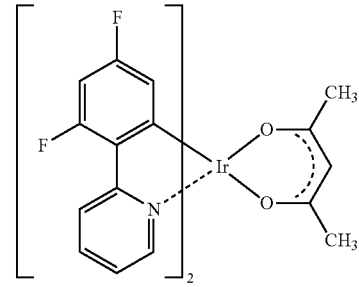 Ir-10
Ir-11
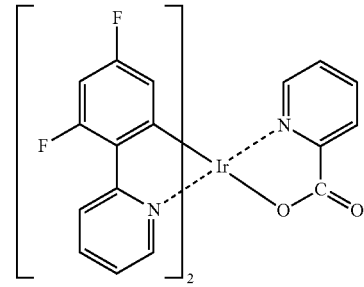 Ir-12
Ir-13
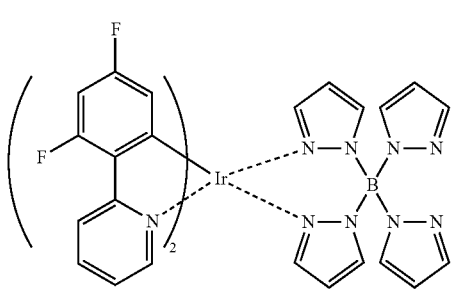 
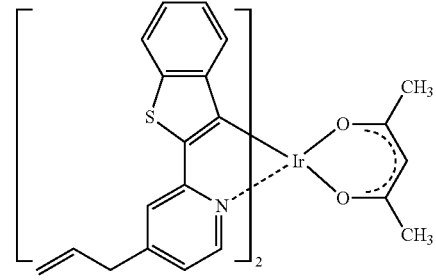 Ir-14
[Chemical Formula 63]
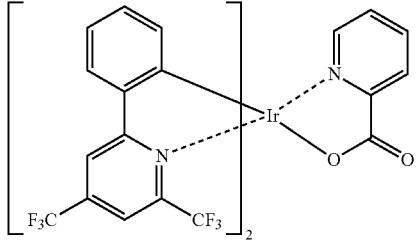 Ir-15
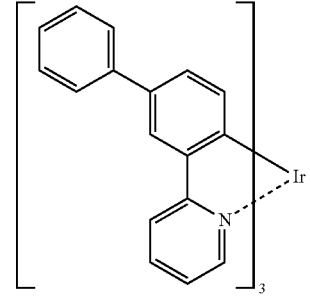 Ir-16

-continued
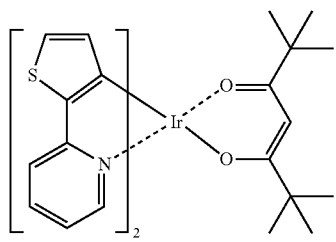
Ir-17
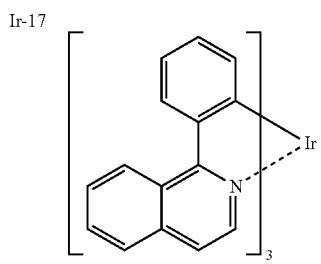
Ir-18
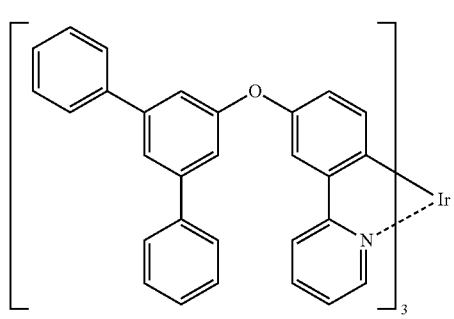
Ir-19
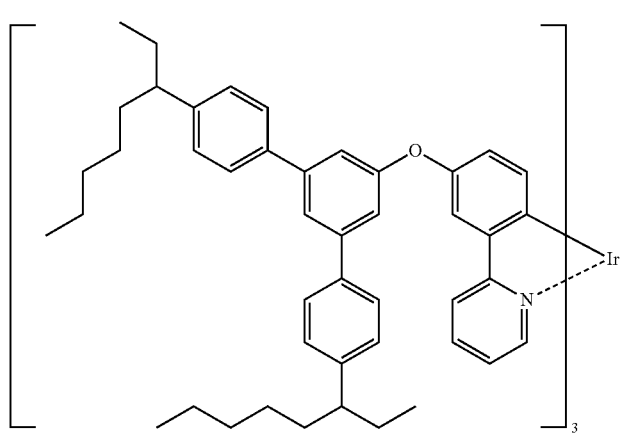
Ir-20
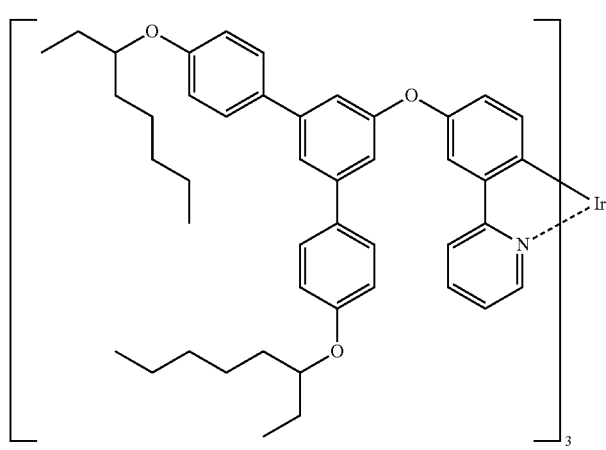
Ir-21

-continued
[Chemical Formula 64]
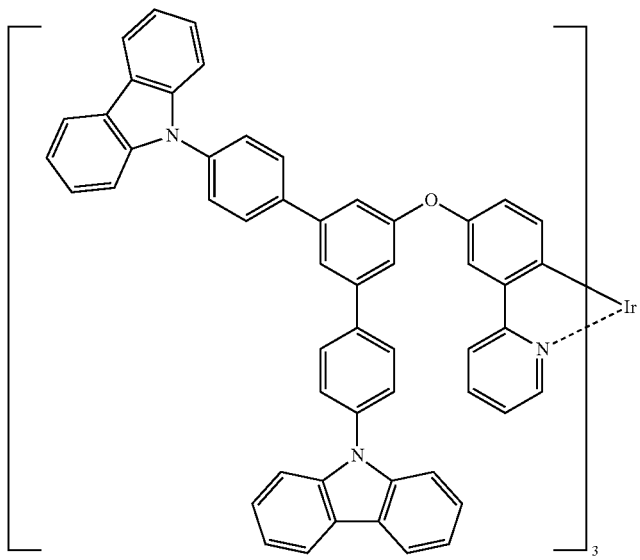
Ir-22
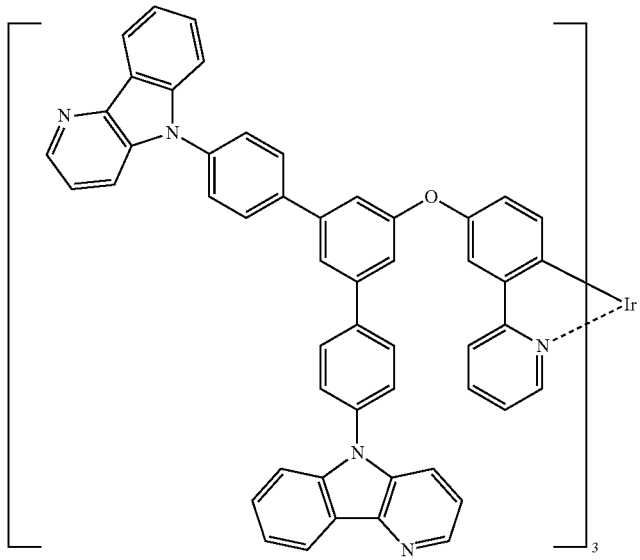
Ir-23
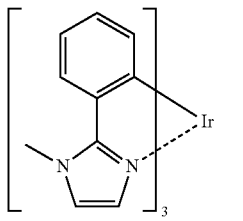
Ir-24
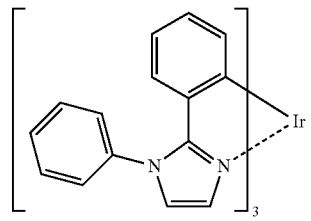
Ir-25
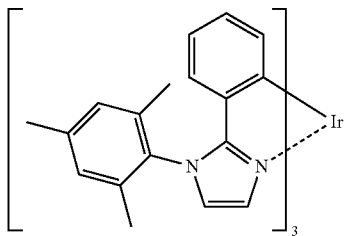
Ir-26

[Chemical Formula 65]
Ir-27
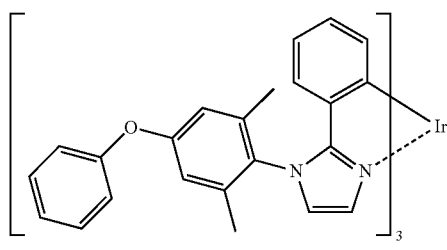
Ir-28
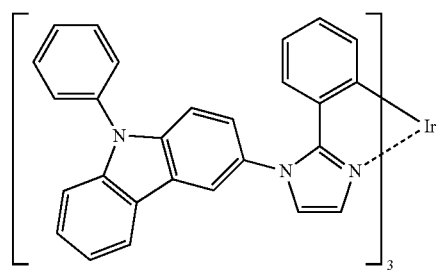
Ir-29
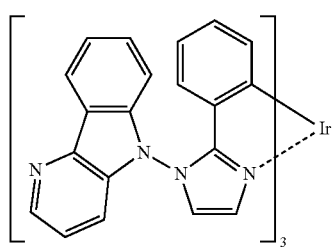
Ir-30
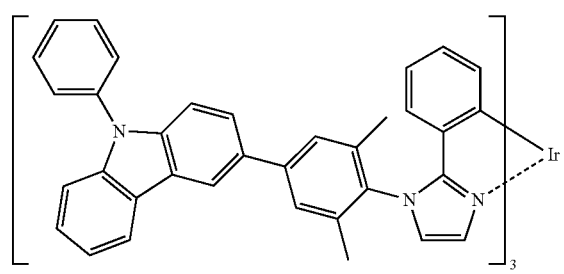
Ir-31
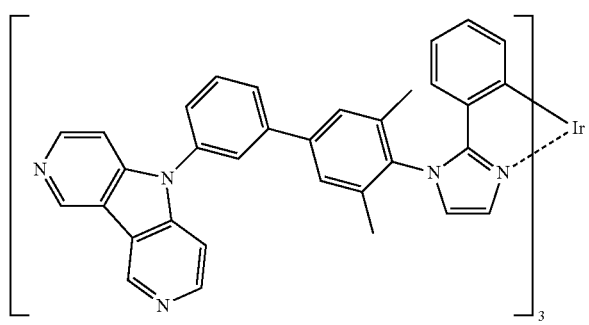
Ir-32
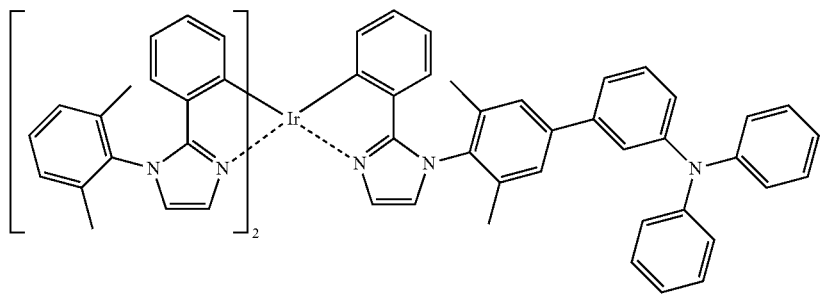
Ir-33
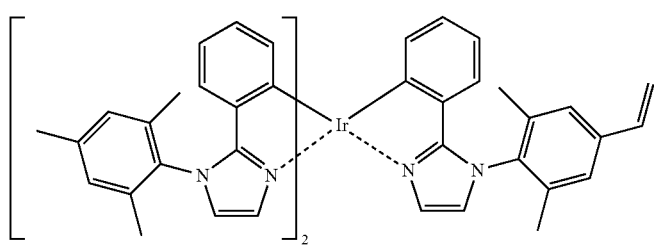

[Chemical Formula 66]
Ir-34 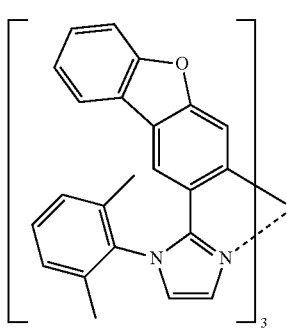 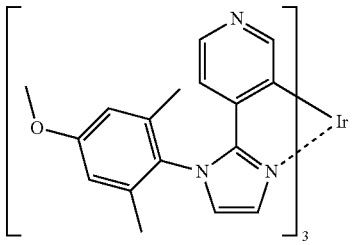 Ir-35
Ir-36 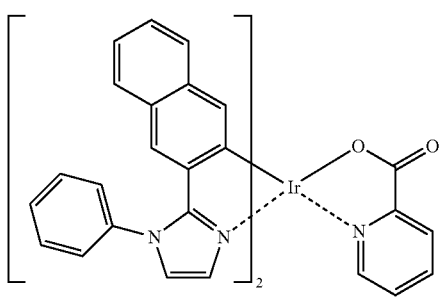 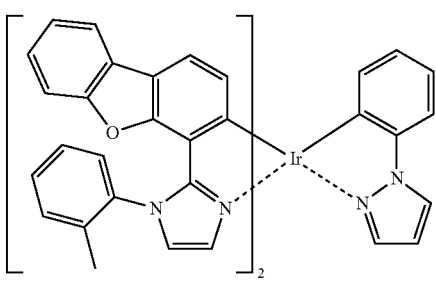 Ir-37
Ir-38 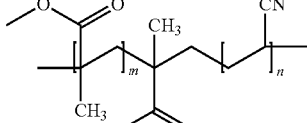
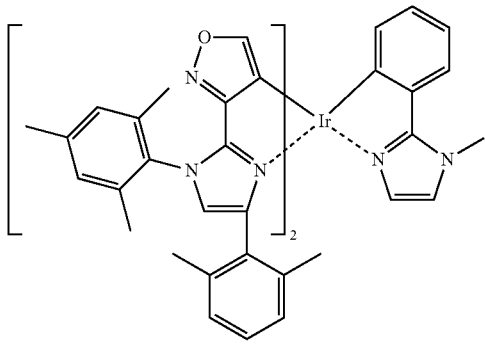 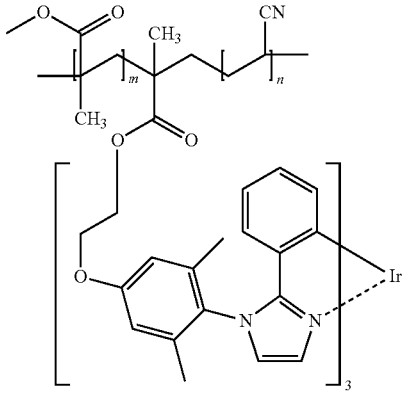 Ir-39
[Chemical Formula 67]
Ir-40 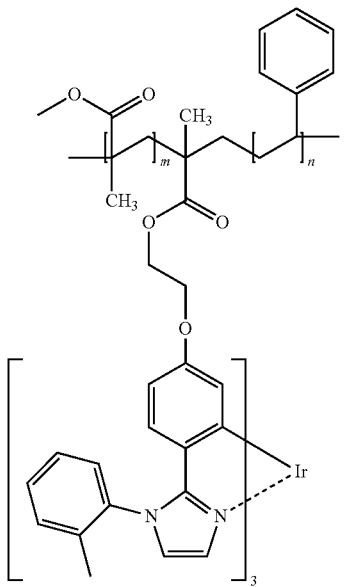 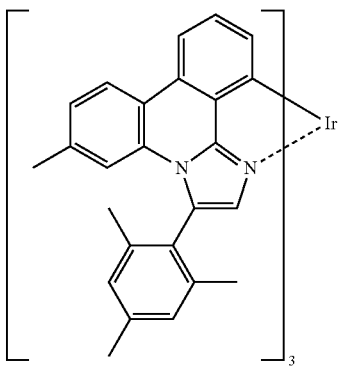 Ir-41

Ir-42

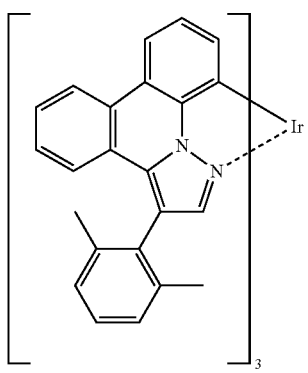

Ir-43

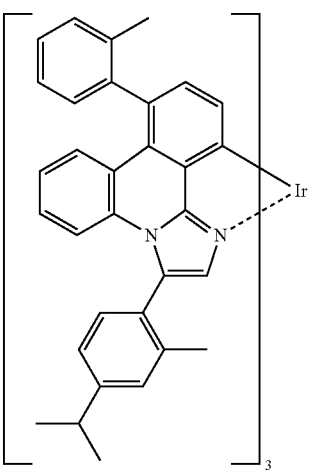

Ir-44

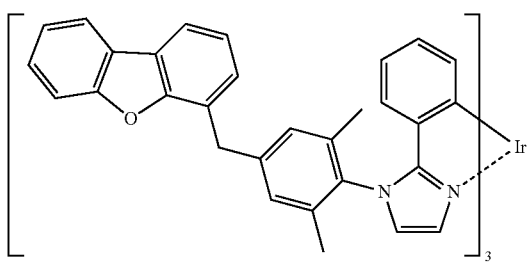

Ir-45

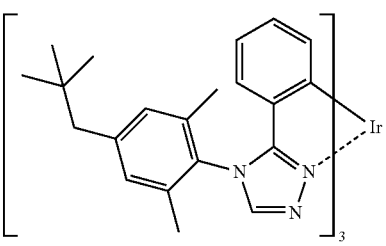

The aforesaid phosphorescent compounds (also referred to as phosphorescent metal complexes or the like) can be synthesized by employing methods described co documents such as Organic Letter, vol. 3, No. 16, pp, 2579-2581 (2001); Inorganic Chemistry, vol. 30, No. 8, pp. 1685-1687 (1991); J. Am. Chem. Soc., vol. 123, pp. 4304 (2001); Inorganic Chemistry, vol. 40, No. 7, pp. 1704-1711 (2001); Inorganic Chemistry, vol. 41, No. 12, pp, 3055-3066 (2002); New Journal of Chemistry, vol. 26, pp. 1171 (2002); and European Journal of Organic Chemistry, vol. 4, pp. 6935-709 (2004); and reference documents described in these documents.

(Fluorescent Material)

Examples of the fluorescent material include a coumarin dye, a pyran dye, a cyanine dye, a chloconium dye, a squarylium dye, an oxobenzanthracene dye, a fluorescein dye, a rhodamine dye, a pyrylium dye, a perylene dye, a stilbene dye, a polythiophene dye, a rare earth complex based phosphor and the like.

The organic EL element according to the present invention may also have, as constituent layers, a blocking layer (i.e., a hole blocking layer (not shown) and an electron blocking layer (not shown)), an injecting layer (i.e., an electron injecting layer (not shown) and a hole injecting layer (not shown)), and the like.

(Blocking Layer: Hole Blocking Layer and Electron Blocking Layer)

As described above, a blocking layer is a layer provided according to necessity in addition to the basic constituent layers of the thin-film of the organic compound. Examples of the blocking layer include a hole blocking layer described in documents such as Japanese Unexamined Patent Application Publication Nos. 11-204258 and 11-204359 and pp. 273 of "Organic EL Element and Front of Industrialization thereof" (Nov. 30, 1998, published by N. T. S Co., Ltd.)".

The hole blocking layer has, in a broad sense, a function of the electron transporting layer 7. The hole blocking layer is made of a hole blocking material having a function of transporting electrons with very little capability of transporting holes; the hole blocking layer transports electrons while blocking holes, so that probability of recombinations of electrons and holes can be increased. Further, the constitution of the electron transporting layer 7 (which is to be described later) can be used as the hole blocking layer according to necessity. It is preferred that the hole blocking layer is arranged adjacent to the light emitting layer 6.

On the other hand, the electron blocking layer has, in a broad sense, a function of the hole transporting layer 5. The electron blocking layer as made of a material having a function of transporting holes with very little capability of transporting electrons; the electron blocking layer transports holes while blocking electrons, so that probability of recombination of electrons and holes can be increases. Further, the constitution of the hole transporting layer 5 (which is to be described later) can be used as the electron blocking layer according to necessity. The thickness of the hole blocking layer of the present invention is preferably within a range from 3 to 100 nm, and further preferably within a range from 5 to 30 nm.

Injecting Layer: Electron Injecting Layer and Hole Injecting Layer)

An injecting layer is a layer arranged between an electrode and an organic layer (i.e., light emitting layer) to decrease a driving voltage and to improve brightness of emitted light; the details of the injecting layer are described in "Electrode Material" (pp. 123-166, Part 2, Chapter 2 of "Organic EL Element and Front of Industrialization thereof" Nov. 30, 1998, published by N. T. S Co., Ltd.), and examples of the injecting layer include a hole injecting layer (FIG. 1) and an electron injecting layer.

The injecting layer can be provided according to necessity. As described above, the injecting layer may be provided between the anode and the light emitting layer or the hole transporting layer, and between the cathode and the light emitting layer or the electron transporting layer.

The details of the hole injecting layer is also described in documents such as Japanese Unexamined Patent Application Publication Nos. 9-45479, 9-260062 and 8-288069, and concrete examples of the hole injecting layer include a layer of a phthalocyanine represented by copper phthalocyanine, a layer of an oxide represented by vanadium oxide, a layer of an amorphous carbon and a layer of a polymer employing conductive polymer such as polyaniline (emeraldine), polythiophene and the like.

The details of the electron injecting layer is also described in documents such as Japanese Unexamined Patent Application Publication Nos. 6-325871, 9-17574 and 10-74586, and concrete examples of the electron injecting layer include a layer of a metal represented by strontium, aluminum or the like; a layer of an alkali metal halide represented by potassium fluoride; a layer of an alkali earth metal compound represented by magnesium fluoride; and a layer at an oxide represented by molybdenum oxide. It is preferred that the electron injecting layer is a very thin film, and it is preferred that the thickness electron injecting layer is within a range from 1 nm to 10 μm depending on the material thereof.

(Hole Transporting Layer)

A hole transporting layer is made of a hole transporting material having a function of transporting holes; and, in a broad sense, a hole injecting layer and an electron blocking layer are included in the hole transporting layer. One hole transporting layer or a plurality of hole transporting layers can be provided.

The hole transporting material is a material either having a capability of injecting or transporting holes, or having a barrier property against electrons; the hole transporting material may either be an organic material or an inorganic material. Examples of the hole transporting material include a triazole derivative, an oxadiazole derivative, an imidazole derivative, a polyarylalkane derivative, a pyrazoline derivative, a pyrazolone derivative, a phenylenediamine derivative, an arylamine derivative, an amino-substituted, chalcone derivative, an oxazole derivative, a styrylanthracene derivative, a fluorenone derivative, a hydrazone derivative, a stilbene derivative, a silazane derivative, an aniline copolymer, a conductive oligomer such as a thiophene oligomer, and the like.

Although the aforesaid, compounds can be used as the hole transporting material, it is preferred that a porphyrin compound, as aromatic tertiary amine compound or a styrylamine compound is used as hole transporting material, and wherein it is particularly preferred that an aromatic tertiary amine compound is used as the hole transporting material.

Typical examples of the aromatic tertiary amine compound and the styrylamine compound include: N,N,N',N'-tetraphenyl-4,4'-diaminophenyl; N,N'-diphenyl-N,N'-bis-(3-methylphenyl)-[1,1'-biphenyl]-4,4'-diamine (TDP); 2,2-bis(4-di-p-tolylaminophenyl)propane; 1,1-bis(4-di-p-tolylaminophenyl)cyclohexane; N,N,N',N'-tetra-p-tolyl-4,4'-diaminobiphenyl; 1,1-bis(4-di-p-tolylaminophenyl)-4-phenylcyclohexane; bis(4-dimethylamino-2-methyl)phenylmethane; bis(4-di-p-tolylaminophenyl)phenylmethane; N,N'-diphenyl-N,N'-di(4-methoxyphenyl)-4,4'-diaminobiphenyl; N,N,N',N'-tetraphenyl-4,4'-diaminodiphenylether; 4,4'-bis(diphenylamino)quadriphenyl; N,N,N-tri(p-tolyl)amine; 4-(di-p-tolylamino)-4'-[4-(di-p-tolylamino)styryl]stilbene; 4-N,N-diphenylamino-(2-diphenylvinyl)benzene; 3-methoxy-4'-N,N-diphenylaminostilbene; and N-phenylcarbazole. Typical examples of the aromatic tertiary amine compound and the styrylamine compound further include: a compound having two condensed aromatic rings in a molecule described in U.S. Pat. No. 5,061,569, such as 4,4'-bis[N-(1-naphthyl)-N-phenylamino]biphenyl (NDP); and 4,4',4"-tris[N-(3-methylphenyl)-N-phenylamino]triphenylamine (MTDATA) in which three triphenylamine units are bonded in a star burst form described in Japanese Unexamined Patent Application Publication No. 4-308688.

Further, a polymer material in which any of these materials is introduced into a polymer chain or a polymer material in which a polymer main chain is constituted by any of these materials, may also be used. Further, inorganic compounds such as a p-type Si and a p-type SiC may also be used as the hole injecting material and the hole transporting material.

Further, it is also possible to use a so-called p-type hole transporting material described in documents such as Japanese Unexamined Patent Application Publication No. 11-251067 and Applied Physics Letters 80 (2002), pp. 139 by J. Huang et. al. In the present invention, it is preferable to use these materials in order to produce a light-emitting element having high efficiency.

The hole transporting layer 5 can be formed by forming a thin film or the aforesaid hole transporting material by employing a known method such as a vacuum deposition method, a spin coating method, a casting method, a printing method (which includes an ink-jet method), a LB method or the like. The thickness of the hole transporting layer 5 is not particularly limited; however, the thickness of the hole transporting layer 5 is typically within a range about from 5 nm to 5 μm, preferably within a range from 5 nm to 200 nm. The hole transporting layer may have a single layer structure formed of one type of the aforesaid materials, or formed of two or more types of the aforesaid materials.

Further, it is also possible to dope impurities into the material of the hole transporting layer to improve p-property. Examples of doping impurities into the material of the hole transporting layer include those described in documents such as Japanese Unexamined Patent Application Publication Nos. 4-297076, 2000-196140 and 2001-102175 and J. Appl. Phys., 95, 5773 (2004).

It is preferred to dope impurities into the material of the hole transporting layer, because improved p-property makes it possible to produce an element which consumes lower electric power.

Anode

The material having been mentioned when describing the cathode constituting the aforesaid transparent conductivity may be used for the anode (i.e., opposite electrode) paired with the cathode; a material having a metal, an alloy, an electrically conductive compound or a mixture thereof as an electrode substance may also be used for the anode.

Concrete examples of the electrode substance include sodium, sodium-potassium alloy, magnesium, lithium, silver, ITO (indium tin oxide), magnesium/copper mixture, magnesium/argentum mixture, magnesium/aluminum mixture, magnesium/indium mixture, aluminum/aluminum oxide ($Al_2O_3$) mixture, indium, lithium/aluminum mixture, rare earth metal and the like.

The opposite electrode can be produced by forming the aforesaid electrode substance into a thin film by a method such as evaporation, sputtering or the like. The sheet resistance of the opposite electrode is preferably several hundreds Ω/□ or less; and the thickness thereof is generally within a range from 10 nm to 5 μm, preferably within a range from 50 nm to 200 nm.

Supporting Substrate

Examples of the material of the supporting substrate (also referred to as base material, base body, substrate, support or the like hereinafter) possible to be used in the organic EL element of the present invention include, but not limited to, glass, plastic and the like. Further, the supporting substrate may be either transparent or opaque. However, if light is extracted from the supporting substrate, it is preferred that the supporting substrate is transparent. Examples of the material preferably to be used as the transparent supporting substrate include glass, quartz, and transparent resin films. A particularly preferred supporting substrate is a resin film capable of imparting flexibility to the organic EL element 1A.

Examples of materials for such resin film include polyesters such as polyethylene terephthalate (PET) and polyethylene naphthalate (PEN), polyethylene, polypropylene, cellophane, cellulose esters and their derivatives such as cellulose diacetate, cellulose triacetate (TAC), cellulose acetate butylate, cellulose acetate propionate (CAP), cellulose acetate phthalate, and cellulose nitrate, polyvinylidene chloride, polyvinylalcohol, polyethylenevinylalcohol, syndiotactic polystyrene, polycarbonate, norbornane resin, polymethylpentene, polyetherketone, polyimide, polyether sulfone (PES), polyphenylene sulfide, polysulfones, polyether imide, polyetherketone imide, polyamide, fluorine resin, nylon, polymethyl methacrylate, acryl or polyarylates, and cycloolefin resins such as APTON (trade name, manufactured by JSR Corp.) or APEL (trade name, manufactured by Mitsui Chemicals Inc.).

An inorganic or organic coating film or a hybrid coating film composed of the both may be formed on the surface of the resin film. It is preferred that the coating film is a barrier film having a water vapor permeability of 0.01 $g/(m^2 \cdot 24\ h)$ or less (at temperature of 25±0.5° C. and relative humidity of (90±2)% RH) measured by a method in conformity with JIS K 7129-1992, and it is further preferred that the coating film is a high barrier film having an oxygen permeability of $10^{-3}$ $ml/(m^2 \cdot 24\ h \cdot atm)$ or less and a water vapor permeability of $10^{-5}$ $g/(m^2 \cdot 24\ h)$ or less measured by a method in conformity with JIS K 7126-1987.

Any material capable of preventing penetration of substances that cause the element to degrade, such as moisture, oxygen and the like, may be used to form the barrier film, and examples of such material include silicon oxide, silicon dioxide, silicon nitride and the like. Further, in order to reduce the fragility of the barrier film, it is more preferred that the barrier film has a laminate structure composed of inorganic layer(s) and organic material layer(s) (i.e., organic layer(s)). There is no particular limitation on the order of laminating the inorganic layer and organic layer; however, it is preferred that the both layers are alternately laminated multiple times.

There is no particular limitation on the method of forming the barrier film. For example, the barrier film may be formed by a vacuum deposition method, a sputtering method, a reactive sputtering method, a molecular beam epitaxy method, a cluster ion beam method, an ion plating method, a plasma polymerization method, an atmospheric pressure plasma polymerization method, a plasma CVD method, a laser CVD method, a thermal CVD method, a coating method or the like; and it is particularly preferred that the barrier film is formed by an atmospheric pressure plasma polymerization method described in Japanese Unexamined Patent Application Publication No. 2004-68143.

Examples of the opaque supporting substrate include a metal plate such as an aluminum plate, a stainless steel plate or the like, a film, an opaque resin substrate, a ceramic substrate and the like.

Sealing

Examples of the sealing means used in the present invention include a method of bonding a sealing member to the electrode and supporting substrate 2 with an adhesive.

The sealing member may be disposed so as to cover a light emitting region of the organic EL element, and may have a concave plate shape or a flat plate shape. There is no restriction on transparency and electrical insulation properties of the sealing member. The electrode is provided in the sealing member, and may be provided in a manner in which the electrode can be electrically connected with the organic EL element.

Concrete examples of the sealing member include a glass substrate, a polymer substrate/film, a metal substrates/film and the like. Examples of the glass substrate include soda-lime glass substrate, barium/strontium-containing glass substrate, lead glass substrate, aluminosilicate glass substrate, borosilicate glass substrate, barium borosilicate glass substrate, quartz substrate, and the like. Examples of the polymer substrate include polycarbonate substrate, acryl resin substrate, polyethylene terephthalate substrate, polyether sulfide substrate, polysulfone substrate and the like. Examples of the metal substrate include a substrate of one or more kinds of metals selected from the group consisting of stainless steel, iron, copper, aluminum, magnesium, nickel, zinc, chromium, titanium, molybdenum, silicon, germanium, tantalum, and alloys thereof.

In the present, invention, the polymer film or the metal film is preferably used since it enables to reduce the thickness of the element.

Further, it is preferred that the polymer film has an oxygen permeability of $1 \times 10^{-3}$ $ml/(m^2 \cdot 24\ h \cdot atm)$ or less measured by a method in conformity with JIS K 7126-1987 and a water, vapor permeability of $1 \times 10^{-3}$ $g/(m^2 \cdot 24\ h)$ or less (at temperature of 25±0.5° C. and relative humidity of (90±2) % RH) measured by a method in conformity with JIS K 7129-1992.

In the case where the sealing member is to be formed into a concave shape, the sealing member is processed by sand blasting, chemical etching or the like.

Concrete examples of the adhesive include a photo-curable or thermo-curable adhesive agent containing a reactive vinyl group such as an acrylic acid oligomer or a methacrylic acid oligomer, and a moisture curable adhesive agent such as 2-cyanoacrylate.

Concrete examples of the adhesive also include an epoxy based thermally and chemically (two liquid type) curable adhesive agents; a hot-melt type polyamide, polyester or polyolefin adhesive agents; and a cationic curable type UV-curable epoxy adhesive.

Incidentally, since there is a possibility that the organic EL element might be degraded by heat treatment, it is preferred that an adhesive possible to be cured in a temperature from room temperature to 80° C. is used. Further, a drying agent may be dispersed in the adhesive.

The adhesive may be coated onto the sealing portion either by a commercially available dispenser, or by printing such as screen printing.

Further, it is preferred that an inorganic or organic layer is formed as a sealing film on the outer side of the electrode opposite to the supporting substrate 2 with the organic layer interposed therebetween (i.e., the cathode 8 in FIG. 1), so as to cover the electrode and the organic layer, wherein the sealing film contacts the supporting substrate 2. In such a case, any material capable of preventing penetration of substances that cause the element to degrade, such as moisture, oxygen and the like, may be used to form such film, and examples of such material include silicon oxide, silicon dioxide, silicon nitride and the like.

Further, in order to reduce the fragility of such film, it is preferred that the film has a laminate structure composed of inorganic layers and organic layers.

There is no particular limitation on the method of forming the aforesaid film. For example, the aforesaid film may be formed by a vacuum deposition method, a sputtering method, a reactive sputtering method, a molecular beam epitaxy method, a cluster ion beam method, an ion plating method, a plasma polymerization method, an atmospheric pressure plasma polymerization method, a plasma CVD method, a laser CVD method, a thermal CVD method, a coating method or the like.

It is preferred that an inert gas, such as nitrogen, argon or the like, or an inert liquid, such as fluorinated hydrocarbon, silicone oil or the like, is injected, in the form of gas or liquid phase, into the space between the sealing member and the light emitting region of the organic EL element. Alternatively, the space between the sealing member and the light emitting region of the organic EL element may be in a vacuum state, or may have a hygroscopic compound enclosed therein.

Examples of the hygroscopic compound include a metal oxide (such as sodium oxide, potassium oxide, calcium oxide, barium oxide, magnesium oxide and aluminum oxide), a sulfate (such as sodium sulfate, calcium sulfate, magnesium sulfate and cobalt sulfate), a metal halide (such as calcium chloride, magnesium chloride, cesium fluoride, tantalum fluoride, cerium bromide, magnesium bromide, barium iodide and magnesium iodide), a perchloric acid, (such as barium perchlorate and magnesium perchlorate) and the like; wherein if the sulfate, the metal halide or the perchlorate is used, anhydrides thereof will be preferable.

Protective Film, Protective Plate

In order to increase the mechanical strength of the element, a protective film or protective plate may be provided on (or on one outer side of) the sealing film opposite to the supporting substrate with the organic layer interposed therebetween. It is preferred that the protective film or protective plate is provided particularly in the case where sealing is carried out by forming the aforesaid sealing film, since in that case the mechanical strength of the element is not necessarily high. Examples of the material possible to be used as the protective film or protective plate include the same glass substrate, polymer substrate/film, metal substrate/film or the like as has been used for performing the aforesaid sealing processing; however, it is preferred that the polymer film is used in order to reduce weight and film-thickness.

Method of Producing Organic EL Element

As an example of method of producing the organic EL element according to the present invention, a method of producing an organic EL element composed of supporting substrate/anode/hole injecting layer/hole transporting layer/light emitting layer/electron transporting layer/cathode will be described below.

First, a thin film formed of a desired electrode material (for example, an anode material) is formed on a suitable supporting substrate by depositing, sputtering or the like so that the film thickness of the thin film is 1 μm or less, preferably 10 nm to 200 nm, so as to produce an anode. Next, thin-films containing organic compound (as element materials), i.e., the hole injecting layer, the hole transporting layer, the light emitting layer, the electron transporting layer and the like, are formed on the anode.

Examples of methods for reducing the thickness of the thin-films containing organic compound include a spin coating method, a casting method, an ink-jet method, a deposition method, a printing method or the like; a vacuum deposition method or a spin coating method is particularly preferable because by such method, it is easy to form a uniform film and unlikely to cause pinholes. Further, the individual layers of the thin-films may each be formed by a different film-forming method from each other.

When the deposition method is used to form the films, the deposition conditions vary depending on the type of the compound used; generally, it is preferred that the boat heating temperature is selected in a range from 50° C. to 450° C., the vacuum degree is selected in a range from $10^{-6}$ Pa to $10^{-2}$ Pa, the deposition rate is selected in a range from 0.01 nm/sec to 50 nm/sec, the substrate temperature is selected in a range from −50° C. to 300° C., and the film thickness to selected in a range from 0.1 μm to 5 μm.

After these layers have been formed, the cathode according to the present invention is formed by a deposition method, and thereby a desired organic EL element is obtained.

It is also possible to form films in a reverse order, i.e., to form films on the supporting substrate in an order of: the cathode of the present invention, the electron transporting layer, the light emitting layer, the hole transporting layer, the hole injecting layer, the anode.

In the case where a DC voltage is applied to the organic EL element produced in the above manner, when a voltage of about 2 V to 40 V is applied wherein electrode "+" is connected to the anode 3 of the organic EL element and electrode "−" is connected to the cathode of the organic EL element, light emission can be observed. Also, an AC voltage may be applied to the organic EL element, wherein the AC voltage may have any waveform.

It is preferred that the organic EL element of the present invention is produced in a manner in which the layers from the hole injecting layer to the cathode are continuously formed with one vacuuming operation; however, it is also possible to take out the element outing production to perform different, film-forming method. In such a case, necessary considerations should be taken into account, such as performing the production in dry inert gas atmosphere.

Application

As described above, the organic EL element of the present invention may be used as a planar light-emitting body; in addition, the organic EL element of the present invention may also be used as a display device, a display, or various light emitting sources. Examples of the light emitting source include, but not limited to, an illumination device (such as a home lighting fixture, a car lighting fixture or the like), a backlight for a timepiece or a liquid crystal, a signboard for advertisement, a traffic light, a light source for an optical storage medium, a light source for an electrophotographic copier, a light source for an optical communication processor and a light source for an optical sensor; particularly, the light emitting source can be effectively used as a backlight for a liquid crystal display device combined with a color filter, and as a light source for illumination.

Further, the organic EL element may either be used as a kind of lamp such as an illuminating source, an exposing source or the like, or be used as a projection device where an image is projected, a display device (a display) where a still image or dynamic image is directly viewed, or the like.

In the case where the organic EL element is used as a display device for replaying dynastic image, the driving method may either be a simple matrix driving method (i.e., passive matrix driving method) or an active matrix driving method. Further, it is possible to produce a full color display device by using two or more organic EL elements or the present invention each having different emission color.

An illumination device, as an example of the application, will be described below.

Illumination Device

The illumination device of the present invention has an organic EL element described above.

Note that the illumination device of the present invention may be used as an organic EL element obtained by providing a resonator structure to the aforesaid organic EL element.

Examples of the intended use of such organic EL element having the resonator structure include, but not limited to, a light source for an optical storage medium, a light source for an electrophotographic copier, a light source for an optical communication processor, a light source for an optical sensor and the like. Further, the illumination device may also be used for the aforesaid purpose by laser-oscillating.

Incidentally, the material used in the organic EL element of the present invention may be used for an organic EL element which emits while light (also referred to as a "white organic EL element"). Further, it is also possible to cause a plurality of emission colors to be simultaneously emitted from a plurality of light emitting materials so as to obtain a white light emission by mixed color. The combination of the plurality of emission colors may be a combination including three light emission maximum wavelengths of three primary colors of blue, green and red, or a combination including two light emission maximum wavelengths using the complementary color relationship such as blue and yellow, bluish-green and orange, or the like.

Further, the combination of light emitting materials for obtaining a plurality of emission colors may be a combination of a plurality of materials which emit a plurality of phosphorescent lights or fluorescent lights, or a combination of a light emitting material which emits phosphorescent light or fluorescent light and a dye material which emits light with the light emitted from the light emitting material as exciting light; however, in a white organic EL element, the combination of light emitting materials for obtaining a plurality of emission colors may also be a combinations of a plurality of light-emitting dopants.

It is only necessary to only provide a mask when forming the light emitting layer, the hole transporting layer or the electron transporting layer by a simple arrangement such as coating separation by the mask; since other layers are common layers, no patterning by a mask or the like needs to be carried out, and an electrode film, for example, can be formed on one surface by a deposition method, a casting method, a spin coating method, an ink-jet method, a printing method or the like, and productivity can be improved. With such a method, the organic EL element itself emits white light, unlike a white organic EL device in which a plurality of colors of light-emitting elements are arranged in array.

The light emitting material used in the light emitting layer is not particularly limited; for example, if the light emitting material is used for the back light of a liquid crystal display element, arbitrary light emitting materials may be selected from the metal complexes of the present invention or known light emitting materials and combined to obtain white light in a manner in which the light is matched to the wavelength range corresponding to CF (color filter) characteristics.

By using the white organic EL element described above, it is possible to produce an illumination device which emits white light.

Aspect of Illumination Device of Present Invention

One aspect or the illumination device of the present invention having the organic EL element of the present invention will be described below. FIG. 3 is a cross-sectional view showing one aspect of the illumination device according to the present invention.

As schematically shown in FIG. 3, in an illumination device 20 of the present invention, the organic EL element 1A (1B), which includes the supporting substrate 2 onto; which the anode is formed, the light emitting layer 6 and the cathode 8, is fixed to a sealing glass substrate 21 by a seal material 23 (for example, an epoxy based photo-curable adhesive (LUX-TRACK LC0629B manufactured by Toagosei Co., Ltd.)). The organic EL element 1A (1B) fixed to the glass substrate 21 is sealed by the glass substrate 21, the glass case 22 and the seal material 23. The seal material used to fix the organic EL element 1A (B) may be used as the seal material 23. The organic EL element 22 has nitrogen gas 24 enclosed therein so that the organic EL element 1A (B) does not contact with air. Thus, it is preferred that the sealing operation with the glass case 21 is performed in a glove box under a nitrogen atmosphere (an atmosphere of high purely nitrogen gas having a purity of 99.999% or higher). Further, a hygroscopic compound 25 is provided inside the glass case 22.

EXAMPLES

The present invention will be concretely described with the following examples; however, the present invention is not limited to these examples.

Production or Dual Emission Type Organic EL Element

Organic EL elements 1 to 63 shown in Tables 1 to 3 are produced so that they each have a light-emitting area of 5 cm×5 cm.

[Production or Organic EL Element 1]
(Formation of Anode)

An ITO film was formed on a transparent glass supporting substrate by a sputtering method under a condition so that the thickness of the ITO film was 100 nm, and then patterning was performed to form an anode made of ITO layer. Next, the substrate having the ITO layer formed thereon was subjected to ultrasonic cleaning with isopropyl alcohol, then dried with dry nitrogen gas, and then subjected to UV ozone cleaning for 5 minutes.

(Formation of Layers from Hole Injecting Layer to Electron Injecting Layer)

The supporting substrate having the ITO layer formed thereon was fixed to a substrate holder of a commercial vacuum deposition device. Then, the below-mentioned HI-1, HI-2, α-NPD, compound H4 (simple referred to as "H4" hereinafter), compound Ir-4 (simply referred to as "Ir-4" hereinafter), BAlq, Alq$_3$, Lithium quinolate, lithium fluoride, potassium fluoride were respectively placed in tantalum resistive heating boats, and the tantalum resistive heating boats were mounted on a first vacuum chamber of the vacuum deposition device. Incidentally, α-NPD, Balq, and Alq$_3$ have the following structure. Hereinafter, in the production of organic EL elements 2 to 63, necessary material is previously changed timely and set to the tantalum resistive heating boat.

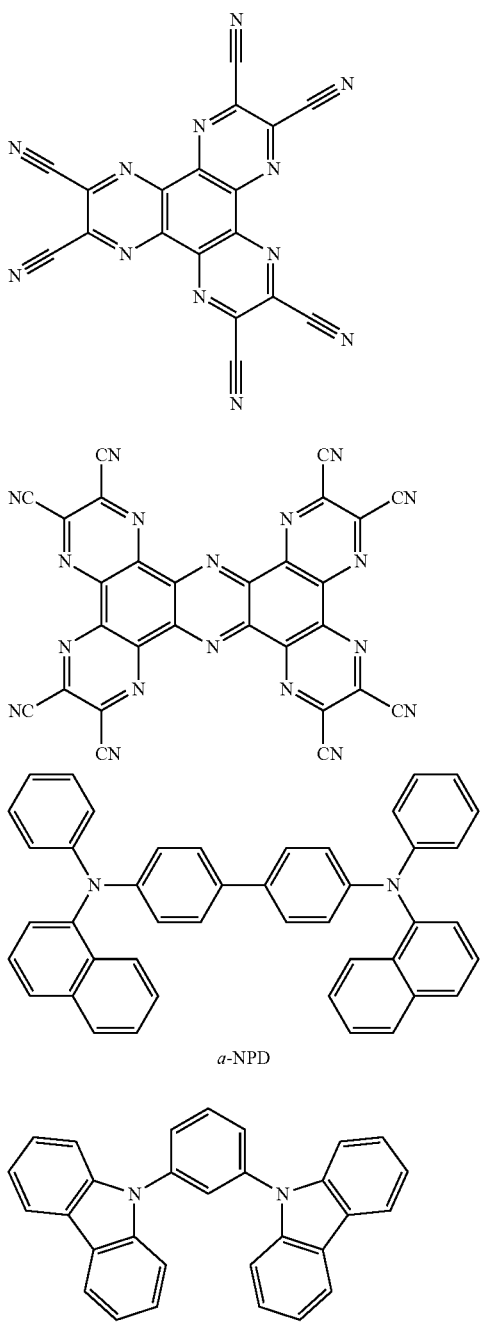

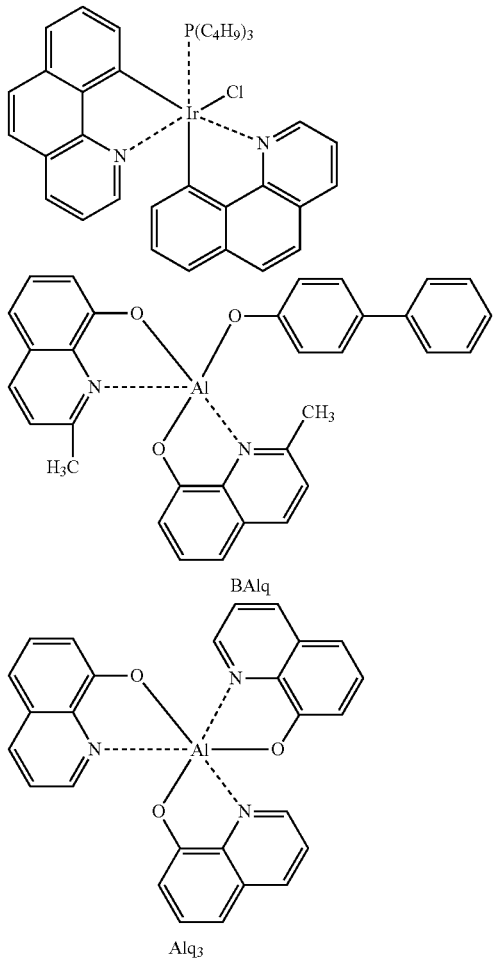

Further, silver was placed in a tungsten resistive heating boat, indium was placed in a molybdenum resistive heating boat, and the tungsten resistive heating boat and the molybdenum resistive heating boat were mounted on a second vacuum chamber of the vacuum deposition device.

First, the pressure of the first vacuum chamber was reduced to $4 \times 10^{-4}$ Pa, and then the healing boats having HI-1 and HI-2 placed therein were electrically heated to form a hole injecting layer having a total film thickness of 20 nm on the ITO layer, wherein electric current was controlled so that the deposition rate or each of HI-1 and HI-2 became 0.05 nm/sec.

Next, the heating boat having α-NPD placed therein was electrically heated at a deposition rate of 0.1 nm/sec to 0.2 nm/sec to form a hole transporting layer having a film thickness of 20 nm on the ITO layer.

Further, the heating boat having H4 placed therein and the heating boat having Ir-4 placed therein were each independently electrically heated to form a light emitting layer having a film thickness of 30 nm, wherein ratio of the deposition rate of the H4 (which was a light-emitting host) to the deposition rate of the Ir-4 (which was a light-emitting dopant) was adjusted to 100:6.

Next, the heating boat having Balq placed therein was electrically heated at a deposition rate of 0.1 nm/sec to 0.2 nm/sec to form a hole blocking layer having a film thickness of 10 nm.

Further, the heating boat having Alq$_3$ placed therein was electrically heated at a deposition rate or 0.1 nm/sec to 0.2 nm/sec to form an electron transporting layer having a film thickness of 20 nm.

Further, the heating boat having lithium fluoride placed therein was electrically heated at a deposition rate of 0.01 nm/sec to 0.02 nm/sec to form an electron injecting layer having a film thickness of 1 nm.

(Formation of Cathode)

Next, the element in which the layers up to the electron injecting layer had been formed was transferred to the second vacuum chamber while maintaining the vacuum state. After the pressure of the second vacuum chamber was reduced to 4×10$^{-4}$ Pa, the heating boat having silver placed therein was electrified to form a silver electrode layer having a film thickness of 10 nm to obtain a cathode, and thereby the organic EL element 1 was produced.

(Sealing of Organic EL Element)

Finally, the organic EL element 1 obtained above was cut into a size so that the extraction electrode portion thereof was exposed, an epoxy adhesive Scotch Weld EW2083 (trade name, produced by Sumitomo 3M Ltd.) was applied to the whole surface of an alkali-free glass for sealing which has a thickness of 0.7 mm, and the organic EL element 1 was brought info pressure-contact with the alkali-free glass so that the both were bonded to each other in a manner that no air bubble is left therein, and then the result was sealed by being heated at 85° C. for 60 minutes to produce the organic EL element 1.

[Production of Organic EL Element 2]

(Formation of Anode to Cathode)

The layers from the anode to the cathode were formed by the same method as that of the organic EL element 1.

(Formation of Adjacent Layer)

Next, the obtained element was transferred to the first vacuum chamber again, and the heating boat having Alq$_3$ placed therein was electrically heated at a deposition rate of 0.1 nm/sec to 0.2 nm/sec to form an adjacent layer having a film thickness of 100 nm and thereby the organic EL element 2 was obtained.

(Sealing of Organic EL Element)

The obtained organic EL element 2 was sealed in the same manner as the organic EL element 1 to obtain the organic EL element 2.

Further, Alq$_3$ was deposited separately on a quartz glass to obtain a film of Alq$_3$. The film thickness of the obtained film was 50 nm, and the refractive index of the obtained film was measured by spectroscopic ellipsometry method.

[Production of Organic EL Element 3]

An organic EL element 3 was produced in the same manner as the organic EL element 1 except that the film thickness of the cathode was changed from 10 nm to 8 nm with respect to the organic EL element 1. The obtained organic EL element 3 was sealed in the same manner as the organic EL element 1 to obtain the organic EL element 3.

[Production of Organic EL Element 4]

(Formation of Anode to Cathode)

The layers from the anode to the cathode were formed by the same method as that of the organic EL element 3.

(Formation of Adjacent Layer)

Next, the obtained element was transferred to the first vacuum chamber again, and the heating boat having Alq$_3$ placed therein was electrically heated at a deposition rate of 0.1 nm/sec to 0.2 nm/sec to form an adjacent layer having a film thickness of 15 nm, and thereby the organic EL element 4 was produced. The obtained organic EL element 4 was sealed in the same manner as the organic EL element 1 to obtain the organic EL element 4.

[Production of Organic EL Elements 5 to 8]

Organic EL elements 5 to 8 were produced in the same manner as the organic EL element 4 except that the film thickness of the adjacent layer of each of the organic EL elements 5 to 8 was changed from 15 nm to 30 nm, 50 nm, 80 nm and 100 nm, respectively, with respect to the organic EL element 4. The obtained organic EL elements 5 to 8 were sealed in the same manner as the organic EL element 1 to obtain the organic EL elements 5 to 8.

[Production of Organic EL Elements 9 and 10]

Organic EL elements 9 and 10 were produced in the same manner as the organic EL element 8 except that the film thickness of the cathode of each of the organic EL elements 9 and 10 was changed from 8 nm to 15 nm and 20 nm, respectively, with respect to the organic EL element 8. The obtained organic EL elements 9 and 10 were sealed in the same manner as the organic EL element 1 to obtain the organic EL elements 9 and 10.

[Production of Organic EL Elements 11 to 15]

Organic EL elements 11 to 15 were produced in the same manner as the organic EL element 4 except that the film thickness of the adjacent layer of each of the organic EL elements 11 to 15 was changed from 15 nm to 120 nm, 150 nm, 180 nm, 210 nm and 240 nm, respectively, with respect to the organic EL element 4. The obtained organic EL elements 11 to 15 were sealed in the same manner as the organic EL element 1 to obtain the organic EL elements 11 to 15.

[Production of Organic EL Element 16]

An organic EL element 16 was produced in the same manner as the organic EL element 1 except that the film thickness of the cathode was changed from 10 nm to 4 nm with respect to the organic EL element 1. The obtained organic EL element 16 was sealed in the same manner as the organic EL element 1 to obtain the organic EL element 16.

[Production of Organic EL Element 17]

(Formation of Anode to Cathode)

The layers from the anode to the cathode were formed by the same method as that of the organic EL element 16.

(Formation of Adjacent Layer)

Next, the obtained element was transferred to the first vacuum chamber again, and the heating boat having Alq$_3$ placed therein was electrically heated at a deposition rate of 0.1 nm/sec to 0.2 nm/sec to form an adjacent layer having a film thickness of 100 nm, and thereby the organic EL element 17 was produced. The obtained organic EL element 17 was sealed in the same manner as the organic EL element 1 to obtain the organic EL element 17.

[Production of Organic EL Element 18]

An organic EL element 18 was produced in the same manner as the organic EL element 2 except that the film thickness of the cathode was changed from 10 nm to 1.8 nm with respect to the organic EL element 2. The obtained organic EL element 18 was sealed in the same manner as the organic EL element 1 to obtain the organic EL element 18.

[Production of Organic EL Element 19]

(Production of Anode to Electron Injecting Layer)

The layers from the anode to the electron injecting layer were formed by the same method as that of the organic EL element 1.

(Formation of Cathode)

Next, the element in which the layers up to the electron injecting layer had been formed was transferred to the second vacuum chamber while maintaining the vacuum state. After the pressure of the second vacuum chamber was reduced to 4×10$^{-4}$ Pa, the heating boat having silver placed therein and the heating boat having indium placed therein were each independently electrically heated to form an electrode layer made or silver and indium and having a total film thickness of 10 nm, so as to produce the organic EL element 19, wherein the deposition rate was adjusted so that ratio or indium atom (atm %) became 5%. The obtained organic EL element 19 was sealed in the same manner as the organic EL element 1 to obtain the organic EL element 19.

[Production or Organic EL Element 20]

(Formation of Anode to Cathode)

The layers from anode to cathode were formed by the same method as that of the organic EL element 19.

(Formation of Adjacent Layer)

Next, the obtained element was transferred to the first vacuum chamber again, and the heating boat having $Alq_3$ placed therein was electrically heated at a deposition rate of 0.1 nm/sec to 0.2 nm/sec to form an adjacent layer having a film thickness of 100 nm, and thereby the organic EL element 20 was produced. The obtained organic EL element 20 was sealed in the same manner as the organic EL element 1 to obtain the organic EL element 20.

[Production of Organic EL Element 21]

An organic EL element 21 was produced in the same manner as the organic EL element 19 except that the film thickness of the cathode was changed from 10 nm to 8 nm with respect to the organic EL element 19. The obtained organic EL element 21 was sealed in the same manner as the organic EL element 1 to obtain the organic EL element 21.

[Production of Organic EL Element 22]

(Formation of Anode to Cathode)

The layers from anode to cathode were formed by the same method as that of the organic EL element 21.

(Formation of Adjacent Layer)

Next, the obtained element was transferred to the first vacuum chamber again, and the heating boat having $Alq_3$ placed therein was electrically heated at a deposition rate of 0.1 nm/sec to 0.2 nm/sec to form an adjacent layer having a film thickness of 15 nm, and thereby the organic EL element 22 was produced. The obtained organic EL element 22 was sealed in the same manner as the organic EL element 1 to obtain the organic EL element 22.

[Production of Organic EL Elements 23 to 31]

Organic EL elements 23 to 31 were produced in the same manner as the organic EL element 22 except that the film thickness of the adjacent layer of each of the organic EL elements 23 to 31 was changed from 15 nm to 30 nm, 50 nm, 80 nm, 100 nm, 120 nm, 150 nm, 180 nm, 210 nm and 240 nm, respectively, with respect to the organic EL element 22. The obtained organic EL elements 23 to 31 were sealed in the same manner as the organic EL element 1 to obtain the organic EL elements 23 to 31.

[Production of Organic EL Element 32]

An organic EL element 32 was produced in the same manner as the organic EL element 22 except that the compound constituting the adjacent layer was changed from $Alq_3$ to compound 10 with respect to the organic EL element 22. Further, a film of compound 10 was separately formed on a quartz substrate to produce the organic EL element 32. The film thickness was 50 nm, and the refractive index of the obtained film was measured by spectroscopy ellipsometry method. The obtained organic EL element 32 was sealed in the same manner as the organic EL element 1 to obtain the organic EL element 32.

[(Production of Organic EL Elements 33 to 41]

Organic EL elements 33 to 41 were produced in the same manner as the organic EL element 32 except that the film thickness of the adjacent layer of each of the organic EL elements 33 to 41 was changed from 15 nm to 30 nm, 50 nm, 80 nm, 100 nm, 120 nm, 150 nm, 180 nm, 210 nm and 240 nm, respectively, with respect to the organic EL element 32. The obtained organic EL elements 33 to 41 were sealed in the same manner as the organic EL element 1 to obtain the organic EL elements 33 to 41.

[Production of Organic EL Element 42]

An organic EL element 42 was produced in the same manner as the organic EL element 36 except that the film thickness of the cathode was changed from 10 nm to 1.8 nm with respect to the organic EL element 36. The obtained organic EL element 42 was sealed in the same manner as the organic EL element 1 to obtain the organic EL element 42.

[Production of Organic EL Element 43]

(Formation of Anode to Cathode)

The layers from anode to cathode were formed by the same method as that of the organic EL element 3.

(Formation of $SiO_2$ Layer)

The element in which the cathode had been formed was transferred to a plasma CVD apparatus, while maintaining the vacuum state, to form a $SiO_2$ layer having a film thickness of 100 nm, wherein the applied voltage was adjusted so that the deposition rate became 0.3 nm/sec to 0.6 nm/sec.

Further, a film of the $SiO_2$ was separately formed on a quart substrate. The film thickness was 50 nm, and the refractive index of the obtained film was measured by spectroscopic ellipsometry method. The obtained organic EL element 43 was sealed in the same manner as the organic EL element 1 to obtain the organic EL element 43.

[Production of Organic EL Element 44]

(Formation of Anode to Cathode)

The layers from anode to cathode were formed by the same method as that of the organic EL element 3.

(Formation of Adjacent Layer)

Next, the obtained element was transferred to the first vacuum chamber again, and the heating boat having Lithium quinolate (Liq) placed therein was electrically heated at a deposition rate of 0.1 nm/sec to 0.2 nm/sec to form an adjacent layer having a film thickness of 100 nm, to thereby produce the organic EL element 44.

Further, a film of the Lithium quinolate was separately formed on a quartz substrate. The film thickness was 50 nm, and the refractive index of the obtained film was measured by spectroscopic ellipsometry method. The obtained organic EL element 44 was sealed in the same manner as the organic EL element 1 to obtain the organic EL element 44.

[Production of Organic EL Element 45]

An organic EL element 45 was produced in the same manner as the organic EL element 8 except that the compound constituting the electron injecting layer was changed from lithium fluoride to potassium fluoride, the film thickness of the electron injecting layer was changed from 1 nm to 2 nm, and the compound constituting the adjacent layer was changed from $Alq_3$ to compound 10 with respect to that organic EL element 8. The obtained organic EL element 45 was sealed in the same manner as the organic EL element 1 to obtain the organic EL element 45.

[Production of Organic EL Element 45]

In organic EL element 46 was produced in the same manner as the organic EL element 36 except that the compound constituting the electron injecting layer was changed from lithium fluoride to potassium fluoride, and the film thickness of the electron injecting layer was changed from 1 nm to 2 nm with respect to the organic EL element 36. The obtained organic EL element 46 was sealed in the same manner as the organic EL element 1 to obtain the organic EL element 46.

[Production of Organic EL Element 45]

An organic EL element 47 was produced in the same manner as the organic EL element 46 except that the material constituting the cathode was changed from silver and indium to sliver and magnesium with respect to the organic EL element 46. The obtained organic EL element 47 was sealed in the same manner as the organic EL element 1 to obtain the organic EL element 47.

[Production of Organic EL Element 48]

An organic EL element 48 was produced in the same manner as the organic EL element 45 except that the material constituting the electron transporting layer was changed from $Alq_3$ to compound 94 with respect to the organic EL element 45. The obtained organic EL element 48 was sealed in the same manner as the organic EL element 1 to obtain the organic EL element 48.

[Production of Organic EL Element 49]

An organic EL element 49 was produced in the same manner as the organic EL element 46 except that the material constituting the electron transporting layer was changed from $Alq_3$ to compound 94 with respect to the organic EL element 46. The obtained organic EL element 49 was sealed in the same manner as the organic EL element 1 to obtain the organic EL element 49.

[Production of Organic EL Element 50]

An organic EL element 50 was produced in the same manner as the organic EL element 47 except that the material constituting the electron transporting layer was changed from $Alq_3$ compound 94 with respect to the organic EL element 47. The obtained organic EL element 50 was sealed in the same manner as the organic EL element 1 to obtain the organic EL element 50.

[Production of Organic EL Element 51]

On organic EL element 51 was produced in the same manner as the organic EL element 48 except that the material constituting the electron on transporting layer was changed from compound 94 to compound 10 with respect to the organic EL element 48. The obtained organic EL element 51 was sealed in the same manner as the organic EL element 1 to obtain the organic EL element 51.

[Production of Organic EL Element 52]

An organic EL element 52 was produced in the same manner as the organic EL element 49 except that the material constituting the electron transporting layer was changed from compound 94 to compound 10 with respect to the organic EL element 49. The obtained organic EL element 52 was sealed in the same manner as the organic EL element 1 to obtain the organic EL element 52.

[Production of Organic EL Element 53]

An organic EL element 53 was produced in the same manner as the organic EL element 50 except that the material constituting the electron transporting layer was changed from compound 94 to compound 10 with respect to the organic EL element 50. The obtained organic EL element 53 was sealed in the same manner as the organic EL element 1 to obtain the organic EL element 53.

[Production of Organic EL Element 54]

(Formation of Anode to Hole Blocking Layer)

The layers from the anode to the hole blocking layer were formed by the same method as that of the organic EL element 1.

(Formation of Electron Transporting Layer)

Next, the heating boat having compound 10 placed therein and the heating boat having potassium fluoride placed therein were each independently electrically heated to form an electron transporting layer having a film thickness of 20 nm, wherein ratio of the deposition rate of compound 10 to the deposition rate of potassium fluorides was adjusted to 75:25.

(Formation of Cathode)

Next, the element in which the layers up to the electron injecting layer had been formed was transferred to the second vacuum chamber while maintaining the vacuum state. After the pressure of the second vacuum chamber was reduced to $4 \times 10^{-4}$ Pa, the heating boat having silver placed therein was electrified to form a silver electrode layer having a film thickness of 0 nm so as to obtain a cathode, and thereby produce the organic EL element 54. The obtained organic EL element 54 was sealed in the sense manner as the organic EL element 1 to obtain the organic EL element 54.

[Production of Organic EL Element 55]

An organic EL element 55 was produced in the same manner as the organic EL element 54 except that the material constituting the cathode was changed from silver to silver and indium with respect to the organic EL element 54. The obtained organic EL element 55 was sealed in the same manner as the organic EL element 1 to obtain the organic EL element 55.

[Production of Organic EL Element 56]

An organic EL element 56 was produced in the same manner as the organic EL element 54 except that the material constituting the cathode was changed from silver to silver and magnesium with respect to the organic EL element 54. The obtained organic EL element 56 was sealed in the same manner as the organic EL element 1 to obtain the organic EL element 56.

[Production of Organic EL Element 57]

An organic EL element 57 was produced in the same manner as the organic EL element 54 except that the light-emitting dopant is changed from Ir-4 to Ir-26 with respect to the organic EL element 54. The obtained organic EL element 57 was sealed in the same manner as the organic EL element 1 to obtain the organic EL element 57.

[Production of Organic EL Element 58]

An organic EL element 58 was produced in the same manner as the organic EL element 55 except that the light-emitting dopant is changed from Ir-4 to Ir-26 with respect to the organic EL element 55. The obtained organic EL element 58 was sealed in the same manner as the organic EL element 1 to obtain the organic EL element 58.

[Production of Organic EL Element 59]

An organic EL element 59 was produced in the same manner as the organic EL element 56 except that the light emitting dopant is changed from Ir-4 to Ir-26 with respect to the organic EL element 56. The obtained organic EL element 59 was sealed in the same manner as the organic EL element 1 to obtain the organic EL element 59.

[Production of Organic EL Element 60]

(Formation of Anode to Cathode)

The layers from anode to cathode were formed by the same method as that of the organic EL element 57.

(Formation of Auxiliary Electrode)

A auxiliary electrode was formed on the cathode using a shadow mask by a deposition method, wherein the auxiliary electrode is formed by a silver pattern having a line width of 50 µm, a thickness of 1 µm, and a pitch distance of 1 mm.

(Formation of Adjacent Layer)

Next, the obtained element was transferred to the first vacuum chamber again, and the heating boat having compound 10 placed therein was electrically heated at a deposition rate of 0.1 nm/sec to 0.2 nm/sec to form a layer having a film thickness of 100 nm, and thereby the organic EL element 60 was produced. The obtained organic EL element 60 was sealed in the same manner as the organic EL element 1 to obtain the organic EL element 60.

[Production of Organic EL Element 61]

An organic EL element 61 was produced in the same manner as the organic EL element 60 except that the material constituting the cathode was changed from silver to silver and indium with respect to the organic EL element 60. The obtained organic EL element 61 was sealed in the same manner as the organic EL element 1 to obtain aha organic EL element 61.

[Production of Organic EL Element 62]

An organic EL element 62 was produced in the same manner as the organic EL element 60 except that the material constituting the cathode was changed from silver to silver and magnesium with respect to the organic EL element 60. The obtained organic EL element 62 was sealed in the same manner as the organic EL element 1 to obtain she organic EL element 62.

[Production of Organic EL Element 63]

An organic EL element 63 was produced in the same manner as the organic EL element 60 except that the material constituting the adjacent layer was changed from compound 10 to comparative compound 1 with respect to the organic EL element 60. The obtained organic EL element 63 was sealed in the same manner as the organic EL element 1 to obtain the organic EL element 63.

[Chemical Formula 69]

COMPARATIVE COMPOUND 1

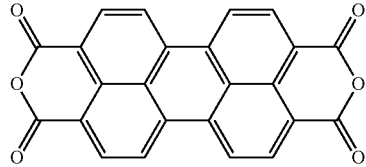

Evaluation of Organic EL Element

Driving voltage, efficiency and lifetime of each organic EL element produced above are measured. Evaluation of these items was performed below.

Incidentally, the light transmission of the cathodes of all organic EL elements for light with a wavelength of 550 nm was 50% or higher.

Elements obtained by forming films until the adjacent layer of each of the organic EL elements are separately produced; as a results of observing the state of the adjacent layer, particulate substance having light scattering property was not observed on the adjacent layers formed using $Alq_3$, Liq or compound 10, while particulate substance having light scattering property was observed on the adjacent layer formed using comparative compound 1.

[Measurement of Driving Voltage]

With respect to each organic EL element produced above, the voltage at the time when the sum of the front brightness on the anode side and the front brightness on the cathode side became 1000 $cd/m^2$ was regarded as the voltage of each organic EL element. First, the voltage was measured immediately after the organic EL element had been produced. Next, each organic EL element was driven to an initial brightness of 4000 $cd/m^2$, and time elapsed until the brightness was reduced to half of the initial brightness was measured. Incidentally, the brightness was measured using a spectroradiometer CS-1000 manufactured by Konica Minolta Sensing Inc.). The smaller the value of the obtained driving voltage is, the more preferable the result is.

The evaluation results obtained above are shown to Tables 1, 2 and 3.

TABLE 1

| ※ 1 | LIGHT EMITTING LAYER MATERIAL LIGHT EMITTING | ELECTRON TRANSPORTING LAYER ※ 2 | ※ 3 | FILM THICKNESS nm | ELECTRON INJECTING LAYER MATERIAL | FILM THICKNESS nm | CATHODE FIRST METAL | RATIO atm % | SECOND METAL | RATIO atm % | TOTAL FILM THICKNESS nm |
|---|---|---|---|---|---|---|---|---|---|---|---|
| 1 | Ir-4 | $Alq_3$ | — | 20 | LiF | 1 | Ag | 100 | — | — | 10 |
| 2 | Ir-4 | $Alq_3$ | — | 20 | LiF | 1 | Ag | 100 | — | — | 10 |
| 3 | Ir-4 | $Alq_3$ | — | 20 | LiF | 1 | Ag | 100 | — | — | 8 |
| 4 | Ir-4 | $Alq_3$ | — | 20 | LiF | 1 | Ag | 100 | — | — | 8 |
| 5 | Ir-4 | $Alq_3$ | — | 20 | LiF | 1 | Ag | 100 | — | — | 8 |
| 6 | Ir-4 | $Alq_3$ | — | 20 | LiF | 1 | Ag | 100 | — | — | 8 |
| 7 | Ir-4 | $Alq_3$ | — | 20 | LiF | 1 | Ag | 100 | — | — | 8 |
| 8 | Ir-4 | $Alq_3$ | — | 20 | LiF | 1 | Ag | 100 | — | — | 8 |
| 9 | Ir-4 | $Alq_3$ | — | 20 | LiF | 1 | Ag | 100 | — | — | 15 |
| 10 | Ir-4 | $Alq_3$ | — | 20 | LiF | 1 | Ag | 100 | — | — | 20 |
| 11 | Ir-4 | $Alq_3$ | — | 20 | LiF | 1 | Ag | 100 | — | — | 8 |
| 12 | Ir-4 | $Alq_3$ | — | 20 | LiF | 1 | Ag | 100 | — | — | 8 |
| 13 | Ir-4 | $Alq_3$ | — | 20 | LiF | 1 | Ag | 100 | — | — | 8 |
| 14 | Ir-4 | $Alq_3$ | — | 20 | LiF | 1 | Ag | 100 | — | — | 8 |
| 15 | Ir-4 | $Alq_3$ | — | 20 | LiF | 1 | Ag | 100 | — | — | 8 |
| 16 | Ir-4 | $Alq_3$ | — | 20 | LiF | 1 | Ag | 100 | — | — | 4 |
| 17 | Ir-4 | $Alq_3$ | — | 20 | LiF | 1 | Ag | 100 | — | — | 4 |
| 18 | Ir-4 | $Alq_3$ | — | 20 | LiF | 1 | Ag | 100 | — | — | 1.8 |
| 19 | Ir-4 | $Alq_3$ | — | 20 | LiF | 1 | Ag | 95 | In | 5 | 10 |
| 20 | Ir-4 | $Alq_3$ | — | 20 | LiF | 1 | Ag | 95 | In | 5 | 10 |
| 21 | Ir-4 | $Alq_3$ | — | 20 | LiF | 1 | Ag | 95 | In | 5 | 8 |
| 22 | Ir-4 | $Alq_3$ | — | 20 | LiF | 1 | Ag | 95 | In | 5 | 8 |

TABLE 1-continued

| | | | | | | | | | | |
|---|---|---|---|---|---|---|---|---|---|---|
| 23 | Ir-4 | Alq$_3$ | — | 20 | LiF | 1 | Ag | 95 | In | 5 | 8 |
| 24 | Ir-4 | Alq$_3$ | — | 20 | LiF | 1 | Ag | 95 | In | 5 | 8 |
| 25 | Ir-4 | Alq$_3$ | — | 20 | LiF | 1 | Ag | 95 | In | 5 | 8 |

| | CATHODE | ADJACENT LAYER | | | EVALUATION | | | |
|---|---|---|---|---|---|---|---|---|
| ※1 | TRANS-MISSION % | MATERIAL | REFRACTIVE INDEX (550 nm) | FILM THICKNESS nm | AUXILIARY ELECTRODE | DRIVING VOLTAGE V | LUMINOUS EFFICIENCY RELATIVE VALUE | REMARK |
| 1 | >50 | — | — | — | NO | 5.32 | 100 | COMPARISON |
| 2 | >50 | Alq$_3$ | 1.73 | 100 | NO | 5.33 | 95 | COMPARISON |
| 3 | >50 | — | — | — | NO | 5.61 | 100 | COMPARISON |
| 4 | >50 | Alq$_3$ | 1.73 | 15 | NO | 4.81 | 124 | PRESENT INVENTION |
| 5 | >50 | Alq$_3$ | 1.73 | 30 | NO | 4.84 | 124 | PRESENT INVENTION |
| 6 | >50 | Alq$_3$ | 1.73 | 50 | NO | 4.82 | 132 | PRESENT INVENTION |
| 7 | >50 | Alq$_3$ | 1.73 | 80 | NO | 4.83 | 152 | PRESENT INVENTION |
| 8 | >50 | Alq$_3$ | 1.73 | 100 | NO | 4.82 | 178 | PRESENT INVENTION |
| 9 | 47 | Alq$_3$ | 1.73 | 100 | NO | 4.82 | 110 | COMPARISON |
| 10 | 42 | Alq$_3$ | 1.73 | 100 | NO | 4.82 | 83 | COMPARISON |
| 11 | >50 | Alq$_3$ | 1.73 | 120 | NO | 4.82 | 169 | PRESENT INVENTION |
| 12 | >50 | Alq$_3$ | 1.73 | 150 | NO | 4.82 | 147 | PRESENT INVENTION |
| 13 | >50 | Alq$_3$ | 1.73 | 160 | NO | 4.82 | 132 | PRESENT INVENTION |
| 14 | >50 | Alq$_3$ | 1.73 | 210 | NO | 5.35 | 97 | COMPARISON |
| 15 | >50 | Alq$_3$ | 1.73 | 240 | NO | 5.33 | 91 | COMPARISON |
| 16 | >50 | — | — | — | NO | 5.55 | 93 | COMPARISON |
| 17 | >50 | Alq$_3$ | 1.73 | 100 | NO | 5.01 | 165 | PRESENT INVENTION |
| 18 | >50 | Alq$_3$ | 1.73 | 100 | NO | 11.41 | 42 | COMPARISON |
| 19 | >50 | — | — | — | NO | 5.33 | 100 | COMPARISON |
| 20 | >50 | Alq$_3$ | 1.73 | 100 | NO | 5.33 | 95 | COMPARISON |
| 21 | >50 | — | — | — | NO | 5.65 | 90 | COMPARISON |
| 22 | >50 | Alq$_3$ | 1.73 | 15 | NO | 4.83 | 126 | PRESENT INVENTION |
| 23 | >50 | Alq$_3$ | 1.73 | 30 | NO | 4.82 | 130 | PRESENT INVENTION |
| 24 | >50 | Alq$_3$ | 1.73 | 50 | NO | 4.84 | 135 | PRESENT INVENTION |
| 25 | >50 | Alq$_3$ | 1.73 | 8 | NO | 4.81 | 154 | PRESENT INVENTION |

※1: NUMBER OF ORGANIC EL ELEMENT
※2: ELECTRON TRANSPORTING MATERIAL
※3: ALKALI METAL OR ALKALI METAL COMPOUND

TABLE 2

| | LIGHT EMITTING LAYER | ELECTRON TRANSPORTING LAYER | | | ELECTRON INJECTING LAYER | | CATHODE | | | | TOTAL |
|---|---|---|---|---|---|---|---|---|---|---|---|
| ※1 | MATERIAL LIGHT EMITTING | ※2 | ※3 | FILM THICKNESS nm | MATERIAL | FILM THICKNESS nm | FIRST METAL | RATIO atm % | SECOND METAL | RATIO atm % | FILM THICKNESS nm |
| 26 | Ir-4 | Alq$_3$ | — | 20 | LiF | 1 | Ag | 95 | In | 5 | 8 |
| 27 | Ir-4 | Alq$_3$ | — | 20 | LiF | 1 | Ag | 95 | In | 5 | 8 |
| 28 | Ir-4 | Alq$_3$ | — | 20 | LiF | 1 | Ag | 95 | In | 5 | 8 |
| 29 | Ir-4 | Alq$_3$ | — | 20 | LiF | 1 | Ag | 95 | In | 5 | 8 |
| 30 | Ir-4 | Alq$_3$ | — | 20 | LiF | 1 | Ag | 95 | In | 5 | 8 |
| 31 | Ir-4 | Alq$_3$ | — | 20 | LiF | 1 | Ag | 95 | In | 5 | 8 |
| 32 | Ir-4 | Alq$_3$ | — | 20 | LiF | 1 | Ag | 95 | In | 5 | 8 |
| 33 | Ir-4 | Alq$_3$ | — | 20 | LiF | 1 | Ag | 95 | In | 5 | 8 |
| 34 | Ir-4 | Alq$_3$ | — | 20 | LiF | 1 | Ag | 95 | In | 5 | 8 |
| 35 | Ir-4 | Alq$_3$ | — | 20 | LiF | 1 | Ag | 95 | In | 5 | 8 |
| 36 | Ir-4 | Alq$_3$ | — | 20 | LiF | 1 | Ag | 95 | In | 5 | 8 |
| 37 | Ir-4 | Alq$_3$ | — | 20 | LiF | 1 | Ag | 95 | In | 5 | 8 |

TABLE 2-continued

| | | | | | | | | | | | | |
|---|---|---|---|---|---|---|---|---|---|---|---|---|
| 38 | Ir-4 | Alq$_3$ | — | 20 | LiF | 1 | Ag | 95 | In | 5 | 8 |
| 39 | Ir-4 | Alq$_3$ | — | 20 | LiF | 1 | Ag | 95 | In | 5 | 8 |
| 40 | Ir-4 | Alq$_3$ | — | 20 | LiF | 1 | Ag | 95 | In | 5 | 8 |
| 41 | Ir-4 | Alq$_3$ | — | 20 | LiF | 1 | Ag | 95 | In | 5 | 8 |
| 42 | Ir-4 | Alq$_3$ | — | 20 | LiF | 1 | Ag | 95 | In | 5 | 1.8 |
| 43 | Ir-4 | Alq$_3$ | — | 20 | LiF | 1 | Ag | 100 | — | — | 8 |
| 44 | Ir-4 | Alq$_3$ | — | 20 | LiF | 1 | Ag | 100 | — | — | 8 |
| 45 | Ir-4 | Alq$_3$ | — | 20 | KF | 2 | Ag | 100 | — | — | 8 |
| 46 | Ir-4 | Alq$_3$ | — | 20 | KF | 2 | Ag | 95 | In | 5 | 8 |
| 47 | Ir-4 | Alq$_3$ | — | 20 | KF | 2 | Ag | 95 | Mg | 5 | 8 |
| 48 | Ir-4 | 94 | — | 20 | KF | 2 | Ag | 100 | — | — | 8 |
| 49 | Ir-4 | 94 | — | 20 | KF | 2 | Ag | 95 | In | 5 | 8 |
| 50 | Ir-4 | 94 | — | 20 | KF | 2 | Ag | 95 | Mg | 5 | 8 |

| | CATHODE | ADJACENT LAYER | | | EVALUATION | | | |
|---|---|---|---|---|---|---|---|---|
| | | | | | | LUMINOUS | | |
| ※1 | TRANS-MISSION % | MATERIAL | REFRACTIVE INDEX (550 nm) | FILM THICKNESS nm | AUXILIARY ELECTRODE | DRIVING VOLTAGE V | EFFICIENCY RELATIVE VALUE | REMARK |
| 26 | >50 | Alq$_3$ | 1.73 | 100 | NO | 4.84 | 182 | PRESENT INVENTION |
| 27 | >50 | Alq$_3$ | 1.73 | 120 | NO | 4.85 | 174 | PRESENT INVENTION |
| 28 | >50 | Alq$_3$ | 1.73 | 150 | NO | 4.8 | 154 | PRESENT INVENTION |
| 29 | >50 | Alq$_3$ | 1.73 | 180 | NO | 4.80 | 139 | PRESENT INVENTION |
| 30 | >50 | Alq$_3$ | 1.73 | 210 | NO | 5.31 | 97 | COMPARISON |
| 31 | >50 | Alq$_3$ | 1.73 | 240 | NO | 5.33 | 91 | COMPARISON |
| 32 | >50 | 10 | 1.79 | 15 | NO | 4.52 | 130 | PRESENT INVENTION |
| 33 | >50 | 10 | 1.79 | 30 | NO | 4.51 | 141 | PRESENT INVENTION |
| 34 | >50 | 10 | 1.79 | 50 | NO | 4.52 | 150 | PRESENT INVENTION |
| 35 | >50 | 10 | 1.79 | 80 | NO | 4.51 | 172 | PRESENT INVENTION |
| 36 | >50 | 10 | 1.79 | 100 | NO | 4.50 | 198 | PRESENT INVENTION |
| 37 | >50 | 10 | 1.79 | 120 | NO | 4.55 | 164 | PRESENT INVENTION |
| 38 | >50 | 10 | 1.79 | 150 | NO | 4.50 | 152 | PRESENT INVENTION |
| 39 | >50 | 10 | 1.79 | 180 | NO | 4.52 | 131 | PRESENT INVENTION |
| 40 | >50 | 10 | 1.79 | 210 | NO | 5.33 | 97 | COMPARISON |
| 41 | >50 | 10 | 1.79 | 240 | NO | 5.31 | 91 | COMPARISON |
| 42 | >50 | 10 | 1.79 | 100 | NO | 11.14 | 42 | COMPARISON |
| 43 | >50 | SiO$_2$ | 1.46 | 100 | NO | 5.62 | 90 | COMPARISON |
| 44 | >50 | Liq | 1.72 | 100 | NO | 4.84 | 173 | PRESENT INVENTION |
| 45 | >50 | 10 | 1.79 | 100 | NO | 4.24 | 203 | PRESENT INVENTION |
| 46 | >50 | 10 | 1.79 | 100 | NO | 4.23 | 213 | PRESENT INVENTION |
| 47 | >50 | 10 | 1.79 | 100 | NO | 3.92 | 203 | PRESENT INVENTION |
| 48 | >50 | 10 | 1.79 | 100 | NO | 4.03 | 213 | PRESENT INVENTION |
| 49 | >50 | 10 | 1.79 | 100 | NO | 4.02 | 223 | PRESENT INVENTION |
| 50 | >50 | 10 | 1.79 | 100 | NO | 3.75 | 213 | PRESENT INVENTION |

※1: NUMBER OF ORGANIC EL ELEMENT
※2: ELECTRON TRANSPORTING MATERIAL
※3: ALKALI METAL OR ALKALI METAL COMPOUND

TABLE 3

| ※1 | LIGHT EMITTING LAYER MATERIAL LIGHT EMITTING | ELECTRON TRANSPORTING LAYER ※2 | ELECTRON TRANSPORTING LAYER ※3 | ELECTRON TRANSPORTING LAYER FILM THICKNESS nm | ELECTRON INJECTING LAYER MATERIAL | ELECTRON INJECTING LAYER FILM THICKNESS nm | CATHODE FIRST METAL | CATHODE RATIO atm % | CATHODE SECOND METAL | CATHODE RATIO atm % | TOTAL FILM THICKNESS nm |
|---|---|---|---|---|---|---|---|---|---|---|---|
| 51 | Ir-4 | 10 | — | 20 | KF | 2 | Ag | 100 | — | — | 8 |
| 52 | Ir-4 | 10 | — | 20 | KF | 2 | Ag | 95 | In | 5 | 8 |
| 53 | Ir-4 | 10 | — | 20 | KF | 2 | Ag | 95 | Mg | 5 | 8 |
| 54 | Ir-4 | 10 | KF | 20 | — | — | Ag | 100 | — | — | 8 |
| 55 | Ir-4 | 10 | KF | 20 | — | — | Ag | 95 | In | 5 | 8 |
| 56 | Ir-4 | 10 | KF | 20 | — | — | Ag | 95 | Mg | 5 | 8 |
| 57 | Ir-26 | 10 | KF | 20 | — | — | Ag | 100 | — | — | 8 |
| 58 | Ir-26 | 10 | KF | 20 | — | — | Ag | 95 | In | 5 | 8 |
| 59 | Ir-26 | 10 | KF | 20 | — | — | Ag | 95 | Mg | 5 | 8 |
| 60 | Ir-26 | 10 | KF | 20 | — | — | Ag | 100 | — | — | 8 |
| 61 | Ir-26 | 10 | KF | 20 | — | — | Ag | 95 | In | 5 | 8 |
| 62 | Ir-26 | 10 | KF | 20 | — | — | Ag | 95 | Mg | 5 | 8 |
| 63 | Ir-26 | 10 | KF | 20 | — | — | Ag | 100 | — | — | 8 |

| ※1 | CATHODE TRANSMISSION % | ADJACENT LAYER MATERIAL | ADJACENT LAYER REFRACTIVE INDEX (550 nm) | ADJACENT LAYER FILM THICKNESS nm | EVALUATION AUXILIARY ELECTRODE | EVALUATION DRIVING VOLTAGE V | EVALUATION LUMINOUS EFFICIENCY RELATIVE VALUE | REMARK |
|---|---|---|---|---|---|---|---|---|
| 51 | >50 | 10 | 1.79 | 100 | NO | 3.74 | 233 | PRESENT INVENTION |
| 52 | >50 | 10 | 1.79 | 100 | NO | 3.71 | 243 | PRESENT INVENTION |
| 53 | >50 | 10 | 1.79 | 100 | NO | 3.43 | 233 | PRESENT INVENTION |
| 54 | >50 | 10 | 1.79 | 100 | NO | 3.42 | 253 | PRESENT INVENTION |
| 55 | >50 | 10 | 1.79 | 100 | NO | 3.73 | 243 | PRESENT INVENTION |
| 56 | >50 | 10 | 1.79 | 100 | NO | 3.44 | 233 | PRESENT INVENTION |
| 57 | >50 | 10 | 1.79 | 100 | NO | 3.42 | 263 | PRESENT INVENTION |
| 58 | >50 | 10 | 1.79 | 100 | NO | 3.72 | 253 | PRESENT INVENTION |
| 59 | >50 | 10 | 1.79 | 100 | NO | 3.43 | 243 | PRESENT INVENTION |
| 60 | >50 | 10 | 1.79 | 100 | YES | 3.24 | 263 | PRESENT INVENTION |
| 61 | >50 | 10 | 1.79 | 100 | YES | 3.51 | 253 | PRESENT INVENTION |
| 62 | >50 | 10 | 1.79 | 100 | YES | 3.21 | 243 | PRESENT INVENTION |
| 63 | >50 | ※4 | 1.79 | 100 | NO | 5.31 | 100 | COMPARISON |

※1: NUMBER OF ORGANIC EL ELEMENT
※2: ELECTRON TRANSPORTING MATERIAL
※3: ALKALI METAL OR ALKALI METAL COMPOUND
※4 COMPARATIVE COMPOUND 1

It is clearly known from the results shown in the tables that, compared with the organic EL element of the comparative example, the organic EL elements of the present invention have lower driving voltage end excellent luminous efficiency. Particularly, organic EL elements 32 to 39, whose adjacent layer contains compound 10, exhibit higher luminous efficiency, and are excellent when the thickness of the adjacent layer falls within a range of 50 to 150 nm. Further, organic EL elements 54 to 62, whose electron injecting layer contains potassium fluoride, exhibit further excellent luminous efficiency.

Production of Top Emission Type Organic EL Element

A top emission type organic EL element was produced by the same method as the aforesaid dual emission type organic EL element except that a SiO$_2$ film with a thickness of 1 μm was formed by a sputtering method onto entire surface of a metal foil of SUS 304 with a film thickness of 50 μm, and further, an aluminum-neodymium alloy film with a thickness of 100 nm was formed in a desired pattern onto the film of SiO$_2$ by a sputtering method to thereby form an anode; and the advantages of the present invention have been confirmed on the top emission type organic EL element.

EXPLANATION OF REFERENCE NUMERALS 1A, 1B organic EL element
2 supporting substrate
3 anode
4 hole injecting layer
5 hole transporting layer
6 light emitting layer
7 electron transporting layer
8 cathode
8-1 auxiliary electrode
9 adjacent layer
20 illumination device
21 glass substrate
22 glass case
23 seal material
24 nitrogen gas
25 hygroscopic compound

The invention claimed is:
1. An organic electroluminescence element comprising:
a supporting substrate; and
a cathode, a light emitting layer and an adjacent layer provided on the supporting substrate, wherein the adjacent layer is arranged adjacent to the outer side of the cathode (i.e., the side opposite to the light emitting layer),
wherein the cathode is a transparent layer containing a metal and having a film thickness of 2 nm or more but less than 10 nm; and
wherein the adjacent layer has a refractive index of between 1.6 and 1.95, a film thickness of between 15 nm and 180 nm, and contains no light scattering particle.
2. The organic electroluminescence element according to claim 1, wherein the adjacent layer contains a metal complex compound having a quinoline derivative as its ligand.
3. The organic electroluminescence element according to claim 1, wherein the adjacent layer contains a compound represented by the following general formula (1):

(Ar1)$n1$-Y1  General Formula (1)

where n1 represents an integer of 1 or more; Y1 represents either a substituent if n1 is one, or a bond or an n1-valent linking group if n1 is 2 or more; Ar1 represents a group represented by the following general formula (A); and, if n1 is or more, a plurality of Ar1 may be either identical to or different from each other; wherein the compound represented by General Formula (1) has at least two condensed aromatic heterocycles in the molecule, each formed by condensing three or more rings,

[Chemical Formula 1]

GENERAL FORMULA (A)

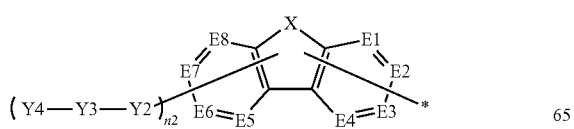

where X represents —N(R)—, —O—, —S— or —Si(R)(R')—, and E1 to E8 each represent —C(R1)= or —N=, wherein R, R' and R1 each represent a hydrogen atom, a substituent or a linking site with Y1; * represents a linking site with Y1; Y2 represents a bond or a divalent linking group; Y3 and Y4 each represent a group derived from a 5-membered or 6-membered aromatic ring, wherein at least one of Y3 and Y4 represents a group derived from an aromatic heterocycle containing a nitrogen atom as a ring constituent atom; and n2 represents an integer of 1 to 4.

4. The organic electroluminescence element according to claim 3, wherein the compound represented by the general formula (1) is a compound represented by the following general formula (2):

[Chemical Formula 2]

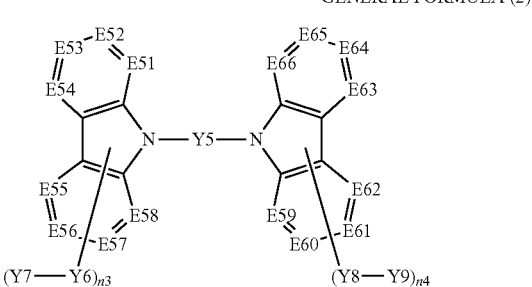

GENERAL FORMULA (2)

where Y5 represents a divalent linking group which is an arylene group, a heteroarylene group or a combination of the arylene group and the heteroarylene group; E51 to E66 each represent —C(R3)= or —N=, wherein R3 represents a hydrogen atom or a substituent; Y6 to Y9 each represent a group derived from an aromatic hydrocarbon ring or a group derived from an aromatic heterocycle, wherein at least one of Y6 and Y7 and at least one of Y8 and Y9 each represent a group derived from an aromatic heterocycle containing an N atom; and n3 and n4 each represent an integer of 0 to 4, wherein the sum of n3 and n4 is 2 or more.

5. The organic electroluminescence element according to claim 4, wherein the compound represented by the general formula (2) is a compound represented by the following general formula (3):

[Chemical Formula 3]

GENERAL FORMULA (3)

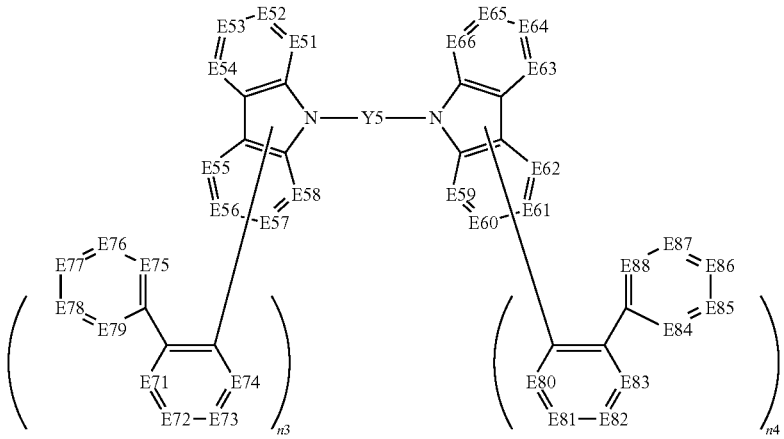

where Y5 represents a divalent linking group which is an arylene group, a heteroarylene group or a combination of the arylene group and the heteroarylene group; E51 to E66 and E71 to E88 each represent —C(R3)= or —N=, wherein R3 represents a hydrogen atom or a substituent, and wherein at least one of E71 to E79 and at least one of E80 to E88 each represent —N=; and n3 and n4 each represent an integer of 0 to 4, wherein the sum of n3 and n4 is 2 or more.

6. The organic electroluminescence element according to claim 1, wherein the main component of the cathode is silver.

7. The organic electroluminescence element according to claim 1, further comprising:
an electron transporting layer arranged between the cathode and the light emitting layer,
wherein the electron transporting layer contains an alkali metal or an alkali metal compound.

8. The organic electroluminescence element according to claim 7, wherein the alkali metal or the alkali metal compound is kalium or a kalium compound.

9. The organic electroluminescence element according to claim 7, wherein the electron transporting layer contains a compound represented by one of general formulas (1) to (3).

10. The organic electroluminescence element according to claim 1, wherein the light emitting layer contains a compound represented by the following general formula (4):

[Chemical Formula 4]

GENERAL FORMULA (4)

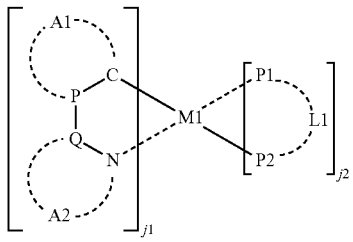

where P and Q each represent a carbon atom or a nitrogen atom; A1 represents an atom group which forms an aromatic hydrocarbon ring or an aromatic heterocycle with P—C; A2 represents an atom group which forms an aromatic heterocycle with Q-N; P1-L1-P2 represents a bidentate ligand, wherein P1 and P2 each independently represent a carbon atom, a nitrogen atom or an oxygen atom, and L1 represents an atom group which forms the bidentate ligand with P1 and P2; j1 represents an integer of 1 to 3, and j2 represents an integer of 0 to 2, wherein the sum of j1 and j2 is 2 or 3; and M1 represents a transition metal element of groups 8 to 10 in the periodic table of elements.

11. The organic electroluminescence element according to claim 10, wherein the compound represented by the general formula (4) is a compound represented by the following general formula (5):

[Chemical Formula 5]

GENERAL FORMULA (5)

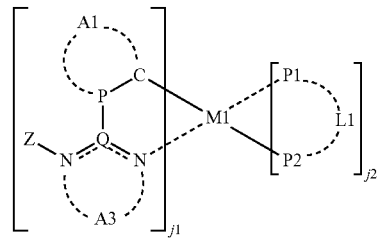

where Z represents a hydrocarbon ring group or a heterocyclic group; P and Q each represent a carbon atom or a nitrogen atom; A1 represents an atom group which forms an aromatic hydrocarbon ring or an aromatic heterocycle with P—C; A3 represents —C(R01)=C(R02)-, —N=C(R02)-, —C(R01)=N— or =N—N—, wherein R01 and R02 each represent a hydrogen atom or a substituent; P1-L1-P2 represents a bidentate ligand, wherein P1 and P2 each independently represent a carbon atom, a nitrogen atom or an oxygen atom, and L1 represents an atom group which forms the bidentate ligand with P1 and P2; j1 represents an integer of 1 to 3, and j2 represents an integer of 0 to 2, wherein the sum of j1 and j2 is 2 or 3; and M1 represents a transition metal element of groups 8 to 10 in the periodic table of elements.

12. The organic electroluminescence element according to claim 10, wherein M1 represents iridium.

13. The organic electroluminescence element according to claim 1, further comprising:
  an auxiliary electrode arranged between the cathode and the adjacent layer.

14. The organic electroluminescence element according to claim 1, wherein the organic electroluminescence element is a dual emission type organic electroluminescence element.

15. An illumination device comprising an organic electroluminescence element described in claim 1.

16. A display device comprising an organic electroluminescence element described in claim 1.

* * * * *